United States Patent
Wang et al.

(10) Patent No.: US 10,920,229 B2
(45) Date of Patent: Feb. 16, 2021

(54) **METHOD FOR IMPROVING HETEROLOGOUS SYNTHESIS OF *ESCHERICHIA COLI* INTO POLYKETIDES AND USE OF SAME**

(71) Applicant: Shanghai Institutes for Biological Sciences, Chinese Academy of Sciences, Shanghai (CN)

(72) Inventors: Yong Wang, Shanghai (CN); Zhiqiang Xiong, Shangai (CN); Shujie Song, Shanghai (CN); Qiaoxia Liu, Shanghai (CN); Jianfeng Wang, Shanghai (CN)

(73) Assignee: CAS Center for Excellence in Molecular Plant Sciences, Shanghai (CN)

( * ) Notice: Subject to any disclaimer, the term of this patent is extended or adjusted under 35 U.S.C. 154(b) by 243 days.

(21) Appl. No.: 15/523,829

(22) PCT Filed: May 18, 2015

(86) PCT No.: PCT/CN2015/079161
§ 371 (c)(1),
(2) Date: Sep. 1, 2017

(87) PCT Pub. No.: WO2016/008332
PCT Pub. Date: Jan. 21, 2016

(65) Prior Publication Data
US 2018/0016585 A1 Jan. 18, 2018

(30) Foreign Application Priority Data
Jul. 16, 2014 (CN) .......................... 2014 1 0338738

(51) Int. Cl.
| C12N 15/70 | (2006.01) |
| C12N 15/113 | (2010.01) |
| C12N 9/12 | (2006.01) |
| C12P 19/62 | (2006.01) |
| C12P 17/08 | (2006.01) |
| C07H 17/08 | (2006.01) |
| C12N 15/09 | (2006.01) |
| C12Q 1/18 | (2006.01) |
| C12R 1/465 | (2006.01) |

(52) U.S. Cl.
CPC ............ *C12N 15/70* (2013.01); *C07H 17/08* (2013.01); *C12N 9/1288* (2013.01); *C12N 15/09* (2013.01); *C12N 15/113* (2013.01); *C12P 17/08* (2013.01); *C12P 19/62* (2013.01); *C12Q 1/18* (2013.01); *C12R 1/465* (2013.01); *C12N 2320/12* (2013.01); *C12N 2330/31* (2013.01); *C12N 2330/50* (2013.01)

(58) Field of Classification Search
None
See application file for complete search history.

(56) References Cited

FOREIGN PATENT DOCUMENTS

| CN | 101215557 A | 7/2008 |
| CN | 101255413 A | 9/2008 |
| CN | 103849642 A | 6/2014 |

OTHER PUBLICATIONS

Kizer et al. Application of Functional Genomics to Pathway Optimization for Increased Isoprenoid Production. Appl. Environ. Microbiol. 74:3229-3241, 2008.*
Murli et al. Metabolic engineering of Escherichia coli for improved 6-deoxyerythronolide B production. J Ind Microbiol Biotechnol (2003) 30: 500-509.*
International Search Report for PCT/CN2015/079161 (dated Jan. 21, 2016).
Zhang, Li-hua et al., "Cloning and Expression of Polyketide Synthases Gene eryA III of Saccharopolyspora etythraea in *Escherichia coli*", Letter in Biotechnology, vol. 21, No. 6, Nov. 30, 2010, ISSN: 1009-0002, pp. 794-797.
Reeves, Andrew R. et al., "Engineering precursor flow for increased erythromycin production in Aeromicrobium erythreum", Metabolic Engineering, vol. 6, issue 4, Dec. 31, 2004, ISSN: 1096-7176, pp. 300-312.

* cited by examiner

*Primary Examiner* — Iqbal H Chowdhury
(74) *Attorney, Agent, or Firm* — Banner & Witcoff, Ltd.

(57) ABSTRACT

The present invention relates to a method for improving the heterologous synthesis of a polyketide by *E. coli* and use thereof. The yield of the polyketide heterologously synthesized by *E. coli* is significantly increased by attenuating the expression of seventy-two genes, such as sucC and talB, in a host strain, wherein the highest yield increase rate can reach 60% or more. Currently, erythromycin is the most clear model compound in the study on the biosynthesis of polyketids. The production strain of the present invention enables massive accumulation of 6-deoxyerythronolide (6-dEB), an erythromycin precursor, in the fermentation process, laying the foundation for the industrial production of the heterologous synthesis of erythromycin by *E. coli*.

10 Claims, 4 Drawing Sheets
Specification includes a Sequence Listing.

METHOD FOR IMPROVING HETEROLOGOUS SYNTHESIS OF *ESCHERICHIA COLI* INTO POLYKETIDES AND USE OF SAME

TECHNICAL FIELD

The present invention falls within the fields of synthetic biology and industrial biotechnology, in particular, the present invention relates to a method for improving the heterologous synthesis of a polyketide by *E. coli* and use thereof.

BACKGROUND ART

Natural products play an important role in the process of drug development and discovery. Over the past decade, researchers have used natural products heterologously synthesized and the products have shown great potential. The heterologous biosynthesis of polyketids is one of the branches researched deeply and progressed rapidly in the current field of synthetic biology. Donadio proposed a synthetic model of 6-deoxyerythromycin lactone B in 1991, and studies on erythromycin polyketide synthases (PKSs) have thus become a paradigm for Type I PKSs. The biosynthesis of erythromycin is divided into two parts: the first is the formation of 6-deoxyerythronolide-B (6-dEB), the parent nucleus of erythromycin; and the second is the sidechain glycosylation of 6-dEB to synthesize erythromycin. 6-dEB is the first intermediate that can be isolated during the synthesis of erythromycin, and the starting materials for the synthesis of 6-dEB are propionic acid and methylmalonic acid. The entire process is catalyzed by polyketide synthases. Engineering ideas promote researchers to construct an engineered strain for the heterologous synthesis of natural products. As the metabolic network of *E. coli* has been researched most deeply, *E. coli* is often used as the chassis cell for engineered strains.

In 2001, Pfeifer et al. heterologously synthesized 6-dEB, the first precursor of erythromycin, using *E. coli*, opening the first line of the heterologous biosynthesis of erythromycin. Later researchers have also made many attempts to obtain erythromycin efficiently through *E. coli*, for example, in order to improve plasmid stability, Murli et al., in 2003, obtained an engineered strain K207-3/pKOS207-129/pBP130, with 22.5 mg/L of 6-dEB being obtained by culturing the same in a shake flask, by modifying pBP144 to pKOS207-129 through integrating genes pccB and pccA into the YgfG site encoding methylmalonyl-CoA decarboxylase in *E. coli* and replacing the starting site of pET28a derived from pBR322 with the replication origin of RSF1010. In order to improve the stability of the host itself, WANG Yong et al. obtained a chromosome-modified stable strain by integrating erythromycin polyketide synthase genes eryAI, AII and AIII into the chromosome of *E. coli* through a chromosome recombination Red/ET method, wherein the strain may stably synthesize 6-dEB, an intermediate of erythromycin, compared with the co-expression of multiple plasmids.

Over the recent decade, the heterologous synthesis of polyketids with erythromycin as the representative in *E. coli* has made a series of significant progresses, and erythromycin A was successfully synthesized in *E. coli*. However, there are still many problems, for example, the yield of erythromycin in *E. coli* is too low, compared with the original strain, *Saccharopolyspora erythraea*. MENG Hailin et al., in 2011, found that the actual yield of polyketids synthesized by *E. coli* was only about 1/10 of the theoretical yield currently after analyzing the metabolic network of *E. coli* using an in silico analysis and research platform, indicating that the heterogeneous synthetic pathway of polyketids is regulated by the global network of *E. coli*. Therefore, by modifying the global network of *E. coli*, it is possible to further improve its ability to heterologously synthesize polyketids.

SUMMARY OF THE INVENTION

An object of the present invention is to provide a method for improving the heterologous synthesis of a polyketide by *E. coli* and use thereof.

In a first aspect of the present invention, provided is a method for promoting a host strain for synthesizing the polyketide 6-deoxyerythronolide to synthesize the polyketide 6-deoxyerythronolide biologically, the method comprising:

(1) attenuating the expression of a target gene in the host strain for synthesizing the polyketide 6-deoxyerythronolide; wherein, the target gene is selected from:

(a) a gene for nucleotide synthesis and other metabolism modules, purT, lsrC, hemN, zwf, pgl, gnd, rpe, talA, talB, tktA, tktB, ulaE or yieK;

(b) a gene for pentose phosphate and glyoxylate pathway modules, yaeR, rpiA, rpiB, purH, pyrB, pyrI, cysQ, pyrC, gmk, guaA, guaB, ndk, pyrF, pyrE, pyrH or hpt;

(c) a gene for TCA cycle and oxidative phosphorylation modules, frdD, frdA, sdhA, sdhB, sdhC, sdhD, sucC, sucD, cyoA or cyoB;

(d) a gene for carbohydrate metabolism module, aceF, pgi, lpdA, ppk, ptsH, ptsI, glcF, glcE, fsaA or agaW;

(e) a gene for 6-dEB precursor metabolism module, yjiM, scpA, scpB, tdcD, tdcE, pflB, pflD, PaaF, ackA, pta or ybiW;

(f) a gene target for fatty acid metabolism module, fadJ, fadB, dhaK1, dhaK2 or dhaH;

(g) a gene for amino acid and protein synthetic metabolism modules, leuC, leuD, serC, serB, serA, gdhA or tnaA; or (h) the combination of frdD+sucC, the combination of lsrC+frdD, the combination of lsrC+sucC, the combination of frdD+rpiA, the combination of talA+guaB or the combination of zwf+guaB; and (2) culturing the strain prepared in step (1), thereby synthesizing the polyketide 6-deoxyerythronolide biologically.

In a preferred embodiment, attenuating the expression of a target gene in the host strain for synthesizing the polyketide 6-deoxyerythronolide includes: introducing an interfering molecule that inhibits the expression of the target gene or knocking out the target gene.

In another preferred embodiment, the interfering molecule that inhibits the expression of the target gene is directed to the following (or has the same itself):

a sequence shown in SEQ ID NO: 37 in sucC or a complementary sequence thereof, a sequence shown in SEQ ID NO: 2 in tdcD or a complementary sequence thereof, a sequence shown in SEQ ID NO: 3 in scpB or a complementary sequence thereof, a sequence shown in SEQ ID NO: 4 in scpA or a complementary sequence thereof, a sequence shown in SEQ ID NO: 5 in ybiW or a complementary sequence thereof, a sequence shown in SEQ ID NO: 6 in pflB or a complementary sequence thereof, a sequence shown in SEQ ID NO: 7 in tdcE or a complementary sequence thereof, a sequence shown in SEQ ID NO: 8 in pflD or a complementary sequence thereof,
a sequence shown in SEQ ID NO: 9 in paaF or a complementary sequence thereof,
a sequence shown in SEQ ID NO: 10 in fadJ or a complementary sequence thereof,
a sequence shown in SEQ ID NO: 11 in fadB or a complementary sequence thereof,
a sequence shown in SEQ ID NO: 12 in ackA or a complementary sequence thereof,
a sequence shown in SEQ ID NO: 13 in pta or a complementary sequence thereof,
a sequence shown in SEQ ID NO: 14 in leuD or a complementary sequence thereof,
a sequence shown in SEQ ID NO: 15 in leuC or a complementary sequence thereof,
a sequence shown in SEQ ID NO: 16 in yjiM or a complementary sequence thereof,
a sequence shown in SEQ ID NO: 17 in purT or a complementary sequence thereof,
a sequence shown in SEQ ID NO: 18 in dhaK1 or a complementary sequence thereof,
a sequence shown in SEQ ID NO: 19 in dhaK2 or a complementary sequence thereof,
a sequence shown in SEQ ID NO: 20 in dhaH or a complementary sequence thereof,
a sequence shown in SEQ ID NO: 21 in ptsH or a complementary sequence thereof,
a sequence shown in SEQ ID NO: 22 in ptsI or a complementary sequence thereof,
a sequence shown in SEQ ID NO: 23 in fsaA or a complementary sequence thereof,
a sequence shown in SEQ ID NO: 24 in ppk or a complementary sequence thereof,
a sequence shown in SEQ ID NO: 25 in aceF or a complementary sequence thereof,
a sequence shown in SEQ ID NO: 26 in cyoA or a complementary sequence thereof,
a sequence shown in SEQ ID NO: 30 in frdD or a complementary sequence thereof,
a sequence shown in SEQ ID NO: 31 in frdA or a complementary sequence thereof,
a sequence shown in SEQ ID NO: 32 in pgi or a complementary sequence thereof,
a sequence shown in SEQ ID NO: 33 in sdhA or a complementary sequence thereof,
a sequence shown in SEQ ID NO: 34 in sdhB or a complementary sequence thereof,
a sequence shown in SEQ ID NO: 35 in sdhC or a complementary sequence thereof,
a sequence shown in SEQ ID NO: 36 in sdhD or a complementary sequence thereof,
a sequence shown in SEQ ID NO: 38 in sucD or a complementary sequence thereof,
a sequence shown in SEQ ID NO: 39 in tnaA or a complementary sequence thereof,
a sequence shown in SEQ ID NO: 40 in glcF or a complementary sequence thereof,
a sequence shown in SEQ ID NO: 41 in glcE or a complementary sequence thereof,
a sequence shown in SEQ ID NO: 42 in yaeR or a complementary sequence thereof,
a sequence shown in SEQ ID NO: 43 in lsrC or a complementary sequence thereof,
a sequence shown in SEQ ID NO: 44 in hemN or a complementary sequence thereof,
a sequence shown in SEQ ID NO: 45 in agaW or a complementary sequence thereof,
a sequence shown in SEQ ID NO: 46 in gdhA or a complementary sequence thereof,
a sequence shown in SEQ ID NO: 47 in cyoB or a complementary sequence thereof,
a sequence shown in SEQ ID NO: 48 in rpiA or a complementary sequence thereof,
a sequence shown in SEQ ID NO: 49 in rpiB or a complementary sequence thereof,
a sequence shown in SEQ ID NO: 50 in lpdA or a complementary sequence thereof,
a sequence shown in SEQ ID NO: 51 in serC or a complementary sequence thereof,
a sequence shown in SEQ ID NO: 28 in serB or a complementary sequence thereof,
a sequence shown in SEQ ID NO: 29 in serA or a complementary sequence thereof,
a sequence shown in SEQ ID NO: 174 in zwf or a complementary sequence thereof,
a sequence shown in SEQ ID NO: 175 in pgl or a complementary sequence thereof,
a sequence shown in SEQ ID NO: 176 in gnd or a complementary sequence thereof,
a sequence shown in SEQ ID NO: 177 in rpe or a complementary sequence thereof,
a sequence shown in SEQ ID NO: 178 in talA or a complementary sequence thereof,
a sequence shown in SEQ ID NO: 179 in talB or a complementary sequence thereof,
a sequence shown in SEQ ID NO: 180 in tktA or a complementary sequence thereof,
a sequence shown in SEQ ID NO: 181 in tktB or a complementary sequence thereof,
a sequence shown in SEQ ID NO: 182 in ulaE or a complementary sequence thereof,
a sequence shown in SEQ ID NO: 183 in yieK or a complementary sequence thereof,
a sequence shown in SEQ ID NO: 184 in purH or a complementary sequence thereof,
a sequence shown in SEQ ID NO: 185 in pyrB or a complementary sequence thereof,
a sequence shown in SEQ ID NO: 186 in pyrI or a complementary sequence thereof,
a sequence shown in SEQ ID NO: 187 in cysQ or a complementary sequence thereof,
a sequence shown in SEQ ID NO: 188 in pyrC or a complementary sequence thereof,
a sequence shown in SEQ ID NO: 189 in gmk or a complementary sequence thereof,
a sequence shown in SEQ ID NO: 190 in guaA or a complementary sequence thereof,
a sequence shown in SEQ ID NO: 191 in guaB or a complementary sequence thereof,
a sequence shown in SEQ ID NO: 192 in ndk or a complementary sequence thereof,
a sequence shown in SEQ ID NO: 193 in pyrF or a complementary sequence thereof,
a sequence shown in SEQ ID NO: 194 in pyre or a complementary sequence thereof,
a sequence shown in SEQ ID NO: 195 in pyrH or a complementary sequence thereof, or
a sequence shown in SEQ ID NO: 196 in hpt or a complementary sequence thereof.
In another preferred embodiment, in (1) of the method, the target gene is selected from:

(a) a gene for nucleotide synthesis and other metabolism modules, lsrC, zwf, pgl, gnd, rpe, talA, talB, tktA, tktB, ulaE or yieK;

(b) a gene for pentose phosphate and glyoxylate pathway modules, rpiA, purH, pyrB, pyrI, cysQ, pyrC, gmk, guaA, guaB, ndk, pyrF, pyrE, pyrH or hpt;

(c) a gene for TCA cycle and oxidative phosphorylation modules, frdD, frdA, sdhA, sucC or sucD;

(d) a gene for carbohydrate metabolism module, ptsH, ptsI or glcE;

(e) a gene for 6-dEB precursor metabolism module, yjiM, ackA, pta or ybiW;

(f) a gene target for fatty acid metabolism module, fadB or dhaK2;

(g) a gene for amino acid and protein synthetic metabolism modules, serC; or (h) the combination of frdD+sucC, the combination of lsrC+frdD, the combination of lsrC+sucC, the combination of talA+guaB or the combination of zwf+guaB.

In another preferred embodiment, the interfering molecule that inhibits the expression of the target gene is sRNA.

In another preferred embodiment, the sRNA comprises the following structure:

a promoter, a target gene-inhibiting molecule (e.g., a target gene-binding sequence) and a terminator.

In another preferred embodiment, the promoter is selected from: Pr promoter (preferably, having the sequence of position 7 to position 61 in SEQ ID NO: 52), $P_{BAD}$ promoter, T7 promoter and Trc promoter.

In another preferred embodiment, the terminator is selected from: TE terminator (preferably, having the sequence of position 171 to position 310 in SEQ ID NO: 52), T1/TE terminator, T7 terminator, rrnB terminator, rrnB T1 and T2 terminators.

In another preferred embodiment, the following is also included between the interfering molecule that inhibits the expression of the target gene and the terminator: micF sequence (e.g., the sequence of position 110 to position 170 in SEQ ID NO: 52).

In another preferred embodiment, the target gene-inhibiting molecule is a short nucleic acid sequence, such as 18-26 bp in length; and preferably 20-24 bp; which can be complementary or bind to the mRNA of the target gene, or which has a stretch of the sequence of the mRNA of the target gene, wherein the stretch of the sequence can express a sequence that is complementary or binds to the mRNA of the target gene after being transferred into a cell.

In another preferred embodiment, the sRNA is included in an expression vector.

In another preferred embodiment, the host strain for synthesizing the polyketide 6-deoxyerythronolide is a prokaryotic bacterium capable of synthesizing the polyketide 6-deoxyerythronolide.

In another preferred embodiment, the prokaryotic bacterium capable of synthesizing the polyketide 6-deoxyerythronolide is E. coli capable of synthesizing the polyketide 6-deoxyerythronolide;

preferably, in the E. coli, the operon for propionic acid metabolism is knocked out and phosphopantetheinyl transferase gene sfp is integrated into the knockout site; or the operon for propionic acid metabolism is directly knocked out and sfp is integrated into any non-essential gene or a non-functional DNA sequence region in the genome of E. coli.

In another preferred embodiment, the E. coli is transformed with a gene encoding polyketide synthetase DEBS2 of Streptomyces erythreus, a gene encoding polyketide synthetase DEBS3 of Streptomyces erythreus, a gene encoding propionyl-CoA carboxylase β-CT subunit, a gene encoding propionyl-CoA carboxylase a-CT subunit and a gene encoding polyketide synthetase DEBS1 of Streptomyces erythreus.

In another aspect of the present invention, provided is an interfering molecule that inhibits the expression of a target gene, which is an sRNA comprising the following structure (preferably, the following is also included between the interfering molecule that inhibits the expression of the target gene and the terminator: micF sequence):

a promoter, a target gene-inhibiting molecule and a terminator.

In another aspect of the present invention, provided is use of the interfering molecule (e.g., sRNA) that inhibits the expression of a target gene, for transforming a host strain for synthesizing the polyketide 6-deoxyerythronolide, attenuating the corresponding target gene or promoting a host strain for synthesizing the polyketide 6-deoxyerythronolide to synthesize the polyketide 6-deoxyerythronolide biologically In another aspect of the present invention, provided is a host strain for synthesizing the polyketide 6-deoxyerythronolide, wherein the host strain is transformed with an interfering molecule that inhibits the expression of a target gene, or the host strain has the target gene knocked out; wherein, the target gene is selected from: (a) a gene for nucleotide synthesis and other metabolism modules, purT, lsrC, hemN, zwf, pgl, gnd, rpe, talA, talB, tktA, tktB, ulaE or yieK;

(b) a gene for pentose phosphate and glyoxylate pathway modules, yaeR, rpiA, rpiB, purH, pyrB, pyrI, cysQ, pyrC, gmk, guaA, guaB, ndk, pyrF, pyrE, pyrH or hpt;

(c) a gene for TCA cycle and oxidative phosphorylation modules, frdD, frdA, sdhA, sdhB, sdhC, sdhD, sucC, sucD, cyoA or cyoB;

(d) a gene for carbohydrate metabolism module, aceF, pgi, lpdA, ppk, ptsH, ptsI, glcF, glcE, fsaA or agaW;

(e) a gene for 6-dEB precursor metabolism module, yjiM, scpA, scpB, tdcD, tdcE, pflB, pflD, PaaF, ackA, pta or ybiW;

(f) a gene target for fatty acid metabolism module, fadJ, fadB, dhaK1, dhaK2 or dhaH;

(g) a gene for amino acid and protein synthetic metabolism modules, leuC, leuD, serC, serB, serA, gdhA or tnaA; or (h) the combination of frdD+sucC, the combination of lsrC+frdD, the combination of lsrC+sucC, the combination of frdD+rpiA, the combination of talA+guaB or the combination of zwf+guaB.

In another preferred embodiment, the host strain is transformed with the interfering molecule (e.g., sRNA) that inhibits the expression of the target gene; and/or the host strain for synthesizing the polyketide 6-deoxyerythronolide is a prokaryotic bacterium capable of synthesizing the polyketide 6-deoxyerythronolide; preferably, in the E. coli, the operon for propionic acid metabolism is knocked out and phosphopantetheinyl transferase gene sfp is integrated into the knockout site; and preferably, the E. coli is transformed with a gene encoding polyketide synthetase DEBS2 of Streptomyces erythreus, a gene encoding polyketide synthetase DEBS3 of Streptomyces erythreus, a gene encoding propionyl-CoA carboxylase β-CT subunit, a gene encoding propionyl-CoA carboxylase a-CT subunit and a gene encoding polyketide synthetase DEBS1 of Streptomyces erythreus.

In another aspect of the present invention, provided is a kit for promoting a host strain for synthesizing the polyketide 6-deoxyerythronolide to synthesize the polyketide 6-deoxyerythronolide biologically, the kit comprising: the sum of the host strains (from which one or more strains those skilled in the art can select for production); or the kit comprising: the sum of the interfering molecules that inhibit the expression of a target gene (from which one or more interfering molecules that inhibit the expression of the target gene those skilled in the art can select for application); or the kit comprising: the sum of vectors that respectively comprise the interfering molecule that inhibits the expression of a target gene (from which one or more vectors those skilled in the art can select for application).

Other aspects of the present invention will be apparent to those skilled in the art from the disclosure herein.

DETAILED DESCRIPTION OF EMBODIMENTS

Figure 1:
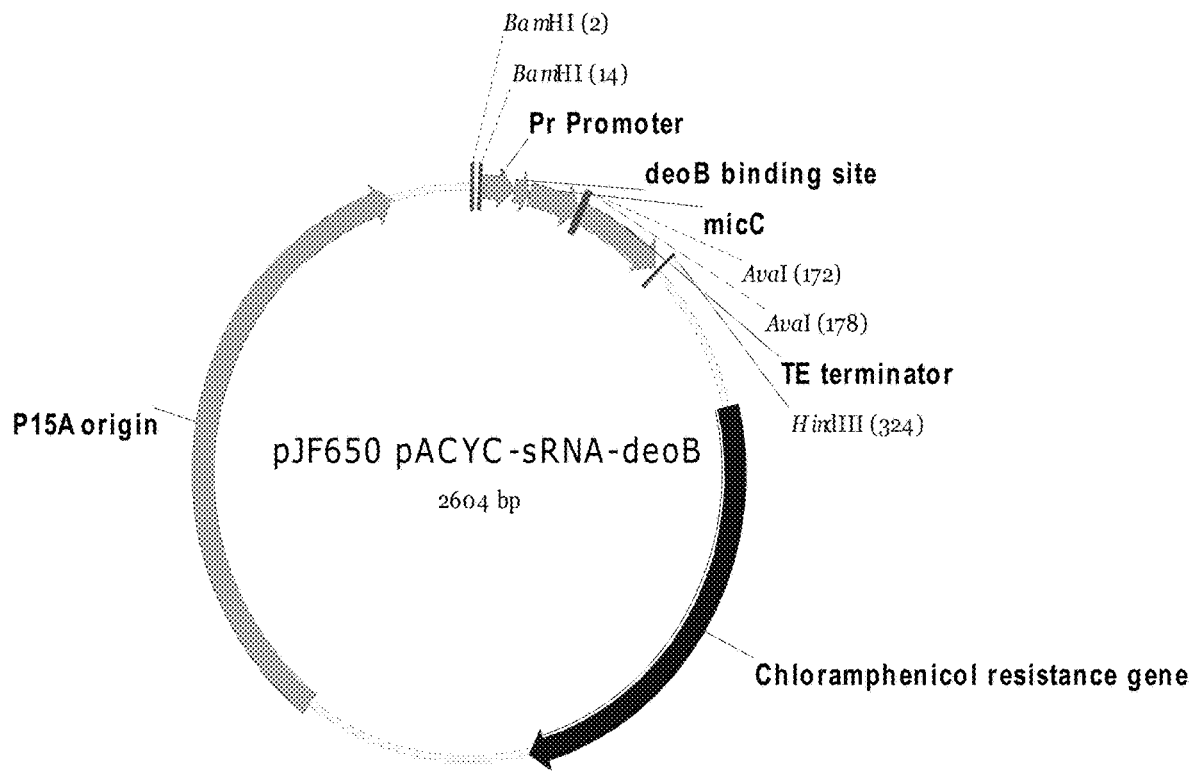
FIG. 1, a schematic diagram of sRNA-expressing plasmid PJF650.

After an in-depth research, the present inventors have first disclosed a method for promoting a host strain for synthesizing the polyketide 6-dEB to synthesize the polyketide 6-dEB biologically, by attenuating individually or in combination the expression of sucC (which expresses succinyl-CoA synthetase) and other genes in E. coli, to significantly increase the yield of the polyketide heterologously synthesized in E. coli, wherein the highest yield increase rate can reach 60% or more. The present method enables massive accumulation of the polyketide in the fermentation process.

As used herein, the "interfering molecule that inhibits the expression of a target gene" refers to an agent that can specifically reduce the expression level of the target gene, including a variety of molecules known in the art that can inhibit the expression of the target gene, such as, but not limited to, antisense nucleic acids, locked nucleic acids, peptide nucleic acids, siRNAs, shRNAs and microRNAs (collectively referred to as target gene-inhibiting molecules); or constructs that carry or express antisense nucleic acids, locked nucleic acids, peptide nucleic acids, siRNAs, shRNAs, microRNAs, etc.

As used herein, the "heterologous" refers to the relationship between two or more nucleic acids or protein sequences from different sources, or the relationship between a protein (or nucleic acid) and a host cell from different sources. For example, if the combination of a nucleic acid and a host cell is usually not naturally occurring, the nucleic acid is heterologous to the host cell. A particular sequence is "heterologous" to the cell or organism into which it is inserted.

As used herein, the "host strain for synthesizing the polyketide 6-dEB" refers to a host strain or host cell known in the art that can be applied to synthesize the polyketide 6-dEB. The host strain includes, but is not limited to, E. coli and improved E. coli (including strains transformed with pccB and pccA, strains transformed with eryAI, AII and/or AIII, etc.). Preferred host strain is E. coli which has its operon for propionic acid metabolism knocked out and phosphopantetheinyl transferase gene sfp integrated into the knockout site, and which is transformed with a gene encoding polyketide synthetase DEBS2 of Streptomyces erythreus, a gene encoding polyketide synthetase DEBS3 of Streptomyces erythreus, a gene encoding propionyl-CoA carboxylase β-CT subunit, a gene encoding propionyl-CoA carboxylase a-CT subunit and a gene encoding polyketide synthetase DEBS1 of Streptomyces erythreus.

In order to optimize the formation of the polyketide 6-dEB, the present inventors have made extensive studies to find a suitable target gene for improvement, down-regulation of the expression of which helps to promote the formation of 6-dEB. The various target genes disclosed in the present invention are genes known in the art, those skilled in the art can query the sequence information of these genes through GenBank and other platforms, and it is thus easy for those skilled in the art to obtain these genes.

The present invention also provides a set of genes, wherein the set of genes comprises: (a) a gene for nucleotide synthesis and other metabolism modules, purT, lsrC, hemN, zwf, pgl, gnd, rpe, talA, talB, tktA, tktB, ulaE or yieK; (b) a gene for pentose phosphate and glyoxylate pathway modules, yaeR, rpiA, rpiB, purH, pyrB, pyrI, cysQ, pyrC, gmk, guaA, guaB, ndk, pyrF, pyrE, pyrH or hpt; (c) a gene for TCA cycle and oxidative phosphorylation modules, frdD, frdA, sdhA, sdhB, sdhC, sdhD, sucC, sucD, cyoA or cyoB; (d) a gene for carbohydrate metabolism module, aceF, pgi, lpdA, ppk, ptsH, ptsI, glcF, glcE, fsaA or agaW; (e) a gene for 6-dEB precursor metabolism module, yjiM, scpA, scpB, tdcD, tdcE, pflB, pflD, PaaF, ackA, pta or ybiW; (f) a gene target for fatty acid metabolism module, fadJ, fadB, dhaK1, dhaK2 or dhaH; and (g) a gene for amino acid and protein synthetic metabolism modules, leuC, leuD, serC, serB, serA, gdhA or tnaA. Those skilled in the art, according to the present disclosure, may select one or more genes from the set of genes to carry out the operation of the method as described in the present invention and design a material for down-regulating its expression in a host cell on the basis of the selected target gene, thereby promoting the formation of 6-dEB.

As a preferred embodiment of the present invention, the interfering molecule that inhibits the interference of a target gene is sRNA or a construct (including expression vector) carrying the sRNA. Preferably, the sRNA comprises the following structure: a promoter, a target gene-inhibiting molecule (e.g., a target gene-binding sequence) and a terminator; and preferably, the following is also included between the target gene-inhibiting molecule and the terminator: micF sequence.

The design of the promoter and terminator may be carried out according to the experience of those skilled in the art, and any suitable promoter and terminator are encompassed within the scope of the present invention. As a preferred embodiment of the present invention, the promoter is Pr promoter, and the terminator is TE terminator. However, those skilled in the art may consider changing the promoter and terminator, which are still encompassed within the scope of the present invention.

Typically, the sRNA is located in an expression vector. Accordingly, the present invention also encompasses a vector comprising the sRNA. Generally, the expression vector also contains a replication origin and/or a marker gene, etc. Methods well known to those skilled in the art can be used to construct an expression vector required for the present invention. These methods include in vitro recombinant DNA technology, DNA synthesis technology, in vivo recombination technology, etc. It will be appreciated that any expression vector may be selected as long as the sRNA can be inserted and the expression of the target gene can be down-regulated after transforming a cell. In addition, the expression vector preferably comprises one or more selectable marker genes to provide a phenotypic trait for selecting a transformed host cell. Transformation of a host cell with an expression vector can be carried out using conventional techniques well known to those skilled in the art.

The present invention also provides a host strain for synthesizing the polyketide 6-dEB, wherein the host strain is transformed with an interfering molecule that inhibits the expression of a target gene. The host strain can efficiently produce the polyketide 6-dEB.

The present invention also provides a kit for promoting a host strain for synthesizing the polyketide 6-dEB to synthesize the polyketide 6-dEB biologically, the kit comprising: transformed with the sum of all the host strains for synthesizing the polyketide 6-dEB of the present invention (from which one or more strains those skilled in the art can select for production); and preferably, the kit comprising: transformed with the sum of the more preferred host strains for synthesizing the polyketide 6-dEB (host strains transformed with an interfering molecule that down-regulates the gene expression of the target gene or the target gene combination) of the present invention.

Or, the kit comprises: the sum of the sRNAs of the present invention (from which one or more sRNAs those skilled in the art can select for application); and preferably, the kit comprises: the sum of the more preferred sRNAs (sRNAs that down-regulate the gene expression of the target gene or the target gene combination) of the present invention.

The kit comprises: the sum of vectors that comprise the sRNA of the present invention (from which one or more vectors those skilled in the art can select for application); and preferably, the kit comprises: the sum of vectors that comprise the more preferred sRNAs (sRNAs that down-regulate the gene expression of the target gene or the target gene combination) of the present invention.

The present invention will be further illustrated with reference to specific examples below. It is to be understood that these examples are merely illustrative of the present invention and are not intended to limit the scope of the present invention. The experimental methods not specified for the specific conditions in the following examples are generally carried out in accordance with conventional conditions, such as the conditions described in J. Sambrook et al. (eds), Molecular Cloning: A Laboratory Manual, 3rd Edition, Science Press, 2002, or in accordance with the conditions recommended by the manufacturer.

The strains, culture media and related reagents used in the present invention were as follows.

The strain E. coli DH10B was used as the clone host, and the strain E. coli WG (pZG07/pZG08) was used as the host for synthesizing the polyketide 6-dEB (see, L U Zhiguo, Doctoral Dissertation of East China University of Science and Technology, 2011). The molecular cloning-related enzymes and kits for the extraction and purification of DNA fragments and plasmids were provided by NEB, TaKaRa and Axygen, respectively. The various medium components, antibiotics and other related reagents were purchased from Oxiod, Sinopharm Group and Shanghai Bioengineering Co., Ltd. The primers were synthesized by GenScript (Nanjing) Co., Ltd.

The formulation of the 6-dEB fermentation medium involved in the present invention was as follows (g/L): NaCl, 10; peptone, 10; yeast extract, 5; glycerin, 15; and 100 mM HEPES, with pH adjusted to 7.6. The inducers involved in the present invention were as follows: IPTG: 24 µg/ml; and precursor: sodium propionate 20 mM. The induction conditions involved in the present invention were as follows: 10 ml of culture medium charged in a 100 ml shake flask was fermented and cultured for 5 days at 22° C., 250 rpm.

The antibiotic concentrations involved in the present invention were ampicillin 100 mg/L, kanamycin 50 mg/L and chloramphenicol 34 mg/L, respectively.

Example 1

Construction of sRNA-Expressing Plasmids

The present invention regulated the expression of a target gene via sRNA interference technology, that is, an sRNA was expressed to bind to the mRNA of the target gene, thereby inhibiting the binding of the mRNA of the target gene to the ribosome and then inhibiting the expression of the target gene. In the present invention, a target gene conducive to improving the synthesis of a polyketide was identified by attenuating the selected gene target.

A deoB-sRNA gene sequence fragment synthesized chemically (synthesize by Shanghai Jieduan Bioengineering Co., Ltd.) comprised Pr promoter, deoB target gene-binding site (the DNA sequence is 24 bp in length, caccataataaatgcacgtttcat (SEQ ID NO: 1); completely complementary to 24 bp starting from the ATG initiating sequence of the pentose phosphate mutase deoB gene, Genbank No. of the deoB gene: NC_012971.2), micF sequence (Genbank No.: NC_000913.3) and TE terminator, and digestion sites NdeI and HindIII were introduced at both ends. The DNA sequence of this sRNA gene sequence fragment was as follows (SEQ ID NO: 52):

<u>catatg</u>ggatcctaacaccgtgcgtgttgactattttacctctggcggtgataatg gttgccaccataataaatgc acgtttcattttctgttgggccattgcattgccactgat- tttccaacatataaaaagacaagcccgaacagtcgtccgggctt ttttctcgagctcgagccaggcatcaaataaaacgaaaggctcagtcgaaa- gactgggcctttcgttttatctgttttgtc ggtgaacgctctctactagagt- cacactggctcaccttcgggtgggcctttctgcgtttataactagtagatct<u>aagctt</u>

In the construction of an sRNA-expressing plasmid, the pACYCDuet-1 plasmid (purchased from Novagen) was used as the PCR template, a vector fragment only containing chloramphenicol resistance and p15A replicon was obtained by cloning with primers pACYC-F and pACYC-R (digestion sites NdeI and HindIII were introduced at both ends of the primers), and this vector fragment was double digested with NdeI and HindIII after recovering with a cleaning and recovering kit (purchased from Axygen); and the above deoB-sRNA sequence fragment synthesized chemically was double digested with NdeI and HindIII at the same time. The double-digested vector fragment and deoB-sRNA fragment were directly recovered with the cleaning and recovering kit, and the two recovered fragments were then ligated with T4 ligase to obtain template plasmid pJF650 (FIG. 1), for attenuating the expression of the deoB gene in E. coli.

Using template plasmid pJF650 as the template together with the primers in Table 1 and the PCR conditions in Table 2, sRNA plasmid libraries were directly obtained by site-directed mutagenesis PCR amplification that were capable of attenuating the expression of different target genes as follows in E. coli: (1) genes for TCA cycle and oxidative phosphorylation modules, frdD, frdA, sdhA, sdhB, sdhC, sdhD, sucC, sucD, cyoA and cyoB; (2) genes for carbohydrate metabolism module, aceF, pgi, lpdA, ppk, ptsH, ptsI, glcF, glcE, fsaA and agaW; (3) genes for 6-dEB precursor metabolism module, yjiM, scpA, scpB, tdcD, tdcE, pflB, pflD, PaaF, ackA, pta and ybiW; (4) genes for pentose phosphate and glyoxylate pathway modules, yaeR, rpiA, rpiB, purH, pyrB, pyrI, cysQ, pyrC, gmk, guaA, guaB, ndk, pyrF, pyrE, pyrH and hpt; (5) gene targets for fatty acid metabolism module, fadJ, fadB, dhaK1, dhaK2 and dhaH; (6) genes for amino acid and protein synthetic metabolism modules, leuC, leuD, serC, serB, serA, gdhA and tnaA; and (7) genes for nucleotide synthesis and other metabolism modules, purT, lsrC, hemN, zwf, pgl, gnd, rpe, talA, talB, tktA, tktB, ulaE and yieK; wherein the sRNA plasmid libraries were pSJ01 (target gene tdcD), pSJ02 (target gene scpB), pSJ03 (target gene scpA), pSJ04 (target gene ybiW), pSJ05 (target gene pflB), pSJ06 (target gene tdcE), pSJ07 (target gene pflD), pSJ08 (target gene paaF), pSJ09 (target gene fadJ), pSJ10 (target gene fadB), pSJ11 (target gene ackA), pSJ12 (target gene pta), pSJ13 (target gene leuD), pSJ14 (target gene leuC), pSJ15 (target gene yjiM), pSJ16 (target gene purT), pSJ17 (target gene dhaK1), pSJ18 (target gene dhaK2), pSJ19 (target gene dhaH), pSJ20 (target gene ptsH), pSJ21 (target gene ptsI), pSJ22 (target gene fsaA), pSJ24 (target gene ppk), pSJ26 (target gene aceF), pSJ29 (target gene cyoA), pSJ30 (target gene frdD), pSJ33 (target gene frdA), pSJ34 (target gene pgi), pSJ35 (target gene sdhA), pSJ36 (target gene sdhB), pSJ37 (target gene sdhC), pSJ38 (target gene sdhD), pSJ39 (target gene sucC), pSJ40 (target gene sucD), pSJ41 (target gene tnaA), pSJ43 (target gene glcF), pSJ44 (target gene gleE), pSJ50 (target gene yaeR), pSJ53 (target gene lsrC), pSJ54 (target gene hemN), pSJ66 (target gene agaW), pJF663 (target gene zwf), pJF666 (target gene pgl), pJF670 (target gene gnd), pSJ128 (target gene rpe), pSJ129 (target gene talA), pSJ130 (target gene talB), pSJ131 (target gene tktA), pSJ132 (target gene tktB), pSJ133 (target gene ulaE), pSJ141 (target gene yieK), pSJ147 (target gene purH), pSJ148 (target gene pyrB), pSJ149 (target gene pyrI), pSJ150 (target gene cysQ), pSJ151 (target gene pyrC), pSJ152 (target gene gmk), pSJ153 (target gene guaA), pSJ154 (target gene guaB), pSJ155 (target gene ndk), pSJ156 (target gene pyrF), pSJ157 (target gene pyrE), pSJ158 (target gene pyrH), pSJ159 (target gene hpt), pJF656 (target gene gdhA), pJF664 (target gene cyoB), pJF667 (target gene rpiA), pJF668 (target gene rpiB), pJF671 (target gene lpdA), pJF672 (target gene serC), pJF673 (target gene serB) and pJF674 (target gene serA) (Table 3). Taking the construction of an sRNA plasmid for attenuating the target gene sucC (which expresses succinyl-CoA synthetase) as an example, the deoB target gene-binding site with a length of 24 bp in the skeleton of the pJF650 plasmid was directly mutated into sucC target gene-binding site (completely complementary to the DNA sequence with a length of 24 bp starting from the ATG initiating sequence of the sucC gene) by site-directed mutagenesis PCR using template plasmid pJF650 as the template together with the sucC-sRNA-F and sucC-sRNA-R primers in Table 1 and the PCR conditions in Table 2, obtaining sRNA plasmid pSJ39 that is capable of attenuating the expression of the sucC gene.

TABLE 1

Primers for plasmid construction

| Constructed plasmid name | Primer name | Primer sequence (from 5' to 3') | Primer SEQ ID NO: | Target gene-binding sequence (SEQ ID NO:) |
|---|---|---|---|---|
| pJF650 | pACYC-F | CCCAAGCTTCTGAAACCTCAGGCATTTGA | 53 | |
| | pACYC-R | CGGGATCCGCGCAACGCAATTAATGTAA | 54 | |
| pSJ01 | scpB-sRNA-F | aacgttaacatactgataagacatTTTCTGTTGGGCCATTGCATTGCC | 55 | targeting scpB Aacgttaacatactgata agacat (2) |
| | scpB-sRNA-R | atgtcttatcagtatgttaacgttGCAACCATTATCACCGCCAGAGGTA | 56 | |
| pSJ02 | tdcD-sRNA-F | caaaacaaccggaaattcattcatTTTCTGTTGGGCCATTGCATTGCC | 57 | targeting tdcD Caaaacaaccggaaatt cattcat (3) |
| | tdcD-sRNA-R | atgaatgaatttccggttgttttgGCAACCATTATCACCGCCAGAGGTA | 58 | |
| pSJ03 | scpA-sRNA-F | ttgccactcctgcacgttagacatTTTCTGTTGGGCCATTGCATTGCC | 59 | targeting scpA: Ttgccactcctgcacgtt agacat (4) |
| | scpA-sRNA-R | atgtctaacgtgcaggagtggcaaGCAACCATTATCACCGCCAGAGGTA | 60 | |
| pSJ04 | ybiW-sRNA-F | cgtgtccagtttcagtgtggtcatTTTCTGTTGGGCCATTGCATTGCC | 61 | targeting ybiW: Cgtgtccagtttcagtgt ggtcat (5) |
| | ybiW-sRNA-R | atgaccacactgaaactggacacgGCAACCATTATCACCGCCAGAGGTA | 62 | |
| pSJ05 | pflB-sRNA-F | taacttttcattaagctcggacatTTTCTGTTGGGCCATTGCATTGCC | 63 | targeting pflB: Taacttttcattaagctcg gacat (6) |
| | pflB-sRNA-R | atgtccgagcttaatgaaaagttaGCAACCATTATCACCGCCAGAGGTA | 64 | |
| pSJ06 | tdcE-sRNA-F | gctggtatcaatatctaccttcatTTTCTGTTGGGCCATTGCATTGCC | 65 | targeting tdcE: Gctggtatcaatatctac cttcat (7) |
| | tdcE-sRNA-R | atgaaggtagatattgataccagcGCAACCATTATCACCGCCAGAGGTA | 66 | |

TABLE 1-continued

Primers for plasmid construction

| Constructed plasmid name | Primer name | Primer sequence (from 5' to 3') | Primer SEQ ID NO: | Target gene-binding sequence (SEQ ID NO:) |
|---|---|---|---|---|
| pSJ07 | pflD-sRNA-F | gaggcgagagatacgattcgtcatTTTCTGTTGGGCCATTGCATTGCC | 67 | targeting pflD: Gaggcgagagatacgattcgtcat (8) |
|  | pflD-sRNA-R | atgacgaatcgtatctctcgcctcGCAACCATTATCACCGCCAGAGGTA | 68 | |
| pSJ08 | paaF-sRNA-F | acggctgacgatcagttcgctcatTTTCTGTTGGGCCATTGCATTGCC | 69 | targeting paaF: Acggctgacgatcagttcgctcat (9) |
|  | paaF-sRNA-R | atgagcgaactgatcgtcagccgtGCAACCATTATCACCGCCAGAGGTA | 70 | |
| pSJ09 | fadJ-sRNA-F | ggtaaacgctgatgtcatttccatTTTCTGTTGGGCCATTGCATTGCC | 71 | targeting fadJ: Ggtaaacgctgatgtcatttccat (10) |
|  | fadJ-sRNA-R | atggaaatgacatcagcgtttaccGCAACCATTATCACCGCCAGAGGTA | 72 | |
| pSJ10 | fadB-sRNA-F | cagggtgtcgcctttgtaaagcatTTTCTGTTGGGCCATTGCATTGCC | 73 | targeting fadB: Cagggtgtcgcctttgtaaagcat (11) |
|  | fadB-sRNA-R | atgctttacaaaggcgacaccctgGCAACCATTATCACCGCCAGAGGTA | 74 | |
| pSJ11 | ackA-sRNA-F | aaccagtactaacttactcgacatTTTCTGTTGGGCCATTGCATTGCC | 75 | targeting ackA: Aaccagtactaacttactcgacat (12) |
|  | ackA-sRNA-R | atgtcgagtaagttagtactggttGCAACCATTATCACCGCCAGAGGTA | 76 | |
| pSJ12 | pta-sRNA-F | gatcagcataataatacgggacacTTTCTGTTGGGCCATTGCATTGCC | 77 | targeting pta: Gatcagcataataatacgggacac (13) |
|  | pta-sRNA-R | gtgtcccgtattattatgctgatcGCAACCATTATCACCGCCAGAGGTA | 78 | |
| pSJ13 | leuD-sRNA-F | gtgtttgataaatttctctgccatTTTCTGTTGGGCCATTGCATTGCC | 79 | targeting leuD: Gtgtttgataaatttctctgccat (14) |
|  | leuD-sRNA-R | atggcagagaaatttatcaaacacGCAACCATTATCACCGCCAGAGGTA | 80 | |
| pSJ14 | leuC-sRNA-F | tttttcgtataacgtcttagccatTTTCTGTTGGGCCATTGCATTGCC | 81 | targeting leuC: Tttttcgtataacgtcttagccat (15) |
|  | leuC-sRNA-R | atggctaagacgttatacgaaaaaGCAACCATTATCACCGCCAGAGGTA | 82 | |
| pSJ15 | yjiM-sRNA-F | gggtagatcggtgacaagtgacatTTTCTGTTGGGCCATTGCATTGCC | 83 | targeting yjiM: Gggtagatcggtgacaagtgacat (16) |
|  | yjiM-sRNA-R | atgtcacttgtcaccgatctaccCGCAACCATTATCACCGCCAGAGGTA | 84 | |
| pSJ16 | purT-sRNA-F | cagcgcagtgcctaataacgtcatTTTCTGTTGGGCCATTGCATTGCC | 85 | targeting purT: Cagcgcagtgcctaataacgtcat (17) |
|  | purT-sRNA-R | atgacgttattaggcactgcgctgGCAACCATTATCACCGCCAGAGGTA | 86 | |
| pSJ17 | dhaK1-sRNA-F | cacatcattgatcaattttttcatTTTCTGTTGGGCCATTGCATTGCC | 87 | targeting dhaK1: Cacatcattgatcaatttttcat (18) |
|  | dhaK1-sRNA-R | atgaaaaaattgatcaatgatgtgGCAACCATTATCACCGCCAGAGGTA | 88 | |
| pSJ18 | dhaK2-sRNA-F | aatttgagttctgctcagtgacatTTTCTGTTGGGCCATTGCATTGCC | 89 | targeting dhaK2 Aatttgagttctgctcagtgacat (19) |
|  | dhaK2-sRNA-R | atgtcactgagcagaactcaaattGCAACCATTATCACCGCCAGAGGTA | 90 | |
| pSJ19 | dhaH-sRNA-F | tgaaactatgaccaggttaccatTTTCTGTTGGGCCATTGCATTGCC | 91 | targeting dhaH: Tgaaactatgaccaggttaccat (20) |
|  | dhaH-sRNA-R | atggtaaacctggtcatagtttcaGCAACCATTATCACCGCCAGAGGTA | 92 | |
| pSJ20 | ptsH-sRNA-F | aatggtaacttcttgctggaacatTTTCTGTTGGGCCATTGCATTGCC | 93 | targeting ptsH: Aatggtaacttcttgctggaacat (21) |
|  | ptsH-sRNA-R | atgttccagcaagaagttaccattGCAACCATTATCACCGCCAGAGGTA | 94 | |
| pSJ21 | ptsI-sRNA-F | ggatgctaaaatgcctgaaatcatTTTCTGTTGGGCCATTGCATTGCC | 95 | targeting ptsI: Ggatgctaaaatgcctg |

TABLE 1-continued

Primers for plasmid construction

| Constructed plasmid name | Primer name | Primer sequence (from 5' to 3') | Primer SEQ ID NO: | Target gene-binding sequence (SEQ ID NO:) |
|---|---|---|---|---|
| | ptsI-sRNA-R | atgatttcaggcattttagcatccGCAACCATTATCACCGCCAGAGGTA | 96 | aaatcat (22) |
| pSJ22 | fsaA-sRNA-F | tgaagtatccagatacagttccatTTTCTGTTGGGCCATTGCATTGCC | 97 | targeting fsaA: Tgaagtatccagataca |
| | fsaA-sRNA-R | atggaactgtatctggatacttcaGCAACCATTATCACCGCCAGAGGTA | 98 | gttccat (23) |
| pSJ24 | ppk-sRNA-F | gatgtatagcttttcctgacccatTTTCTGTTGGGCCATTGCATTGCC | 99 | targeting ppk: Gatgtatagcttttcctga |
| | ppk-sRNA-R | atgggtcaggaaaagctatacatcGCAACCATTATCACCGCCAGAGGTA | 100 | cccat (24) |
| pSJ26 | aceF-sRNA-F | cggtactttgatttcgatagccatTTTCTGTTGGGCCATTGCATTGCC | 101 | targeting aceF: Cggtactttgatttcgata |
| | aceF-sRNA-R | atggctatcgaaatcaaagtaccgGCAACCATTATCACCGCCAGAGGTA | 102 | gccat (25) |
| pSJ29 | cyoA-sRNA-F | tttattgtatttcctgagtctcatTTTCTGTTGGGCCATTGCATTGCC | 103 | targeting cyoA: Tttattgtatttcctgagtc |
| | cyoA-sRNA-R | atgagactcaggaaatacaataaaGCAACCATTATCACCGCCAGAGGTA | 104 | tcat (26) |
| pSJ30 | frdD-sRNA-F | acgctttggatttggattaatcatTTTCTGTTGGGCCATTGCATTGCC | 105 | targeting frdD: Acgctttggatttggatta |
| | frdD-sRNA-R | atgattaatccaaatccaaagcgtGCAACCATTATCACCGCCAGAGGTA | 106 | atcat (30) |
| pSJ33 | frdA-sRNA-F | aagatcggcttgaaaggtttgcacTTTCTGTTGGGCCATTGCATTGCC | 107 | targeting frdA: Aagatcggcttgaaagg |
| | frdA-sRNA-R | gtgcaaacctttcaagccgatcttGCAACCATTATCACCGCCAGAGGTA | 108 | tttgcac (31) |
| pSJ34 | pgi-sRNA-F | ctgcgttggattgatgttttcatTTTCTGTTGGGCCATTGCATTGCC | 109 | targeting pgi: Ctgcgttggattgatgttt |
| | pgi-sRNA-R | atgaaaaacatcaatccaacgcagGCAACCATTATCACCGCCAGAGGTA | 110 | tcat (32) |
| pSJ35 | sdhA-sRNA-F | aaattctctgactggcaatttcatTTTCTGTTGGGCCATTGCATTGCC | 111 | targeting sdhA: Aaattctctgactggcaa |
| | sdhA-sRNA-R | atgaaattgccagtcagagaatttGCAACCATTATCACCGCCAGAGGTA | 112 | tttcat (33) |
| pSJ36 | sdhB-sRNA-F | ataaattgaaaactcgagtctcatTTTCTGTTGGGCCATTGCATTGCC | 113 | targeting sdhB: Ataaattgaaaactcgag |
| | sdhB-sRNA-R | atgagactcgagttttcaattatGCAACCATTATCACCGCCAGAGGTA | 114 | tctcat (34) |
| pSJ37 | sdhC-sRNA-F | ttgttttttcacatttcttatcatTTTCTGTTGGGCCATTGCATTGCC | 115 | targeting sdhC: Ttgttttttcacatttcttat |
| | sdhC-sRNA-R | atgataagaaatgtgaaaaaacaaGCAACCATTATCACCGCCAGAGGTA | 116 | cat (35) |
| pSJ38 | sdhD-sRNA-F | taatgcggaggcgttgcttaccatTTTCTGTTGGGCCATTGCATTGCC | 117 | targeting sdhD: Taatgcggaggcgttgc |
| | sdhD-sRNA-R | atggtaagcaacgcctccgcattaGCAACCATTATCACCGCCAGAGGTA | 118 | ttaccat (36) |
| pSJ39 | sucC-sRNA-F | tgcctgatattcatgtaagttcatTTTCTGTTGGGCCATTGCATTGCC | 119 | targeting sucC: Tgcctgatattcatgtaa |
| | sucC-sRNA-R | atgaacttacatgaatatcaggcaGCAACCATTATCACCGCCAGAGGTA | 120 | gttcat (37) |
| pSJ40 | sucD-sRNA-F | gtttttatcgattaaaatggacatTTTCTGTTGGGCCATTGCATTGCC | 121 | targeting sucD: Gtttttatcgattaaaatg |
| | sucD-sRNA-R | atgtccattttaatcgataaaaacGCAACCATTATCACCGCCAGAGGTA | 122 | gacat (38) |
| pSJ41 | tnaA-sRNA-F | agggagatgtttaaagttttccatTTTCTGTTGGGCCATTGCATTGCC | 123 | targeting tnaA: Agggagatgtttaaagtt |
| | tnaA-sRNA-R | atgaaaactttaaacatctccctGCAACCATTATCACCGCCAGAGGTA | 124 | ttccat (39) |

TABLE 1-continued

Primers for plasmid construction

| Constructed plasmid name | Primer name | Primer sequence (from 5' to 3') | Primer SEQ ID NO: | Target gene-binding sequence (SEQ ID NO:) |
|---|---|---|---|---|
| pSJ43 | glcF-sRNA-F | ctcttcagttaattgggtttgcatTTTCTGTTGGGCCATTGCATTGCC | 125 | targeting glcF: Ctcttcagttaattgggttt gcat (40) |
|  | glcF-sRNA-R | atgcaaacccaattaactgaagagGCAACCATTATCACCGCCAGAGGTA | 126 | |
| pSJ44 | glcE-sRNA-F | gctgtaatcacactcgcgtagcatTTTCTGTTGGGCCATTGCATTGCC | 127 | targeting glcE: Gctgtaatcacactcgcg tagcat (41) |
|  | glcE-sRNA-R | atgctacgcgagtgtgattacagcGCAACCATTATCACCGCCAGAGGTA | 128 | |
| pSJ50 | yaeR-sRNA-F | gtgaacctgttttaaacccagcatTTTCTGTTGGGCCATTGCATTGCC | 129 | targeting yaeR: Gtgaacctgttttaaacc cagcat (42) |
|  | yaeR-sRNA-R | atgctgggtttaaaacaggttcacGCAACCATTATCACCGCCAGAGGTA | 130 | |
| pSJ53 | lsrC-sRNA-F | gttgttctgaataaacttcagcatTTTCTGTTGGGCCATTGCATTGCC | 131 | targeting lsrC: Gttgttctgaataaacttc agcat (43) |
|  | lsrC-sRNA-R | atgctgaagtttattcagaacaacGCAACCATTATCACCGCCAGAGGTA | 132 | |
| pSJ54 | hemN-sRNA-F | ccagtcgatttgctgtacagacatTTTCTGTTGGGCCATTGCATTGCC | 133 | targeting hemN: Ccagtcgatttgctgtac agacat (44) |
|  | hemN-sRNA-R | atgtctgtacagcaaatcgactggGCAACCATTATCACCGCCAGAGGTA | 134 | |
| pSJ66 | agaW-sRNA-F | tgcctgcaacaggctgatttccatTTTCTGTTGGGCCATTGCATTGCC | 135 | targeting agaW: Tgcctgcaacaggctga tttccat (45) |
|  | agaW-sRNA-R | atggaaatcagcctgttgcaggcaGCAACCATTATCACCGCCAGAGGTA | 136 | |
| pJF656 | gdhA-F | ctccagagaatatgtctgatccatTTTCTGTTGGGCCATTGCAT | 137 | targeting gdhA: Ctccagagaatatgtctg atccat (46) |
|  | gdhA-R | ATGGATCAGACATATTCTCTGGAGGCAACCATTATCACCGCCAG | 138 | |
| pJF664 | cyoB-F | ATCAAGTGATAATTTTCCGAACATTTTCTGTTGGGCCATTGCAT | 140 | targeting cyoB: Atgttcggaaaattatca cttgat (47) |
|  | cyoB-B | atgttcggaaaattatcacttgatGCAACCATTATCACCGCCAG | 141 | |
| pJF667 | rpiA-F | tttttcaattcatcctgcgtcatTTTCTGTTGGGCCATTGCAT | 142 | targeting rpiA: Tttttcaattcatcctgcg tcat (48) |
|  | rpiA-R | ATGACGCAGGATGAATTGAAAAAGCAACCATTATCACCGCCAG | 143 | |
| pJF668 | rpiB-F | acagccaaatgcaatcttttttcatTTTCTGTTGGGCCATTGCAT | 144 | targeting rpiB: Acagccaaatgcaatctt tttcat (49) |
|  | rpiB-R | ATGAAAAAGATTGCATTTGGCTGTGCAACCATTATCACCGCCAG | 145 | |
| pJF671 | lpdA-F | ctgagttttgatttcagtactcatTTTCTGTTGGGCCATTGCAT | 146 | targeting lpdA: Ctgagttttgatttcagta ctcat (50) |
|  | lpdA-R | ATGAGTACTGAAATCAAAACTCAGGCAACCATTATCACCGCCAG | 147 | |
| pJF672 | serC-F | actaaaattgaagatttgagccatTTTCTGTTGGGCCATTGCAT | 148 | targeting serC: Actaaaattgaagatttg agccat (51) |
|  | serC-R | ATGGCTCAAATCTTCAATTTTAGTGCAACCATTATCACCGCCAG | 149 | |
| pJF673 | serB-F | gtcgcaccaggtaatgttaggcatTTTCTGTTGGGCCATTGCAT | 150 | targeting serB: Gtcgcaccaggtaatgtt aggcat (28) |
|  | serB-R | ATGCCTAACATTACCTGGTGCGACGCAACCATTATCACCGCCAG | 151 | |
| pJF674 | serA-F | tttctccagcgatacctttgccatTTTCTGTTGGGCCATTGCAT | 152 | targeting serA: Tttctccagcgatacctttt gccat (29) |
|  | serA-R | ATGGCAAAGGTATCGCTGGAGAAAGCAACCATTATCACCGCCAG | 153 | |
| pJF663 | zwf-sRNA-R | ctgggctgtttgcgttaccgccatTTTCTGTTGGGCCATTGCAT | 197 | targeting zwf: Ctgggctgtttgcgttac |

TABLE 1-continued

Primers for plasmid construction

| Constructed plasmid name | Primer name | Primer sequence (from 5' to 3') | Primer SEQ ID NO: | Target gene-binding sequence (SEQ ID NO:) |
|---|---|---|---|---|
| | zwf-sRNA-R | atggcggtaacgcaaacagcccagGCAACCATTATCACCGCCAG | 198 | cgccat (174) |
| pJF666 | pgl-sRNA-F | ggcgatataaactgtttgcttcatTTTCTGTTGGGCCATTGCAT | 199 | targeting pgl: Ggcgatataaactgtttg cttcat (175) |
| | pgl-sRNA-F | ATGAAGCAAACAGTTTATATCGCCGCAACCATTATCACCGCCAG | 200 | |
| pJF670 | gnd-sRNA-F | tacgccgatctgttgcttggacatTTTCTGTTGGGCCATTGCAT | 201 | targeting gnd: tacgccgatctgttgcttg gacat (176) |
| | gndsRNA-F | ATGTCCAAGCAACAGATCGGCGTAGCAACCATTATCACCGCCAG | 202 | |
| pSJ128 | rpe-sRNA-F | gggggcaatcaaatactgtttcatTTTCTGTTGGGCCATTGCATTGCC | 203 | targeting rpe: gggggcaatcaaatact gtttcat (177) |
| | rpe-sRNA-R | atgaaacagtatttgattgccccGCAACCATTATCACCGCCAGAGGTA | 204 | |
| pSJ129 | talA-sRNA-F | tttgatgccgtctaactcgttcatTTTCTGTTGGGCCATTGCATTGCC | 205 | targeting talA: tttgatgccgtctaactcgt tcat (178) |
| | talA-sRNA-R | atgaacgagttagacggcatcaaaGCAACCATTATCACCGCCAGAGGTA | 206 | |
| pSJ130 | talB-sRNA-F | aagggaggtcaatttgtccgtcatTTTCTGTTGGGCCATTGCATTGCC | 207 | targeting talB: aagggaggtcaatttgtc cgtcat (179) |
| | talB-sRNA-R | atgacggacaaattgacctcccttGCAACCATTATCACCGCCAGAGGTA | 208 | |
| pSJ131 | tktA-sRNA-F | ggcaagctcttacgtgaggacatTTTCTGTTGGGCCATTGCATTGCC | 209 | targeting tktA: Ggcaagctctttacgtga ggacat (180) |
| | tktA-sRNA-R | atgtcctcacgtaaagagcttgccGCAACCATTATCACCGCCAGAGGTA | 210 | |
| pSJ132 | tktB-sRNA-F | attggcaaggtctttcgggacatTTTCTGTTGGGCCATTGCATTGCC | 211 | targeting tktB: attggcaaggtcttttcgg gacat (181) |
| | tktB-sRNA-R | atgtcccgaaaagaccttgccaatGCAACCATTATCACCGCCAGAGGTA | 212 | |
| pSJ133 | ulaE-sRNA-F | aagcgggatttgtttggacaacatTTTCTGTTGGGCCATTGCATTGCC | 213 | targeting ulaE: aagcgggatttgtttgga caacat (182) |
| | ulaE-sRNA-R | atgttgtccaaacaaatcccgcttGCAACCATTATCACCGCCAGAGGTA | 214 | |
| pSJ141 | yieK-sRNA-F | atcttcggtaatgattaatttcatTTTCTGTTGGGCCATTGCATTGCC | 215 | targeting yieK: atcttcggtaatgattaatt tcat (183) |
| | yieK-sRNA-R | atgaaattaatcattaccgaagatGCAACCATTATCACCGCCAGAGGTA | 216 | |
| pSJ147 | purH-sRNA-F | gcggactggacgacgttgttgcatTTTCTGTTGGGCCATTGCATTGCC | 217 | targeting purH: gcggactggacgacgtt gttgcat (184) |
| | purH-sRNA-R | atgcaacaacgtcgtccagtccgcGCAACCATTATCACCGCCAGAGGTA | 218 | |
| pSJ148 | pyrB-sRNA-F | tttctgatatagcggattagccatTTTCTGTTGGGCCATTGCATTGCC | 219 | targeting pyrB: tttctgatatagcggatta gccat (185) |
| | pyrB-sRNA-R | atggctaatccgctatatcagaaaGCAACCATTATCACCGCCAGAGGTA | 220 | |
| pSJ149 | pyrI-sRNA-F | ctgcaatttattatcgtgtgtcatTTTCTGTTGGGCCATTGCATTGCC | 221 | targeting pyrI: ctgcaatttattatcgtgtg tcat (186) |
| | pyrI-sRNA-R | atgacacacgataataaattgcagGCAACCATTATCACCGCCAGAGGTA | 222 | |
| pSJ150 | cysQ-sRNA-F | aagctggcatacttgatctaacatTTTCTGTTGGGCCATTGCATTGCC | 223 | targeting cysQ: aagctggcatacttgatct aacat (187) |
| | cysQ-sRNA-R | atgttagatcaagtatgccagcttGCAACCATTATCACCGCCAGAGGTA | 224 | |
| pSJ151 | pyrC-sRNA-F | taatacctgggatggtgcagtcatTTTCTGTTGGGCCATTGCATTGCC | 225 | targeting pyrC: taatacctgggatggtgc agtcat (188) |
| | pyrC-sRNA-R | atgactgcaccatcccaggtattaGCAACCATTATCACCGCCAGAGGTA | 226 | |

TABLE 1-continued

Primers for plasmid construction

| Constructed plasmid name | Primer name | Primer sequence (from 5' to 3') | Primer SEQ ID NO: | Target gene-binding sequence (SEQ ID NO:) |
|---|---|---|---|---|
| pSJ152 | gmk-sRNA-F | aatataaagcgtgccttgagccatTTTCTGTTGGGCCATTGCATTGCC | 227 | targeting gmk: aatataaagcgtgccttgagccat (189) |
| | gmk-sRNA-R | atggctcaaggcacgctttatattGCAACCATTATCACCGCCAGAGGTA | 228 | |
| pSJ153 | guaA-sRNA-F | atgcttatgaatgttttccgtcatTTTCTGTTGGGCCATTGCATTGCC | 229 | targeting guaA: atgcttatgaatgttttccgtcat (190) |
| | guaA-sRNA-R | atgacggaaaacattcataagcatGCAACCATTATCACCGCCAGAGGTA | 230 | |
| pSJ154 | guaB-sRNA-F | agcttctttagcgatacgtagcatTTTCTGTTGGGCCATTGCATTGCC | 231 | targeting guaB: agcttctttagcgatacgtagcat (191) |
| | guaB-sRNA-R | atgctacgtatcgctaaagaagctGCAACCATTATCACCGCCAGAGGTA | 232 | |
| pSJ155 | ndk-sRNA-F | ggaaaaagtacgttcaatagccatTTTCTGTTGGGCCATTGCATTGCC | 233 | targeting ndk: ggaaaaagtacgttcaatagccat (192) |
| | ndk-sRNA-R | atggctattgaacgtacttttccGCAACCATTATCACCGCCAGAGGTA | 234 | |
| pSJ156 | pyrF-sRNA-F | agaagatgaagcagttaacgtcatTTTCTGTTGGGCCATTGCATTGCC | 235 | targeting pyrF: agaagatgaagcagttaacgtcat (193) |
| | pyrF-sRNA-R | atgacgttaactgcttcatcttctGCAACCATTATCACCGCCAGAGGTA | 236 | |
| pSJ157 | pyrE-sRNA-F | aaactggcgctgatatggtttcatTTTCTGTTGGGCCATTGCATTGCC | 237 | targeting pyrE: aaactggcgctgatatggtttcat (194) |
| | pyrE-sRNA-R | atgaaaccatatcagcgccagtttGCAACCATTATCACCGCCAGAGGTA | 238 | |
| pSJ158 | pyrH-sRNA-F | gacgggttttgcattggtagccatTTTCTGTTGGGCCATTGCATTGCC | 239 | targeting pyrH: gacgggttttgcattggtagccat (195) |
| | pyrH-sRNA-R | atgctaccaatgcaaaacccgtcGCAACCATTATCACCGCCAGAGGTA | 240 | |
| pSJ159 | hpt-sRNA-F | cattacttctacagtatgtttcatTTTCTGTTGGGCCATTGCATTGCC | 241 | targeting hpt: cattacttctacagtatgtttcat (196) |
| | hpt-sRNA-R | atgaaacatactgtagaagtaatgGCAACCATTATCACCGCCAGAGGTA | 242 | |

TABLE 2

PCR conditions

| Name | Conditions |
|---|---|
| System | 2x GC buffer I: 25 μl; upstream and downstream primers: each 1 μl; dNTP: 5 μl; template plasmid: 0.3μ; enayme LA-Taq: 0.5 μl; ddH₂O: the reaction system was made up to 50 μl; |
| Program | pre-denaturation at 95° C.: 3 min; 30 cycles: denaturation at 94° C.: 30 s, annealing at 55° C.: 30 s, and extending at 72° C.: 3 min; 72° C.: 10 min; maintaining at 16° C. |

TABLE 3

Regulation of target function through sRNA technology

| Plasmid | Genbank No. | Target regulated through sRNA technology | Target function |
|---|---|---|---|
| pSJ39 | NC_012971.2 | sucC | succinyl-CoA synthetase, βsubunit |
| pSJ15 | NC_012971.2 | yjiM | hypothetical protein |
| pSJ30 | NC_012892.2 | frdD | fumarate reductase |
| pSJ53 | NC_012892.2 | lsrC | Autoinducer-2ABC transporter |
| pSJ44 | NC_012971.2 | glcE | glycolate oxidase, FAD-binding subunit |
| pSJ04 | NC_012971.2 | ybiW | pyruvate formatelyase |
| pSJ35 | NC_012971.2 | sdhA | succinate dehydrogenase |
| pSJ20 | NC_012892.2 | ptsH | HPr protein of phosphoenolpyruvate-sugar phosphotransferase system (PTS system) |

TABLE 3-continued

Regulation of target function through sRNA technology

| Plasmid | Genbank No. | Target regulated through sRNA technology | Target function |
|---|---|---|---|
| npSJ18 | NC_012971.2 | dhaK2 | dihydroxyacetone kinase |
| pSJ40 | NC_012971.2 | sucD | succinyl-CoA synthetase |
| pSJ33 | NC_012971.2 | frdA | fumarate reductase, αsubunit |
| pSJ21 | NC_012971.2 | ptsI | PTSI protein of phosphoenolpyruvate-sugar phosphotransferase system (PTS system) |
| pSJ10 | NC_012971.2 | fadB | fatty acid oxidation complex, α component |
| pSJ11 | NC_012971.2 | ackA | acetate kinase |
| pJF672 | NC_012971.2 | serC | 3-phosphoserine/phosphohydroxythreonine aminotransferase |
| pJF667 | NC_012971.2 | rpiA | ribose-5-phosphate isomerase A |
| pSJ12 | NC_012971.2 | pta | phosphate acetyltransferase/phosphate propionyltransferase |
| pSJ05 | NC_012971.2 | pflB | pyruvate formatelyase (inactive) |
| pSJ17 | NC_012971.2 | dhaK1 | dihydroxyacetone kinase subunit K |
| pJF673 | NC_012971.2 | serB | phosphoserine phosphatase |
| pSJ13 | NC_012892.2 | leuD | isopropylmalate isomerase |
| pSJ36 | NC_012892.2 | sdhB | succinate dehydrogenase |
| pSJ14 | NC_012892.2 | leuC | isopropylmalate isomerase LeuC |
| pSJ22 | NC_012892.2 | fsaA | fructose 6-phosphate aldolase 1 |
| pSJ06 | NC_012892.2 | tdcE | 2-ketobutyrate formatelyase/pyruvate formatelyase 4, inactive |
| pSJ38 | NC_012892.2 | sdhD | succinate dehydrogenase |
| pSJ09 | NC_012892.2 | fadJ | FadJ component of anaerobic fatty acid oxidation complex |
| pJF668 | NC_012971.2 | rpiB | allose-6-phosphate isomerase/ribose-5-phosphate isomerase B |
| pSJ34 | NC_012892.2 | pgi | phosphoglucose isomerase |
| pSJ43 | NC_012892.2 | glcF | glycolateoxidase, predicted iron-sulfur subunit |
| pSJ01 | NC_012892.2 | scpB | methylmalonyl-CoA decarboxylase |
| pSJ02 | NC_012892.2 | tdcD | propionate kinase |
| pSJ03 | NC_012892.2 | scpA | methylmalonyl-CoA mutase |
| pSJ37 | NC_012892.2 | sdhC | succinate dehydrogenase |
| pSJ19 | NC_007779.1 | dhaH | dihydroxyacetone kinase subunit M |
| pSJ24 | NC_012971.2 | ppk | polyphosphate kinase |
| pJF671 | NC_012971.2 | lpdA | lipoamide dehydrogenase |
| pSJ29 | NC_012971.2 | cyoA | cytochrome bo terminal oxidase subunit II |
| pSJ26 | NC_012892.2 | aceF | pyruvatede hydrogenase |
| pSJ08 | NC_007779.1 | PaaF | predicted 2,3-dehydroadipyl-CoA hydratase |
| pSJ16 | NC_012971.2 | purT | phosphoribosyl glycinamide formyltransferase 2 |
| pJF656 | NC_012971.2 | gdhA | glutamate dehydrogenase |
| pSJ66 | NC_012971.2 | agaW | N-acetylgalactosameine-specific IIC component 2 of PTS system |
| pJF674 | NC_012971.2 | serA | D-3-phosphoglycerate dehydrogenase/α-ketoglutarate reductase |
| pSJ50 | NC_012971.2 | yaeR | predicted lyase |
| pSJ41 | NC_012971.2 | tnaA | tryptophanase/L-cysteine desulfhydrase |
| pSJ07 | NC_012971.2 | pflD | formate acetyltransferase 2 |
| pSJ54 | NC_012971.2 | hemN | coproporphyrinogen III dehydrogenase |
| pJF664 | NC_012971.2 | cyoB | cytochrome bo terminal oxidase subunit I |
| pJF663 | NC_000913.3 | zwf | glucose 6-phosphate-1-dehydrogenase |
| pJF666 | NC_000913.3 | pgl | 6-phosphogluconolactonase |
| pJF670 | NC_000913.3 | gnd | 6-phosphogluconate dehydrogenase |
| pSJ128 | NC_007779.1 | rpe | ribulose-5-phosphate 3-epimerase |
| pSJ129 | NC_000913.3 | talA | transaldolase A |
| pSJ130 | NC_000913.3 | talB | transaldolase |
| pSJ131 | NC_000913.3 | tktA | transketolase I |
| pSJ132 | NC_000913.3 | tktB | transketolase II |
| pSJ133 | NC_000913.3 | ulaE | L-xylulose 5-phosphate 3-epimerase |
| pSJ141 | NC_000913.3 | yieK | predicted 6-phosphogluconolactonase |
| pSJ147 | NC_000913.3 | purH | AICAR transformylase |
| pSJ148 | NC_000913.3 | pyrB | aspartate carbamoyltransferase, catalytic subunit |
| pSJ149 | NC_000913.3 | pyrI | aspartate carbamoyltransferase, regulatory subunit |
| pSJ150 | NC_000913.3 | cysQ | adenosine-3'(2'),5'-bisphosphate nucleotidase |
| pSJ151 | NC_000913.3 | pyrC | dihydroorotase |
| pSJ152 | NC_000913.3 | gmk | guanylate kinase |
| pSJ153 | NC_000913.3 | guaA | GMP synthetase |
| pSJ154 | NC_000913.3 | guaB | IMP dehydrogenase |
| pSJ155 | NC_000913.3 | ndk | nucleoside diphosphate kinase |

TABLE 3-continued

Regulation of target function through sRNA technology

| Plasmid | Genbank No. | Target regulated through sRNA technology | Target function |
|---|---|---|---|
| pSJ156 | NC_000913.3 | pyrF | orotidine-5'-phosphate decarboxylase |
| pSJ157 | NC_000913.3 | pyrE | orotate phosphoribosyltransferase |
| pSJ158 | NC_000913.3 | pyrH | UMP kinase |
| pSJ159 | NC_000913.3 | hpt | hypoxanthine phosphoribosyltransferase |

Example 2

Construction of an *E. coli* WG Strain

Figure 2:
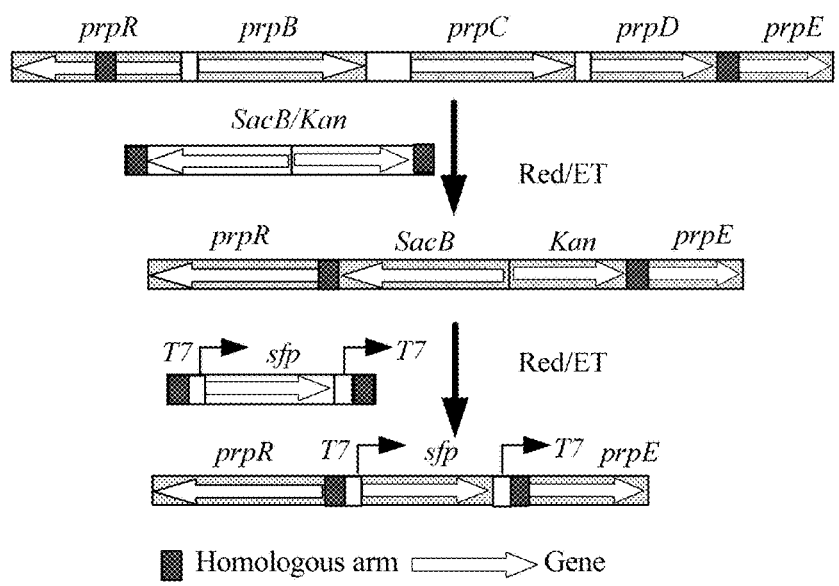
FIG. 2, a schematic diagram of the construction process of E. coli WG.

The operon for propionic acid metabolism was knocked out in *E. coli* and phosphopantetheinyl transferase gene sfp from the gene cluster of the surfactin synthesis pathway in *B. subtilis* was integrated into the site to construct an *E. coli* WG strain suitable for the biosynthesis of a polyketide, wherein the specific steps were as follows:

first, the sfp gene (encoding phosphopantetheinyl transferase, Genbank No.: NC_000964) with a length of 675 bp was amplified by PCR using the genome of *B. subtilis* as the template together with primers sfp-F and sfp-R (Table 4), and then the PCR product and plasmid pET21c-sfp (purchased from Novagen) were ligated with T4 DNA ligase after being respectively digested with NdeI and BamHI, constructing plasmid pET21c-sfp;

then, a Kan-SacB fragment (about 2.8 Kb) having a selective marker gene with homologous arms was amplified using plasmid pUC19-sacB/kan as the template together with primers SacB/Kan-F and SacB/Kan-R (Table 4), and then Kan-SacB was integrated into the operon for propionic acid metabolism in the chromosome of *E. coli* BL21 (DE3) using the λ Red/ET homologous recombination method (Datsenki et al., PNAS, 2000, 97: 6640-6645), replacing the DNA fragments of prpR, prpB, prpC and prpD in the operon for propionic acid metabolism; using WG-F and WG-R as the primers, the SacB/Kan gene located in the chromosome of the recombinant strain was amplified for verification;

then, the T7 promoter-carrying sfp gene was amplified from pET21c-sfp using sfpR-F and sfpR-R; and the SacB-Kan fragment of the recombinant strain was replaced with the T7-sfp-T7 fragment again using the λ Red/ET homologous recombination method, and finally an *E. coli* WG strain required by the present invention was obtained that was suitable for the biosynthesis of a polyketide, wherein schematic diagram of the specific restructuring process was as shown in FIG. 2.

TABLE 4

Primers used in this example and the corresponding base sequences thereof

| Primer | Base sequence | SEQ ID NO: |
|---|---|---|
| Sfp-F | CTAG*GGATCC*TTATAAAAGCTCTTCGTACG | 154 |
| Sfp-R | GGAATTC*CATATG*ATGAAGATTTACGGAATTTA | 155 |
| sfpR-F | TGGCGTAATGCAGCAGAAAATGGCCCGCGAAATTAATACGACTCACTATAGG | 156 |
| sfpR-R | GATAAAATTCGCTAAAAGACATATGTATATCTCCTTCTTAAAGTTAAACAAAATTATTTCTAGAGGGGAATTGTTATCCGCTCACAATTCCCCTATAGTGAGTCGTATTAATTTCGCGGGTTATAAAAGCTCTTCGTACG | 157 |
| sacB/Kan-F | TGGCGTAATGCAGCAGAAAATGGTCAGAAGAACTCGTCAAGAAG | 158 |
| sacB/Kan-R | GATAAAATTCGCTAAAAGACATCATCACATATACCTGCCGTTC | 159 |
| WG-F | GAACGTCGTCCGGCTGATGCC | 160 |
| WG-R | TGGTATCGGTCTGCGATTCCGAC | 161 |

Example 3

Construction of Plasmid pZG07

Figure 3:
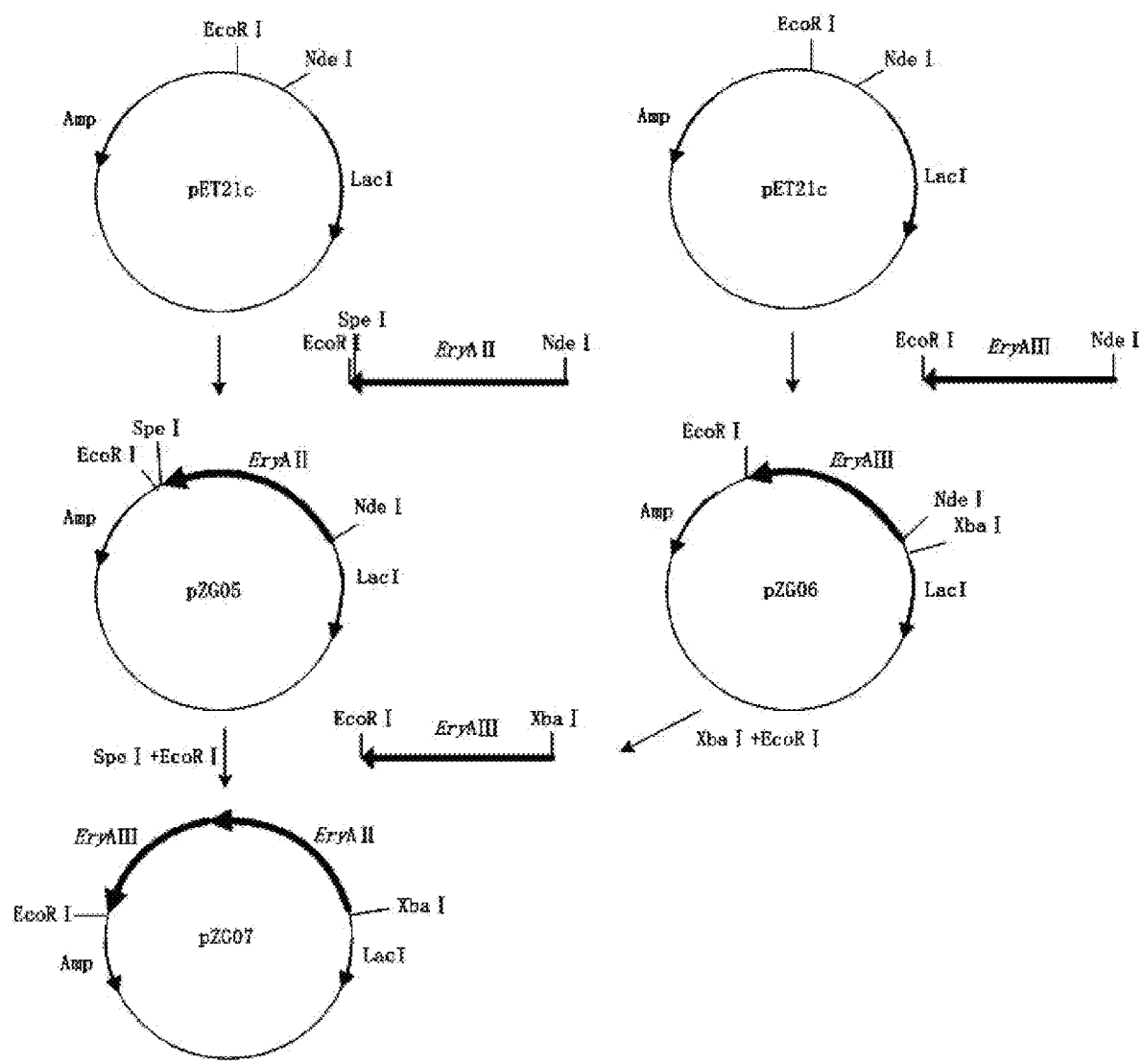
FIG. 3, the construction process of plasmid pZG07.

Genes eryAII (encoding polyketide synthetase DEBS2 of *Streptomyces erythreus*, derived from Genbank No.: NC_009142) and eryAIII (encoding polyketide synthetase DEBS3 of *Streptomyces erythreus*, derived from Genbank No.: NC_009142) were respectively PCR amplified using the genomic DNA of *Saccharopolyspora erythraea* as the template together with primers eryAII-F and eryAII-R as well as eryAIII-F and eryAIII-R (Table 5), the purified PCR products were respectively double digested with NdeI/HindIII, and then the double-digested PCR products were respectively ligated with T4 DNA ligase to plasmid pET21c subjected to the same digestion, respectively obtaining plasmids pZG05 (containing eryAII) and pZG06 (containing eryAIII); and then, pZG06 was digested with XbaI/EcoRI, the DNA fragment containing eryAIII gene was ligated with T4 DNA ligase to plasmid pZG05 digested with SpeI/EcoRI after being recovered, constructing plasmid pZG07, wherein the schematic diagram of the construction process of the polyketone synthesis gene cluster plasmid pZG07 was as shown in FIG. 3.

TABLE 5

Primers used in this example and the corresponding base sequences thereof

| Primer | Base sequence | SEQ ID NO: |
|---|---|---|
| eryA II-F | GGAATTC*CATATG*GTGACTGACAGCGAGAAGGTGGC | 162 |
| eryA II-R | CTAGA*GAATTC*CTAGTCTACAGGTCCTCTCCCCCGCC | 163 |
| eryA III-F | GGAATTC*CATATG*ATGAGCGGTGACAACGGCATGA | 164 |
| eryA III-R | GAT*GAATTC*TCATGAATTCCCTCCGCCCAGC | 165 |

Example 4

Construction of Plasmid pZG08

Gene pccB (encoding propionyl-CoA carboxylase β-CT subunit, derived from Genbank No.: NC_003888.3) and gene accA (encoding propionyl-CoA carboxylase a-CT subunit, derived from Genbank No.: NC_003888.3) were respectively amplified using the genomic DNA of *Streptomyces coelicolor* as the template together with primers pccB-F and pccB-R as well as accA2-F and accA2-R (Table 6), the purified PCR products were respectively double digested with NcoI/EcoRI, and then the double-digested PCR products were respectively ligated with T4 DNA ligase to the pET28a plasmid double digested with NcoI/EcoRI, constructing plasmids pZG01 and pZG02; and then, pZG02 was double digested with XbaI/EcoRI, the DNA fragment containing the gene accA2 was recovered and ligated with T4 DNA ligase to the pZG01 plasmid double digested with SpeI/EcoRI, obtaining plasmid pZG03.

Gene eryAI (encoding polyketide synthetase DEBS1 of *Streptomyces erythreus*, Genbank No.: NC_009142) was PCR amplified using the genomic DNA of *Saccharopolyspora erythraea* as the template together with primers eryAI-F and eryAI-R, the purified PCR product was double digested with NdeI/EcoRI and then ligated with T4 DNA ligase to plasmid pET28a double digested with NdeI/EcoRI, constructing plasmid pZG04;

pZG04 was linearized with Bg/II and the linearized fragment was recovered, the ends of the linearized fragment were then digested with exonuclease I to convert the cohesive ends resulting from the digestion of Bg/II to blunt ends, after which the linearized fragment was recovered again, and finally the fragment was digested with HindIII to recover the eryAI gene fragment; and pZG03 was first linearized with EcoRI and recovered, the cohesive ends of EcoRI were then converted to blunt ends by the use of exonuclease I and recovered, and finally the linearized pZG03 was digested with HindIII and recovered.

Figure 4:
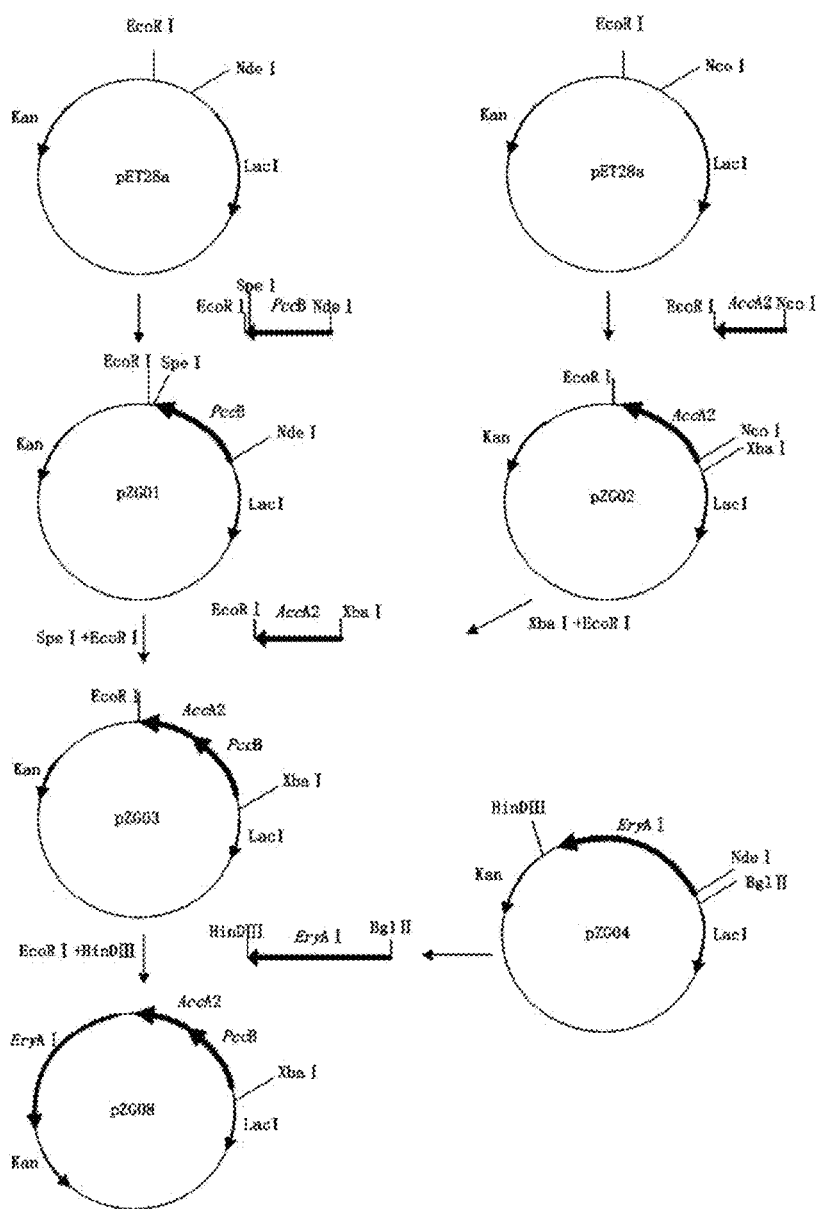
FIG. 4, the construction process of plasmid pZG08.

The above recovered pZG03 was ligated to the eryAI gene fragment, constructing plasmid pZG08, wherein the schematic diagram of the construction process of the plasmid pZG08 was as shown in FIG. 4.

TABLE 6

Primers used in this example and the corresponding base sequences thereof

| Primer | Base sequence | SEQ ID NO: |
|---|---|---|
| eryA I-F | GGAATTC*CATATG*GTGGCGGACCTGTCAAAGCTCTC | 166 |
| eryA I-R | GAT*GAATTC*TCAATCGCCGTCGAGCTCCCG | 167 |
| pccB-F | GGAATTC*CATATG*ATGGGCAGCAGCCATCATCATC | 168 |
| pccB-R | CTAGA*CTAGT*TTACAGGGGGATGTTGCCGTG | 169 |
| accA2-F | CATG*CCATGG*ATATGCGCAAGGTGCTCATCGC | 139 |
| accA2-R | GAT*GAATTCGAATTC*TCAGTCCTTGATCTCGCAGATGGC | 27 |

Example 5

Construction of an Engineered Strain of the Polyketide 6-dEB and its Fermentation Culture in a 5 L Tank The plasmids pZG07 and pZG08 were co-transformed into the above-obtained host strain *E. coli* WG for heterologously synthesizing a polyketide, obtaining an engineered strain *E. coli* WG (pZG07/pZG08) (for producing 6-dEB, an erythromycin precursor) that is capable of effectively synthesizing the polyketide. Single colonies were picked into 2 ml of LB medium supplemented with 100 mg/L of carbenicillin and 50 mg/L of kanamycin, and the mixture was cultured at 220 rpm, 37° C. overnight, giving primary seeds.

Then, the above-obtained primary seeds were inoculated into a 500 ml shake flask containing 50 ml of LB medium supplemented with 100 mg/L of carbenicillin and 50 mg/L of kanamycin at an inoculum size of 1%, and the mixture was cultured at 220 rpm, 37° C. until the OD600 was about 1, giving secondary seeds.

Then, the resulting secondary seeds were inoculated into a 5 L tank containing 4 L of fermentation medium supplemented with 100 mg/L of carbenicillin and 50 mg/L of kanamycin at an inoculum size of 1%, IPTG with a final concentration of 0.1 mM and 20 mM of sodium propionate were added at the same time, and the fermentation was completed after inducing and culturing the mixture at 22° C., 250 rpm for 5 days.

Example 6

Preparation of 6-dEB and HPLC-ELSD Analysis and Detection

Figure 5:
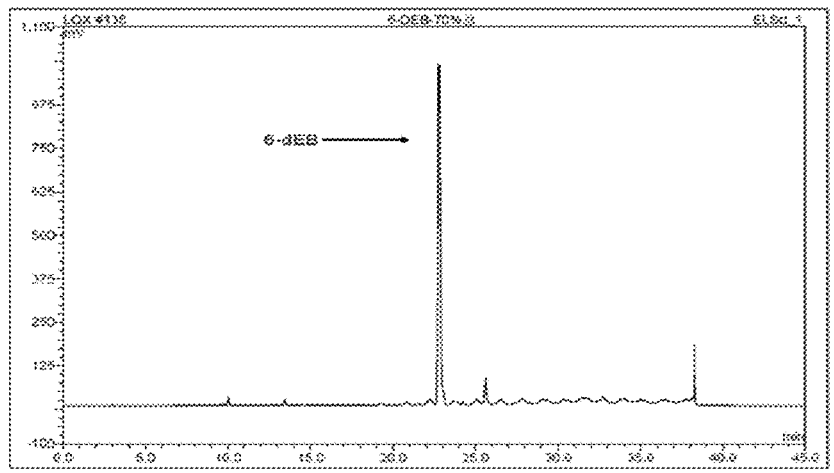
FIG. 5, HPLC analysis of isolated fractions of 6-dEB.

The fermentation broth of Example 5 was extracted three times with an equal volume of ethyl acetate and concentrated under reduced pressure to give a crude extract. The crude extract was eluted in a reversed phase C-18 column using methanol-water system, wherein the ratios of methanol were 30%, 50%, 70% and 100%, respectively. The isolated fractions were analyzed using Ultimate 3000 analytical HPLC. The analysis results showed that the product 6-dEB was mainly present in the fraction with a methanol ratio of 70%, and the HPLC analysis was shown in FIG. 5.

The above crude fraction containing 6-dEB was isolated by a reverse phase C-18 column and analyzed and prepared by HPLC-ELSD to give pure 6-dEB. The HPLC-ELSD detection and preparation conditions were as follows. The fraction eluted with 70% methanol was isolated and prepared by Ultimate 3000 preparative HPLC, wherein the chromatographic column model was: TSK-100V, 5 µm, 19*150 mm, flow rate 15 ml/min, and mobile phase 50% acetonitrile/water system for isocratic elution. The ELSD detector conditions were as follows: evaporative light scattering detector drift tube temperature: 95° C.; gas flow rate: 1.6 l/min; and gain: 16. Retention time $t_R$: 10.3 min.

Figure 6:
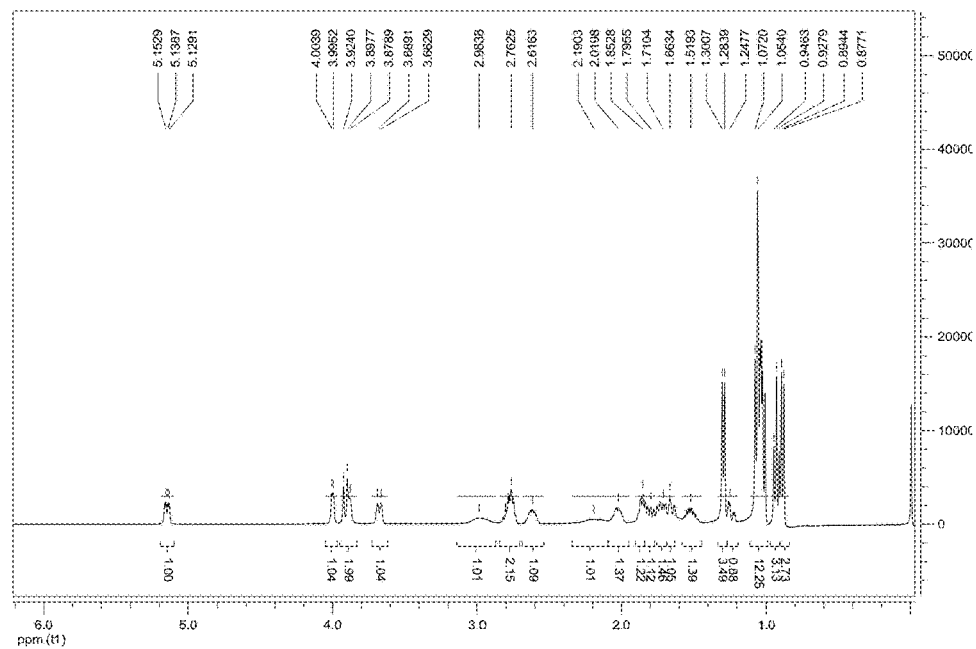
FIG. 6, hydrogen NMR spectrum of pure 6-dEB prepared.

The pure 6-dEB was verified by nuclear magnetic analysis. The hydrogen spectrum was shown in FIG. 6. It can be seen from the figure that the chemical shift of H spectrum of the prepared pure product was consistent with that reported in the literature (Xin Gao, Sang Kook Woo, Michael J. Krische, Total Synthesis of 6-Deoxyerythronolide B via C—C Bond-Forming Transfer Hydrogenation, *J. Am. Chem. Soc.* 2013, 135, 4223-4226), determining that this compound is 6-dEB.

Figure 7:
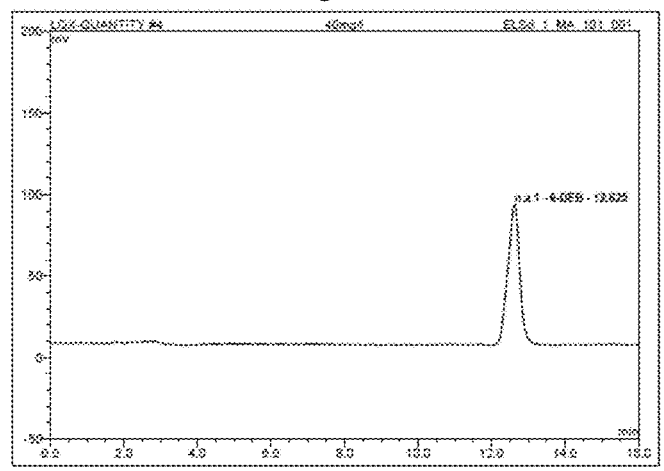
FIG. 7, HPLC-ELSD analysis diagram of 6-dEB at 40 mg/L.

The prepared standard was formulated as 40 mg/L of methanol solution and analyzed by Ultimate 3000 analytical HPLC, with conditions as follows: chromatographic column TSK-100V, 5 µm, 4.6*150 mm; flow rate 1 ml/min; and mobile phase acetonitrile/water, with 50% of acetonitrile, for gradient elution. ELSD was used as the detector and the conditions were as follows: evaporative light scattering detector drift tube temperature: 95° C.; gas flow rate: 1.6 l/min; and gain: 16. It can be seen from FIG. 7 that the pure 6-dEB prepared had a very high purity, with the purity up to 98% or more.

Example 7

Transformation and Fermentation of sRNA Plasmids

The various sRNA plasmids expressed in Example 1 (using pACYCDuet-1 (purchased from Novagen) as a blank control) were respectively transformed into the host cells *E. coli* WG (pZG07/pZG08) (for producing 6-dEB, an erythromycin precursor), single colonies were respectively picked into 2 ml of LB medium containing carbenicillin (100 mg/L), kanamycin (50 mg/L) and chloramphenicol (34 mg/L), and the mixture was cultured at 37° C., 250 rpm/min overnight for 12 h as seeds for shaker fermentation culture.

The above seeds were inoculated in a 100 ml shake flask containing 10 ml of 6-dEB fermentation medium (containing carbenicillin, kanamycin and chloramphenicol antibiotics) at an inoculum size of 1%, and sodium propionate precursor with a final concentration of 20 mM and 100 mM of isopropyl-β-D-thiogalactopyranoside (IPTG) were added at the same time for initial induction, wherein each sample was run three times in parallel. The shake flask was placed in a shaker at 22° C., 250 rpm/min to ferment for 5 days. After the fermentation was completed, the fermentation broth was poured into a 10 ml centrifuge tube and stored at −20° C. for subsequent detection and analysis.

Example 8

Analysis and Detection of 6-dEB of the Fermentation Broth in Example 7

The fermentation broth of Example 7 was analyzed and detected by a high performance liquid chromatography-evaporative light scattering detector (HPLC-ELSD). The conditions were as follows: chromatographic column TSK-100V, 5 µm, 4.6*150 mm; flow rate 1 ml/min; and mobile phase acetonitrile/water, with 50% of acetonitrile, for isocratic elution. ELSD was used as the detector and the conditions were as follows: evaporative light scattering detector drift tube temperature: 95° C.; gas flow rate: 1.6 l/min; and gain: 16.

The results of the effects of attenuation of different genes on the synthesis of 6-dEB were shown in Table 7 (the yield of 6-dEB in the control group *E. coli* WG (pZG07/pZG08/pACYCDunet-1) was 100%). As can be seen from Table 7: attenuation of each of these key target genes by the use of sRNA was beneficial to the synthesis of the target product 6-dEB. For example, the key target gene regulated by the strain *E. coli* WG (pZG07/pZG08/pSJ39) was sucC (synthetase: succinyl-CoA synthetase, β subunit). Compared with the control group *E. coli* WG (pZG07/pZG08/pACYC-Dunet-1), attenuation of sucC may allow the yield increase rate of 6-dEB synthesized by the host to reach 63.2%. *E. coli* WG (pZG07/pZG08/pSJ130) may increase the highest yield, the key target gene regulated thereby is talB (transaldolase), and attenuation of talB may allow the yield increase rate of 6-dEB synthesized by the host to reach 1008.81%.

Using an sRNA method to regulate the metabolic network of the chassis cells of *E. coli*, the heterologous synthesis of the polyketide can be significantly improved by attenuating these genes. Targets through attenuating which to increase the yield of the polyketide by 20% or more were as follows: ybiW, fadB, ackA, pta, yjiM, dhaK2, ptsH, ptsI, frdD, frdA, sdhA, sucC, sucD, glcE, lsrC, rpiA, serC, talA, talB, zwf, pyrI, cysQ, gmk, guaB, pyrH and hpt.

TABLE 7

Effect of sRNA interference on the synthesis of 6-dEB by heterologous host *E. coli*

| Target attenuated by an sRNA plasmid | Yield of 6-dEB (mg/L) | Yield increase rate of 6-dEB (%) |
| --- | --- | --- |
| sucC | 23.34 | 63.2406 |
| yjiM | 21.97 | 53.6493 |
| frdD | 21.33 | 49.1429 |
| lsrC | 20.95 | 46.5013 |
| glcE | 20.02 | 39.9762 |
| ybiW | 19.97 | 39.6476 |
| sdhA | 19.82 | 38.5955 |
| ptsH | 19.66 | 37.4517 |
| dhaK2 | 19.11 | 33.6389 |
| sucD | 19.11 | 33.6232 |
| frdA | 18.61 | 30.1259 |
| ptsI | 18.58 | 29.9126 |
| fadB | 18.25 | 27.6126 |
| ackA | 17.76 | 24.169 |
| serC | 17.74 | 24.0419 |
| rpiA | 17.50 | 22.3742 |
| Pta | 17.18 | 20.1588 |
| pflB | 17.12 | 19.7255 |
| dhaK1 | 17.05 | 19.2565 |
| serB | 16.81 | 17.5799 |
| lueD | 16.59 | 16.0076 |
| sdhB | 16.52 | 15.5126 |
| lueC | 16.38 | 14.5198 |
| fsaA | 16.30 | 13.9704 |
| tdcE | 16.09 | 12.5035 |
| sdhD | 16.08 | 12.4802 |
| fadJ | 15.98 | 11.7827 |
| rpiB | 15.88 | 11.0452 |
| Pgi | 15.75 | 10.1108 |
| glcF | 15.67 | 9.57697 |
| scpB | 15.59 | 9.00411 |
| tdcD | 15.57 | 8.85684 |
| scpA | 15.51 | 8.47025 |

TABLE 7-continued

Effect of sRNA interference on the synthesis of 6-dEB by heterologous host E. coli

| Target attenuated by an sRNA plasmid | Yield of 6-dEB (mg/L) | Yield increase rate of 6-dEB (%) |
|---|---|---|
| sdhC | 15.51 | 8.46854 |
| dhaH | 15.50 | 8.36834 |
| Ppk | 15.27 | 6.76265 |
| lpdA | 15.27 | 6.75137 |
| cyoA | 15.18 | 6.12731 |
| aceF | 15.12 | 5.72787 |
| PaaF | 15.05 | 5.26518 |
| purT | 15.02 | 5.00937 |
| gdhA | 15.01 | 4.97136 |
| agaW | 14.82 | 3.62747 |
| sera | 14.62 | 2.24778 |
| yaeR | 14.56 | 1.84435 |
| tnaA | 14.56 | 1.81189 |
| pflD | 14.41 | 0.77645 |
| hemN | 14.35 | 0.37817 |
| cyoB | 14.35 | 0.3568 |
| talB | 158.57 | 1008.881 |
| talA | 121.34 | 748.5315 |
| zwf | 93.06 | 550.7692 |
| pgl | 77.56 | 442.3776 |
| rpe | 63.46 | 343.7762 |
| tktA | 60.36 | 322.0979 |
| gnd | 56.41 | 294.4755 |
| ulaE | 50.83 | 255.4545 |
| tktB | 47.67 | 233.3566 |
| yieK | 47.44 | 231.7483 |
| guaB | 127.21 | 789.5804 |
| hpt | 110.28 | 671.1888 |
| cysQ | 108.14 | 656.2238 |
| pyrI | 97.03 | 578.5315 |
| pyrH | 95.0 | 564.3357 |
| gmk | 94.32 | 559.5804 |
| pyrF | 89.30 | 524.4755 |
| guaA | 86.37 | 503.986 |
| pyrE | 85.24 | 496.0839 |
| purH | 77.85 | 444.4056 |
| ndk | 77.678 | 443.2028 |
| pyrB | 75.08 | 425.035 |
| pyrC | 54.10 | 278.3217 |
| pACYCDuent-1 (control) | 14.30 | 0 |

Example 9

Combined Attenuation Through Co-Transformation of sRNA Plasmids Further Improves the Yield of the Polyketide 6-dEB As can be seen from the data in Example 8: targets after attenuating which to increase the yield of the polyketide by 20% or more, ybiW, fadB, ackA, pta, yjiM, dhaK2, ptsH, ptsI, frdD, frdA, sdhA, sucC, sucD, glcE, lsrC, rpiA and serC, were selected, chloramphenicol resistance in these attenuated plasmids above was replaced with apramycin resistance for resistance screening of subsequent combination-co-transformation.

Construction of a plasmid with its resistance replaced was based on the POE-PCR technical method (You et al., Simple cloning via direct transformation of PCR product (DNA Multimer) to Escherichia coli and Bacillus subtilis. Appl Environ Microbiol, 78(5): 1593-1595), by taking the replacement of the resistance of the control plasmid pACYCDuent-1 as an example, the apramycin resistance gene of the pKC1139 plasmid was first directly amplified by PCR using pKC1139 (a universal plasmid for Streptomyces) as the template together with the Aparamycin-F and Aparamycin-R primers in Table 8 and the PCR conditions (see Table 9); and sequences except for the chloramphenicol resistance gene of the pACYCDuent-1 plasmid were amplified by PCR using pACYCDuent-1 as the template together with the sRNA-Aparamycin-F and sRNA-Aparamycin-R primers in Table 8 and the PCR conditions. Then, PCR was carried out using the PCR conditions in Table 9 (note: primers were not added, and the templates were the apramycin resistance gene and the pACYCDuent-1 without the chloramphenicol resistance gene amplified in the first step, each 1 μl), this PCR product was directly transformed into DH10B after being recovered by a PCR cleaning and recovering kit, and the mixture was plated on an LB solid medium plate containing 50 mg/L of apramycin and cultured overnight. Single colonies were picked into 2 ml of LB medium containing 50 mg/L of apramycin, the mixture was cultured at 220 rpm, 37° C. overnight, and a plasmid extraction kit was used to extract a plasmid, obtaining plasmid pSJ77.

TABLE 8

Primer information and PCR conditions

| Primer name | Sequence (5'→3') | SEQ ID NO: |
|---|---|---|
| Aparamycin-F | caccaataactgccttaaaaaaaGCCAATCGACT GGCGAGCGG | 170 |
| Aparamycin-R | tcgagattttcaggagctaaggaagctaaaATGC AATACGAATGGCGAAA | 171 |
| sRNA-Aparamycin-F | ccgctcgccagtcgattggcttttttttaaggcag ttattggtg | 172 |
| sRNA-Aparamycin-R | tttcgccattcgtattgcattttagcttccttag ctcctgaaaatctcga | 173 |

TABLE 9

PCR conditions

| Name | PCR conditions |
|---|---|
| System | 5x PS buffer: 5 μl; dNTP: 2.5 μl; template: 0.3 μl; upstream and downstream primers: each 0.5 μl; PrimeStar enzyme: 0.25 μl; ddH$_2$O: to make up to 25 μl; |
| Program | pre-denaturation at 98° C.: 3 min; 30 cycles: denaturation at 98° C.: 10 s, annealing at 55° C.: 15 s, and extending at 72° C.: 3 min 10 s; 72° C.: 10 min; maintaining at 16° C. |

The replacement of the resistance of the remaining sRNA-expressing plasmids was the same as above by using the same primers and PCR conditions to replace chloramphenicol resistance in a plasmid with apramycin resistance, and the information of each sRNA plasmid was as shown in Table 10.

TABLE 10 sRNA plasmid information

| Name | Plasmid information | Resistance |
|---|---|---|
| pSJ77 | pACYCDuet-1-derived plasmid, with chloramphenicol resistance changed into apramycin resistance, an sRNA empty plasmid | apramycin |
| pSJ78 | pSJ04-derived plasmid, with chloramphenicol resistance changed into apramycin resistance, expresses an sRNA with ybiW attenuated | apramycin |

TABLE 10-continued sRNA plasmid information

| Name | Plasmid information | Resistance |
|---|---|---|
| pSJ79 | pSJ10-derived plasmid, with chloramphenicol resistance changed into apramycin resistance, expresses an sRNA with fadB attenuated | apramycin |
| pSJ80 | pSJ11-derived plasmid, with chloramphenicol resistance changed into apramycin resistance, expresses an sRNA with ackA attenuated | apramycin |
| pSJ81 | pSJ12-derived plasmid, with chloramphenicol resistance changed into apramycin resistance, expresses an sRNA with pta attenuated | apramycin |
| pSJ82 | pSJ15-derived plasmid, with chloramphenicol resistance changed into apramycin resistance, expresses an sRNA with yjiM attenuated | apramycin |
| pSJ83 | pSJ18-derived plasmid, with chloramphenicol resistance changed into apramycin resistance, expresses an sRNA with dhaK2 attenuated | apramycin |
| pSJ84 | pSJ20-derived plasmid, with chloramphenicol resistance changed into apramycin resistance, expresses an sRNA with ptsH attenuated | apramycin |
| pSJ85 | pSJ21-derived plasmid, with chloramphenicol resistance changed into apramycin resistance, expresses an sRNA with ptsI attenuated | apramycin |
| pSJ86 | pSJ30-derived plasmid, with chloramphenicol resistance changed into apramycin resistance, expresses an sRNA with frdD attenuated | apramycin |
| pSJ87 | pSJ33-derived plasmid, with chloramphenicol resistance changed into apramycin resistance, expresses an sRNA with frdA attenuated | apramycin |
| pSJ88 | pSJ35-derived plasmid, with chloramphenicol resistance changed into apramycin resistance, expresses an sRNA with sdhA attenuated | apramycin |
| pSJ89 | pSJ39-derived plasmid, with chloramphenicol resistance changed into apramycin resistance, expresses an sRNA with sucC attenuated | apramycin |
| pSJ90 | pSJ40-derived plasmid, with chloramphenicol resistance changed into apramycin resistance, expresses an sRNA with sucD attenuated | apramycin |
| pSJ92 | pS44-derived plasmid, with chloramphenicol resistance changed into apramycin resistance, expresses an sRNA with glcE attenuated | apramycin |
| pSJ93 | pSJ53-derived plasmid, with chloramphenicol resistance changed into apramycin resistance, expresses an sRNA with lsrC attenuated | apramycin |
| pSJ94 | pJF667-derived plasmid, with chloramphenicol resistance changed into apramycin resistance, expresses an sRNA with rpiA attenuated | apramycin |
| pSJ95 | pJF672derived plasmid, with chloramphenicol resistance changed into apramycin resistance, expresses an sRNA with serC attenuated | apramycin |

The sRNA-expressing plasmids (using pSJ77 as a blank control) constructed above and the sRNA-expressing plasmids constructed in Example 1 for increasing the relative yield by 20% were combined in pairs, and co-transformed in the host cells E. coli WG (pZG07/pZG08) (for producing 6-dEB, an erythromycin precursor), using the fermentation method in Example 7 and the analysis and detection of 6-dEB in Example 8.

In the sRNA combined fermentation experiment, the yield of 6-dEB in the control group E. coli WG (pZG07/pZG08/pSJ39/pSJ77) was 100%, and the yield of the polyketide 6-dEB was further increased by attenuating the key target genes in combination.

The experimental results of the effect of combined sRNA interference on the synthesis of 6-dEB by heterologous host E. coli were as shown in Table 11.

TABLE 11

Effect of combined sRNA interference on the synthesis of 6-dEB by heterologous host E. coli

| Name of plasmid combination | Target attenuated by an sRNA plasmid | Yield of 6-dEB (mg/L) | Relative yield increase rate of 6-dEB (%) |
|---|---|---|---|
| pSJ30 + pSJ39 | frdD + sucC | 28.73 | 24.36 |
| pSJ53 + pSJ30 | lsrC + frdD | 27.11 | 17.36 |
| pSJ53 + pSJ39 | lsrC + sucC | 24.15 | 4.53 |
| pSJ30 + pSJ94 | frdD + rpiA | 23.24 | 0.59 |
| pSJ39 + pSJ77 | sucC + pACYCDuent-1 (control) | 23.10 | 0.00 |
| pSJ30 + pSJ88 | frdD + sdhA | 23.07 | −0.14 |
| pSJ30 + pSJ84 | frdD + ptsH | 22.54 | −2.43 |
| pSJ30 + pSJ82 | frdD + yjiM | 22.33 | −3.33 |
| pSJ30 + pSJ81 | frdD + pta | 22.20 | −3.89 |
| pSJ53 + pSJ80 | lsrC + ackA | 22.00 | −4.75 |
| pSJ30 + pSJ39 | frdD + sucD | 21.90 | −5.20 |
| pSJ30 + pSJ79 | frdD + fadB | 21.87 | −5.34 |
| pSJ53 + pSJ94 | lsrC + rpiA | 21.42 | −7.26 |
| pSJ30 + pSJ80 | frdD + ackA | 21.08 | −8.76 |
| pSJ53 + pSJ92 | lsrC + glcE | 20.87 | −9.65 |
| pSJ53 + pSJ79 | lsrC + fadB | 20.64 | −10.63 |
| pSJ53 + pSJ85 | lsrC + ptsI | 20.63 | −10.68 |
| pSJ30 + pSJ83 | frdD + dhaK2 | 20.55 | −11.06 |
| pSJ53 + pSJ81 | lsrC + pta | 20.12 | −12.91 |
| pSJ53 + pSJ39 | lsrC + sucC | 20.09 | −13.02 |
| pSJ30 + pSJ85 | frdD + ptsI | 19.67 | −14.86 |
| pSJ30 + pSJ78 | frdD + ybiW | 19.56 | −15.34 |
| pSJ53 + pSJ87 | lsrC + frdA | 19.34 | −16.28 |
| pSJ53 + pSJ90 | lsrC + sucD | 18.87 | −18.33 |
| pSJ30 + pSJ83 | lsrC + dhaK2 | 18.37 | −20.48 |
| pSJ53 + pSJ78 | lsrC + ybiW | 17.81 | −22.91 |
| pSJ53 + pSJ88 | lsrC + sdhA | 17.70 | −23.36 |
| pSJ53 + pSJ95 | lsrC + serC | 17.46 | −24.41 |
| pSJ30 + pSJ87 | frdD + frdA | 17.24 | −25.37 |
| pSJ53 + pSJ82 | lsrC + yjiM | 16.29 | −29.46 |
| pSJ53 + pSJ84 | lsrC + ptsH | 13.94 | −39.65 |
| pSJ30 + pSJ95 | frdD + serC | 12.28 | −46.83 |

The experimental results showed that although most combined attenuations cannot effectively improve the synthesis of the polyketide, combined attenuation of frdD and sucC may further increase the yield of 6-dEB by 24% or more compared with the yield by attenuating sucC alone, and attenuating lsrC and frdD simultaneously may further increase the yield of 6-dEB by 17% or more.

Example 10 sRNA Plasmids with Two Targets Attenuated Further Increase the Yield of the Polyketide 6-dEB It can be seen according to the data in Example 8: targets attenuated were as follows that increased the yield of the polyketide by more than 550%: genes talA, talB and zwf for nucleotide synthesis and other metabolism modules and genes pyrI, cysQ, gmk, guaB, pyrH and hpt for pentose phosphate and glyoxylate pathway modules, and the effect of the simultaneous attenuation of the targets of the two modules on the yield of the polyketide 6-dEB synthesized was investigated.

sRNA plasmids with two targets attenuated were all constructed by a digestion and series connection method. Taking the construction of pSJ333 as an example: a talB-targeting sRNA skeleton was amplified using pSJ130 as the template and sRNA-F/R as the primers (Table 12), wherein the PCR conditions were the same as that in Table 9 of Example 9. The PCR product was digested with BamHI and HindIII after being cleaned and recovered; and pSJ129 as the vector was digested with BglII and HindIII at the same time and cleaned and recovered. The above PCR digested-product was ligated with T4 DNA ligase to the double-digested pSJ129 product, obtaining plasmid pSJ333. The remaining plasmids were obtained in the same way, obtaining plasmids pSJ404-pSJ421 finally, and the plasmid information was as shown in Table 13.

TABLE 12

Primer information

| Primer name | Sequence (5'→3') |
|---|---|
| sRNA-F | CGGGATCCTAACACCGTGCGTGTTGACTATTTTA |
| sRNA-R | CCCAAGCTTAGATCTACTAGTTATAAACGCAGAAAGG |

TABLE 13

Combined sRNA plasmid information

| Name | Target regulated (attenuated) by sRNA technology | Resistance |
|---|---|---|
| pSJ333 | talA + talB | chloramphenicol |
| pSJ334 | cysQ + guaB | chloramphenicol |
| pSJ404 | talA + pyrI | chloramphenicol |
| pSJ405 | talA + cysQ | chloramphenicol |
| pSJ406 | talA + gmk | chloramphenicol |
| pSJ407 | talA + guaB | chloramphenicol |
| pSJ408 | talA + pyrH | chloramphenicol |
| pSJ409 | talA + hpt | chloramphenicol |
| pSJ410 | talB + pyrI | chloramphenicol |
| pSJ411 | talB + cysQ | chloramphenicol |
| pSJ412 | talB + gmk | chloramphenicol |
| pSJ413 | talB + guaB | chloramphenicol |
| pSJ414 | talB + pyrH | chloramphenicol |
| pSJ415 | talB + hpt | chloramphenicol |
| pSJ416 | zwf + pyrI | chloramphenicol |
| pSJ417 | zwf + cysQ | chloramphenicol |
| pSJ418 | zwf + gmk | chloramphenicol |
| pSJ419 | zwf + guaB | chloramphenicol |
| pSJ420 | zwf + pyrH | chloramphenicol |
| pSJ421 | zwf + hpt | chloramphenicol |

The combined sRNA-expressing plasmids (using pACYCDuent-1 as a blank control) constructed above were transformed in the host cells *E. coli* WG (pZG07/pZG08) (for producing 6-dEB, an erythromycin precursor), using the fermentation method in Example 7 and the analysis and detection of 6-dEB in Example 8.

In the sRNA combined fermentation experiment, the yield of 6-dEB in the control group *E. coli* WG (pZG07/pZG08/pSJ39/pSJ77) was 100%, and the yield of the polyketide 6-dEB was further increased by attenuating the key target genes in combination.

Figure 8:
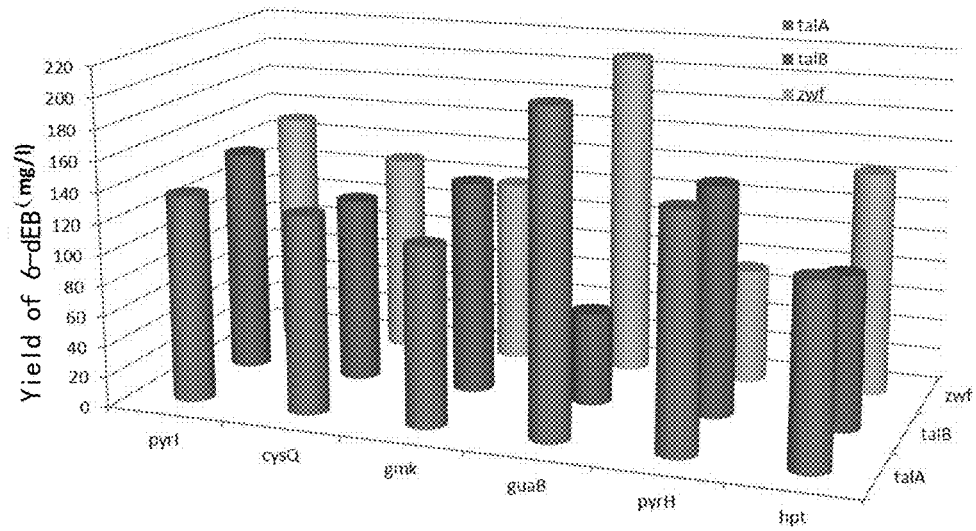
FIG. 8, effect of sRNA combinatorial regulation on the heterologous synthesis of 6-dEB by E. coli.

The experimental results of the effect of combined sRNA interference on the synthesis of 6-dEB by heterologous host *E. coli* were as shown in Table 14 and FIG. 8. The experiment showed that although all the combined attenuations can effectively improve the synthesis of the polyketide, only combined attenuations of talA+guaB and zwf+guaB may further increase the yield of 6-dEB by 32% or more compared with the yield by attenuating talB alone and by 1300% or more compared with the yield of the control group, enabling the shake flask yield of 6-dEB to reach 210 mg/L or more.

TABLE 14

Effect of combined sRNA interference on the synthesis of 6-dEB by heterologous host *E. coli*

| Plasmid name | Target attenuated by an sRNA plasmid | Yield of 6-dEB (mg/L) | Relative yield increase rate of 6-dEB (%) |
|---|---|---|---|
| pACYCDuent-1 | control | 14.30 | 0.00 |
| pSJ404 | talA + pyrI | 135.10 | 844.76 |
| pSJ405 | talA + cysQ | 128.87 | 801.19 |
| pSJ406 | talA + gmk | 117.09 | 718.81 |
| pSJ407 | talA + guaB | 209.38 | 1364.20 |
| pSJ408 | talA + pyrH | 153.30 | 972.03 |
| pSJ409 | talA + hpt | 118.84 | 731.05 |
| pSJ410 | talB + pyrI | 145.38 | 916.64 |
| pSJ411 | talB + cysQ | 120.11 | 739.93 |
| pSJ412 | talB + gmk | 138.00 | 865.03 |
| pSJ413 | talB + guaB | 60.05 | 319.93 |
| pSJ414 | talB + pyrH | 149.79 | 947.48 |
| pSJ415 | talB + hpt | 100.32 | 601.54 |
| pSJ416 | zwf + pyrI | 152.75 | 968.18 |
| pSJ417 | zwf + cysQ | 130.45 | 812.24 |
| pSJ418 | zwf + gmk | 119.39 | 734.90 |
| pSJ419 | zwf + guaB | 210.42 | 1371.47 |
| pSJ420 | zwf + pyrH | 75.35 | 426.92 |

All the documents mentioned in the present invention are incorporated by reference in the present application, as if each document is alone incorporated by reference. In addition, it should be understood that after reading the above-mentioned teaching contents of the present invention, those skilled in the art would be able to make various modifications or amendments to the present invention, and these equivalent forms likewise fall within the scope defined by the appended claims of the present application.

The invention claimed is:

1. A method for increasing the yield of heterologous synthesis of a polyketide 6-deoxyerythronolide B by 20% or more in an E. coli compared to unattenuated E. coli wherein the method comprises:
   (1) attenuating an expression of a target gene in the E. coli for synthesizing the polyketide 6-deoxyerythronolide B;
   wherein, the target gene is selected from:
   (a) a gene for nucleotide synthesis and other metabolism modules: phosphoribosyl glycinamide formyltransferase 2 purT, autoinducer-2ABC transporter lsrC, coproporphyrinogen III dehydrogenase hemN, glucose 6-phosphate-1-dehydrogenase zwf, 6-phosphogluconolactonase pgl, 6-phosphogluconate dehydrogenase gnd, ribulose-5-phosphate 3-epimerase rpe, transaldolase A talA, transaldolase talB, transketolase I tktA, transketolase II tktB, L-xylulose 5-phosphate 3-epimerase ulaE or predicted 6-phosphogluconolactonase yieK;
   (b) a gene for pentose phosphate and glyoxylate pathway modules: predicted lyase yaeR, ribose-5-phosphate isomerase A rpiA, allose-6-phosphate isomerase/ribose-5-phosphate isomerase B rpiB, AICAR transformylase purH, aspartate carbamoyltransferase, catalytic subunit pyrB, aspartate carbamoyltransferase, regulatory subunit pyrI, adenosine-3'(2'),5'-bisphosphate nucleotidase cysQ, dihydroorotase pyrC, guanylate kinase gmk, GMP synthetase guaA, IMP dehydrogenase guaB, nucleoside diphosphate kinase ndk, orotidine-5'-phosphate decarboxylase pyrF, orotate phosphoribosyltransferase pyrE, UMP kinase pyrH or hypoxanthine phosphoribosyltransferase hpt;
   (c) a gene for TCA cycle and oxidative phosphorylation modules: fumarate reductase frdD, fumarate reductase, a subunit frdA, succinate dehydrogenase A sdhA, succinate dehydrogenase B sdhB, succinate dehydrogenase C sdhC, succinate dehydrogenase D sdhD, succinyl-CoA synthetase, β subunit sucC, succinyl-CoA synthetase sucD, cytochrome bo terminal oxidase subunit II cyoA or cytochrome bo terminal oxidase subunit I cyoB;

(d) a gene for carbohydrate metabolism module: pyruvate dehydrogenase aceF, phosphoglucose isomerase pgi, lipoamide dehydrogenase lpdA, polyphosphate kinase ppk, HPr protein of phosphoenolpyruvate-sugar phosphotransferase system ptsH, PTSI protein of phosphoenolpyruvate-sugar phosphotransferase system ptsI, glycolateoxidase, predicted iron-sulfur subunit glcF, glycolate oxidase, FAD-binding subunit glcE, fructose 6-phosphate aldolase 1 fsaA or N-acetylgalactosameine-specific IIC component 2 of PTS system agaW;

(e) a gene for 6-dEB precursor metabolism module: methylmalonyl-CoA mutase scpA, propionate kinase tdcD, 2-ketobutyrate formatelyase/pyruvate formatelyase 4, inactive tdcE, pyruvate formatelyase pflB, formate acetyltransferase 2 pflD, predicted 2,3-dehydroadipyl-CoA hydratase PaaF, acetate kinase ackA, phosphate acetyltransferase/phosphate propionyltransferase pta or pyruvate formatelyase ybiW;

(f) a gene for fatty acid metabolism module: FadJ component of anaerobic fatty acid oxidation complex fadJ, fatty acid oxidation complex, a component fadB, dihydroxyacetone kinase subunit K dhaK1, dihydroxyacetone kinase dhaK2 or dihydroxyacetone kinase subunit M dhaH;

(g) a gene for amino acid and protein synthetic metabolism modules: isopropylmalate isomerase leuC, isopropylmalate isomerase lcuD, 3-phosphoserine/phosphohydroxythreonine aminotransferase scrC, phosphoserine phosphatase scrB, D-3-phosphoglycerate dehydrogenase/a-ketoglutarate reductase serA, glutamate dehydrogenase gdhA or tryptophanase/L-cysteine desulhydrase tnaA; or (h) the combination of frdD+sucC, the combination of lsrC+frdD, the combination of lsrC+sucC, the combination of frdD+rpiA, the combination of talA+guaB or the combination of zwf+guaB; and (2) culturing the E. coli prepared in step (1), thereby synthesizing the polyketide 6-deoxyerythronolide, wherein attenuating the expression of the target gene in the E. coli comprises introducing an interfering molecule that inhibits the expression of the target gene or knocking out the target gene, wherein the interfering molecule that inhibits the expression of the target gene is directed to:

a sequence shown in SEQ ID NO: 179 in talB or a full complementary sequence thereof, a sequence shown in SEQ ID NO: 191 in guaB or a full complementary sequence thereof, a sequence shown in SEQ ID NO: 37 in sucC or a full complementary sequence thereof, a sequence shown in SEQ ID NO: 16 in yjiM or a full complementary sequence thereof, a sequence shown in SEQ ID NO: 19 in dhaK2 or a full complementary sequence thereof, a sequence shown in SEQ ID NO: 41 in glcE or a full complementary sequence thereof, a sequence shown in SEQ ID NO: 51 in serC or a full complementary sequence thereof, a sequence shown in SEQ ID NO: 174 in zwf or a full complementary sequence thereof and a sequence shown in SEQ ID NO: 191 in guaB or a full complementary sequence thereof, or a sequence shown in SEQ ID NO: 178 in talA or a full complementary sequence thereof and a sequence shown in SEQ ID NO: 191 in guaB or a full complementary sequence thereof, and wherein the increasing the yield of heterologous synthesis of a polyketide 6-deoxyerythronolide B is being compared to that of unattenuated E. coli.

2. The method of claim 1, wherein in (1), the target gene is selected from:

(a) a gene for nucleotide synthesis and other metabolism modules: lsrC, zwf, pgl, gnd, rpe, talA, talB, tktA, tktB, ulaE or yieK;

(b) a gene for pentose phosphate and glyoxylate pathway modules: rpiA, purH, pyrB, pyrI, cysQ, pyrC, gmk, guaA, guaB, ndk, pyrF, pyrE, pyrH or hpt;

(c) a gene for TCA cycle and oxidative phosphorylation modules: frdD, frdA, sdhA, sucC or sucD;

(d) a gene for carbohydrate metabolism module: ptsH, ptsI or glcE;

(e) a gene for 6-dEB precursor metabolism module: yjiM, ackA, pta or ybiW;

(f) a gene for fatty acid metabolism module: fadB or dhaK2;

(g) a gene for amino acid and protein synthetic metabolism modules: serC; or (h) the combination of frdD+sucC, the combination of lsrC+frdD, the combination of lsrC+sucC, the combination of talA+guaB or the combination of zwf+guaB.

3. The method of claim 1, wherein the interfering molecule that inhibits the expression of the target gene is an siRNA.

4. The method of claim 3, wherein the siRNA comprises the following structure:

a promoter, a target gene-inhibiting molecule and a terminator.

5. The method of claim 3, wherein the siRNA is included in an expression vector.

6. The method of claim 1, wherein the E. coli is capable of synthesizing the polyketide 6-deoxyerythronolide B.

7. The method of claim 6, wherein in the E. coli, the operon for propionic acid metabolism is knocked out and phosphopantetheinyl transferase gene sfp is integrated into the knockout site; or the operon for propionic acid metabolism is directly knocked out and sfp is incorporated into any non-essential gene or a non-functional DNA sequence region in the genome of the E. coli.

8. The method of claim 7, wherein the E. coli is transformed with a gene encoding polyketide synthetase DEBS2 of Streptomyces erythreus, a gene encoding polyketide synthetase DEBS3 of Streptomyces erythreus, a gene encoding propionyl-CoA carboxylase β-CT subunit, a gene encoding propionyl-CoA carboxylase α-CT subunit and a gene encoding polyketide synthetase DEBS1 of Streptomyces erythreus.

9. The method of claim 4, wherein the structure further comprises a micF sequence between the target gene-inhibiting molecule and the terminator.

10. The method of claim 1, wherein the interfering molecule that inhibits the expression of the target gene further comprises:

a sequence shown in SEQ ID NO: 2 in tdcD or a full complementary sequence thereof, a sequence shown in SEQ ID NO: 4 in scpA or a full complementary sequence thereof,
a sequence shown in SEQ ID NO: 5 in ybiW or a full complementary sequence thereof,
a sequence shown in SEQ ID NO: 6 in pflB or a full complementary sequence thereof,
a sequence shown in SEQ ID NO: 7 in tdcE or a full complementary sequence thereof,
a sequence shown in SEQ ID NO: 8 in pflD or a full complementary sequence thereof,
a sequence shown in SEQ ID NO: 9 in paaF or a full complementary sequence thereof,
a sequence shown in SEQ ID NO: 10 in fadJ or a full complementary sequence thereof and
a sequence shown in SEQ ID NO: 11 in fadB or a full complementary sequence thereof, or
a sequence shown in SEQ ID NO: 12 in ackA or a full complementary sequence thereof and
a sequence shown in SEQ ID NO: 13 in pta or a full complementary sequence thereof,
a sequence shown in SEQ ID NO: 14 in leuD or a full complementary sequence thereof,
a sequence shown in SEQ ID NO: 15 in leuC or a full complementary sequence thereof,
a sequence shown in SEQ ID NO: 17 in purT or a full complementary sequence thereof,
a sequence shown in SEQ ID NO: 18 in dhaK1 or a full complementary sequence thereof,
a sequence shown in SEQ ID NO: 20 in dhaH or a full complementary sequence thereof,
a sequence shown in SEQ ID NO: 21 in ptsH or a full complementary sequence thereof,
a sequence shown in SEQ ID NO: 22 in ptsI or a full complementary sequence thereof,
a sequence shown in SEQ ID NO: 23 in fsaA or a full complementary sequence thereof and
a sequence shown in SEQ ID NO: 24 in ppk or a full complementary sequence thereof, or
a sequence shown in SEQ ID NO: 25 in aceF or a full complementary sequence thereof and
a sequence shown in SEQ ID NO: 26 in cyoA or a full complementary sequence thereof,
a sequence shown in SEQ ID NO: 30 in frdD or a full complementary sequence thereof,
a sequence shown in SEQ ID NO: 31 in frdA or a full complementary sequence thereof,
a sequence shown in SEQ ID NO: 32 in pgi or a full complementary sequence thereof,
a sequence shown in SEQ ID NO: 33 in sdhA or a full complementary sequence thereof,
a sequence shown in SEQ ID NO: 34 in sdhB or a full complementary sequence thereof,
a sequence shown in SEQ ID NO: 35 in sdhC or a full complementary sequence thereof,
a sequence shown in SEQ ID NO: 36 in sdhD or a full complementary sequence thereof,
a sequence shown in SEQ ID NO: 38 in sucD or a full complementary sequence thereof and
a sequence shown in SEQ ID NO: 39 in tnaA or a full complementary sequence thereof, or
a sequence shown in SEQ ID NO: 40 in glcF or a full complementary sequence thereof and
a sequence shown in SEQ ID NO: 42 in yaeR or a full complementary sequence thereof,
a sequence shown in SEQ ID NO: 43 in lsrC or a full complementary sequence thereof,
a sequence shown in SEQ ID NO: 44 in hemN or a full complementary sequence thereof,
a sequence shown in SEQ ID NO: 45 in agaW or a full complementary sequence thereof,
a sequence shown in SEQ ID NO: 46 in gdhA or a full complementary sequence thereof,
a sequence shown in SEQ ID NO: 47 in cyoB or a full complementary sequence thereof,
a sequence shown in SEQ ID NO: 48 in rpiA or a full complementary sequence thereof,
a sequence shown in SEQ ID NO: 49 in rpiB or a full complementary sequence thereof,
a sequence shown in SEQ ID NO: 50 in lpdA or a full complementary sequence thereof and
a sequence shown in SEQ ID NO: 28 in serB or a full complementary sequence thereof, or
a sequence shown in SEQ ID NO: 29 in serA or a full complementary sequence thereof and
a sequence shown in SEQ ID NO: 175 in pgl or a full complementary sequence thereof,
a sequence shown in SEQ ID NO: 176 in gnd or a full complementary sequence thereof,
a sequence shown in SEQ ID NO: 177 in rpe or a full complementary sequence thereof,
a sequence shown in SEQ ID NO: 180 in tktA or a full complementary sequence thereof,
a sequence shown in SEQ ID NO: 181 in tktB or a full complementary sequence thereof,
a sequence shown in SEQ ID NO: 182 in ulaE or a full complementary sequence thereof,
a sequence shown in SEQ ID NO: 183 in yieK or a full complementary sequence thereof,
a sequence shown in SEQ ID NO: 184 in purH or a full complementary sequence thereof,
a sequence shown in SEQ ID NO: 185 in pyrB or a full complementary sequence thereof and
a sequence shown in SEQ ID NO: 186 in pyrI or a full complementary sequence thereof, or
a sequence shown in SEQ ID NO: 187 in cysQ or a full complementary sequence thereof and
a sequence shown in SEQ ID NO: 188 in pyrC or a full complementary sequence thereof,
a sequence shown in SEQ ID NO: 189 in gmk or a full complementary sequence thereof,
a sequence shown in SEQ ID NO: 190 in guaA or a full complementary sequence thereof,
a sequence shown in SEQ ID NO: 192 in ndk or a full complementary sequence thereof,
a sequence shown in SEQ ID NO: 193 in pyrF or a full complementary sequence thereof,
a sequence shown in SEQ ID NO: 194 in pyre or a full complementary sequence thereof,
a sequence shown in SEQ ID NO: 195 in pyrH or a full complementary sequence thereof,
a sequence shown in SEQ ID NO: 196 in hpt or a full complementary sequence thereof.

\* \* \* \* \*

SEQUENCE LISTING

<160> NUMBER OF SEQ ID NOS: 242

<210> SEQ ID NO 1
<211> LENGTH: 25
<212> TYPE: DNA
<213> ORGANISM: Artificial
<220> FEATURE:
<223> OTHER INFORMATION: Target gene binding sequence

<400> SEQUENCE: 1
tacctctggc ggtgataatg gttgc                                           25

<210> SEQ ID NO 2
<211> LENGTH: 24
<212> TYPE: DNA

<213> ORGANISM: Artificial
<220> FEATURE:
<223> OTHER INFORMATION: Target gene binding sequence

<400> SEQUENCE: 2
aacgttaaca tactgataag acat                                              24

<210> SEQ ID NO 3
<211> LENGTH: 24
<212> TYPE: DNA
<213> ORGANISM: Artificial
<220> FEATURE:
<223> OTHER INFORMATION: Target gene binding sequence

<400> SEQUENCE: 3
caaaacaacc ggaaattcat tcat                                              24

<210> SEQ ID NO 4
<211> LENGTH: 24
<212> TYPE: DNA
<213> ORGANISM: Artificial
<220> FEATURE:
<223> OTHER INFORMATION: Target gene binding sequence

<400> SEQUENCE: 4
ttgccactcc tgcacgttag acat                                              24

<210> SEQ ID NO 5
<211> LENGTH: 24
<212> TYPE: DNA
<213> ORGANISM: Artificial
<220> FEATURE:
<223> OTHER INFORMATION: Target gene binding sequence

<400> SEQUENCE: 5
cgtgtccagt ttcagtgtgg tcat                                              24

<210> SEQ ID NO 6
<211> LENGTH: 24
<212> TYPE: DNA
<213> ORGANISM: Artificial
<220> FEATURE:
<223> OTHER INFORMATION: Target gene binding sequence

<400> SEQUENCE: 6
taacttttca ttaagctcgg acat                                              24

<210> SEQ ID NO 7
<211> LENGTH: 24
<212> TYPE: DNA
<213> ORGANISM: Artificial
<220> FEATURE:
<223> OTHER INFORMATION: Target gene binding sequence

<400> SEQUENCE: 7
gctggtatca atatctacct tcat                                              24

<210> SEQ ID NO 8
<211> LENGTH: 24
<212> TYPE: DNA
<213> ORGANISM: Artificial
<220> FEATURE:
<223> OTHER INFORMATION: Target gene binding sequence

<400> SEQUENCE: 8
gaggcgagag atacgattcg tcat                                              24

<210> SEQ ID NO 9
<211> LENGTH: 24
<212> TYPE: DNA
<213> ORGANISM: Artificial
<220> FEATURE:
<223> OTHER INFORMATION: Target gene binding sequence

<400> SEQUENCE: 9
acggctgacg atcagttcgc tcat                                          24

<210> SEQ ID NO 10
<211> LENGTH: 24
<212> TYPE: DNA
<213> ORGANISM: Artificial
<220> FEATURE:
<223> OTHER INFORMATION: Target gene binding sequence

<400> SEQUENCE: 10
ggtaaacgct gatgtcattt ccat                                          24

<210> SEQ ID NO 11
<211> LENGTH: 24
<212> TYPE: DNA
<213> ORGANISM: Artificial
<220> FEATURE:
<223> OTHER INFORMATION: Target gene binding sequence

<400> SEQUENCE: 11
cagggtgtcg cctttgtaaa gcat                                          24

<210> SEQ ID NO 12
<211> LENGTH: 24
<212> TYPE: DNA
<213> ORGANISM: Artificial
<220> FEATURE:
<223> OTHER INFORMATION: Target gene binding sequence

<400> SEQUENCE: 12
aaccagtact aacttactcg acat                                          24

<210> SEQ ID NO 13
<211> LENGTH: 24
<212> TYPE: DNA
<213> ORGANISM: Artificial
<220> FEATURE:
<223> OTHER INFORMATION: Target gene binding sequence

<400> SEQUENCE: 13
gatcagcata ataatacggg acac                                          24

<210> SEQ ID NO 14
<211> LENGTH: 24
<212> TYPE: DNA
<213> ORGANISM: Artificial
<220> FEATURE:
<223> OTHER INFORMATION: Target gene binding sequence

<400> SEQUENCE: 14
gtgtttgata aatttctctg ccat                                          24

<210> SEQ ID NO 15
<211> LENGTH: 24
<212> TYPE: DNA
<213> ORGANISM: Artificial
<220> FEATURE:

```
<223> OTHER INFORMATION: Target gene binding sequence

<400> SEQUENCE: 15
tttttcgtat aacgtcttag ccat                                              24

<210> SEQ ID NO 16
<211> LENGTH: 24
<212> TYPE: DNA
<213> ORGANISM: Artificial
<220> FEATURE:
<223> OTHER INFORMATION: Target gene binding sequence

<400> SEQUENCE: 16
gggtagatcg gtgacaagtg acat                                              24

<210> SEQ ID NO 17
<211> LENGTH: 24
<212> TYPE: DNA
<213> ORGANISM: Artificial
<220> FEATURE:
<223> OTHER INFORMATION: Target gene binding sequence

<400> SEQUENCE: 17
cagcgcagtg cctaataacg tcat                                              24

<210> SEQ ID NO 18
<211> LENGTH: 24
<212> TYPE: DNA
<213> ORGANISM: Artificial
<220> FEATURE:
<223> OTHER INFORMATION: Target gene binding sequence

<400> SEQUENCE: 18
cacatcattg atcaatttt tcat                                               24

<210> SEQ ID NO 19
<211> LENGTH: 24
<212> TYPE: DNA
<213> ORGANISM: Artificial
<220> FEATURE:
<223> OTHER INFORMATION: Target gene binding sequence

<400> SEQUENCE: 19
aatttgagtt ctgctcagtg acat                                              24

<210> SEQ ID NO 20
<211> LENGTH: 24
<212> TYPE: DNA
<213> ORGANISM: Artificial
<220> FEATURE:
<223> OTHER INFORMATION: Target gene binding sequence

<400> SEQUENCE: 20
tgaaactatg accaggttta ccat                                              24

<210> SEQ ID NO 21
<211> LENGTH: 24
<212> TYPE: DNA
<213> ORGANISM: Artificial
<220> FEATURE:
<223> OTHER INFORMATION: Target gene binding sequence

<400> SEQUENCE: 21
aatggtaact tcttgctgga acat                                              24
```

```
<210> SEQ ID NO 22
<211> LENGTH: 24
<212> TYPE: DNA
<213> ORGANISM: Artificial
<220> FEATURE:
<223> OTHER INFORMATION: Target gene binding sequence

<400> SEQUENCE: 22
ggatgctaaa atgcctgaaa tcat                                              24

<210> SEQ ID NO 23
<211> LENGTH: 24
<212> TYPE: DNA
<213> ORGANISM: Artificial
<220> FEATURE:
<223> OTHER INFORMATION: Target gene binding sequence

<400> SEQUENCE: 23
tgaagtatcc agatacagtt ccat                                              24

<210> SEQ ID NO 24
<211> LENGTH: 24
<212> TYPE: DNA
<213> ORGANISM: Artificial
<220> FEATURE:
<223> OTHER INFORMATION: Target gene binding sequence

<400> SEQUENCE: 24
gatgtatagc ttttcctgac ccat                                              24

<210> SEQ ID NO 25
<211> LENGTH: 24
<212> TYPE: DNA
<213> ORGANISM: Artificial
<220> FEATURE:
<223> OTHER INFORMATION: Target gene binding sequence

<400> SEQUENCE: 25
cggtactttg atttcgatag ccat                                              24

<210> SEQ ID NO 26
<211> LENGTH: 24
<212> TYPE: DNA
<213> ORGANISM: Artificial
<220> FEATURE:
<223> OTHER INFORMATION: Target gene binding sequence

<400> SEQUENCE: 26
tttattgtat ttcctgagtc tcat                                              24

<210> SEQ ID NO 27
<211> LENGTH: 39
<212> TYPE: DNA
<213> ORGANISM: Artificial
<220> FEATURE:
<223> OTHER INFORMATION: primer

<400> SEQUENCE: 27
gatgaattcg aattctcagt ccttgatctc gcagatggc                              39

<210> SEQ ID NO 28
<211> LENGTH: 24
<212> TYPE: DNA
<213> ORGANISM: Artificial
<220> FEATURE:
<223> OTHER INFORMATION: Target gene binding sequence
```

```
<400> SEQUENCE: 28
gtcgcaccag gtaatgttag gcat                                      24

<210> SEQ ID NO 29
<211> LENGTH: 24
<212> TYPE: DNA
<213> ORGANISM: Artificial
<220> FEATURE:
<223> OTHER INFORMATION: Target gene binding sequence

<400> SEQUENCE: 29
tttctccagc gataccttg ccat                                       24

<210> SEQ ID NO 30
<211> LENGTH: 24
<212> TYPE: DNA
<213> ORGANISM: Artificial
<220> FEATURE:
<223> OTHER INFORMATION: Target gene binding sequence

<400> SEQUENCE: 30
acgctttgga tttggattaa tcat                                      24

<210> SEQ ID NO 31
<211> LENGTH: 24
<212> TYPE: DNA
<213> ORGANISM: Artificial
<220> FEATURE:
<223> OTHER INFORMATION: Target gene binding sequence

<400> SEQUENCE: 31
aagatcggct tgaaaggttt gcac                                      24

<210> SEQ ID NO 32
<211> LENGTH: 24
<212> TYPE: DNA
<213> ORGANISM: Artificial
<220> FEATURE:
<223> OTHER INFORMATION: Target gene binding sequence

<400> SEQUENCE: 32
ctgcgttgga ttgatgtttt tcat                                      24

<210> SEQ ID NO 33
<211> LENGTH: 24
<212> TYPE: DNA
<213> ORGANISM: Artificial
<220> FEATURE:
<223> OTHER INFORMATION: Target gene binding sequence

<400> SEQUENCE: 33
aaattctctg actggcaatt tcat                                      24

<210> SEQ ID NO 34
<211> LENGTH: 24
<212> TYPE: DNA
<213> ORGANISM: Artificial
<220> FEATURE:
<223> OTHER INFORMATION: Target gene binding sequence

<400> SEQUENCE: 34
ataaattgaa aactcgagtc tcat                                      24

<210> SEQ ID NO 35
<211> LENGTH: 24
```

```
<212> TYPE: DNA
<213> ORGANISM: Artificial
<220> FEATURE:
<223> OTHER INFORMATION: Target gene binding sequence

<400> SEQUENCE: 35
ttgttttttc acatttctta tcat                                          24

<210> SEQ ID NO 36
<211> LENGTH: 24
<212> TYPE: DNA
<213> ORGANISM: Artificial
<220> FEATURE:
<223> OTHER INFORMATION: Target gene binding sequence

<400> SEQUENCE: 36
taatgcggag gcgttgctta ccat                                          24

<210> SEQ ID NO 37
<211> LENGTH: 24
<212> TYPE: DNA
<213> ORGANISM: Artificial
<220> FEATURE:
<223> OTHER INFORMATION: Target gene binding sequence

<400> SEQUENCE: 37
tgcctgatat tcatgtaagt tcat                                          24

<210> SEQ ID NO 38
<211> LENGTH: 24
<212> TYPE: DNA
<213> ORGANISM: Artificial
<220> FEATURE:
<223> OTHER INFORMATION: Target gene binding sequence

<400> SEQUENCE: 38
gtttttatcg attaaaatgg acat                                          24

<210> SEQ ID NO 39
<211> LENGTH: 24
<212> TYPE: DNA
<213> ORGANISM: Artificial
<220> FEATURE:
<223> OTHER INFORMATION: Target gene binding sequence

<400> SEQUENCE: 39
agggagatgt ttaaagtttt ccat                                          24

<210> SEQ ID NO 40
<211> LENGTH: 24
<212> TYPE: DNA
<213> ORGANISM: Artificial
<220> FEATURE:
<223> OTHER INFORMATION: Target gene binding sequence

<400> SEQUENCE: 40
ctcttcagtt aattgggttt gcat                                          24

<210> SEQ ID NO 41
<211> LENGTH: 24
<212> TYPE: DNA
<213> ORGANISM: Artificial
<220> FEATURE:
<223> OTHER INFORMATION: Target gene binding sequence

<400> SEQUENCE: 41
```

```
gctgtaatca cactcgcgta gcat                                          24

<210> SEQ ID NO 42
<211> LENGTH: 24
<212> TYPE: DNA
<213> ORGANISM: Artificial
<220> FEATURE:
<223> OTHER INFORMATION: Target gene binding sequence

<400> SEQUENCE: 42
gtgaacctgt tttaaaccca gcat                                          24

<210> SEQ ID NO 43
<211> LENGTH: 24
<212> TYPE: DNA
<213> ORGANISM: Artificial
<220> FEATURE:
<223> OTHER INFORMATION: Target gene binding sequence

<400> SEQUENCE: 43
gttgttctga ataaacttca gcat                                          24

<210> SEQ ID NO 44
<211> LENGTH: 24
<212> TYPE: DNA
<213> ORGANISM: Artificial
<220> FEATURE:
<223> OTHER INFORMATION: primer

<400> SEQUENCE: 44
ccagtcgatt tgctgtacag acat                                          24

<210> SEQ ID NO 45
<211> LENGTH: 24
<212> TYPE: DNA
<213> ORGANISM: Artificial
<220> FEATURE:
<223> OTHER INFORMATION: Target gene binding sequence

<400> SEQUENCE: 45
tgcctgcaac aggctgattt ccat                                          24

<210> SEQ ID NO 46
<211> LENGTH: 24
<212> TYPE: DNA
<213> ORGANISM: Artificial
<220> FEATURE:
<223> OTHER INFORMATION: Target gene binding sequence

<400> SEQUENCE: 46
ctccagagaa tatgtctgat ccat                                          24

<210> SEQ ID NO 47
<211> LENGTH: 24
<212> TYPE: DNA
<213> ORGANISM: Artificial
<220> FEATURE:
<223> OTHER INFORMATION: Target gene binding sequence

<400> SEQUENCE: 47
atgttcggaa aattatcact tgat                                          24

<210> SEQ ID NO 48
<211> LENGTH: 24
<212> TYPE: DNA
<213> ORGANISM: Artificial
```

```
<220> FEATURE:
<223> OTHER INFORMATION: Target gene binding sequence

<400> SEQUENCE: 48
ttttttcaat tcatcctgcg tcat                                            24

<210> SEQ ID NO 49
<211> LENGTH: 24
<212> TYPE: DNA
<213> ORGANISM: Artificial
<220> FEATURE:
<223> OTHER INFORMATION: Target gene binding sequence

<400> SEQUENCE: 49
acagccaaat gcaatctttt tcat                                            24

<210> SEQ ID NO 50
<211> LENGTH: 24
<212> TYPE: DNA
<213> ORGANISM: Artificial
<220> FEATURE:
<223> OTHER INFORMATION: Target gene binding sequence

<400> SEQUENCE: 50
ctgagttttg atttcagtac tcat                                            24

<210> SEQ ID NO 51
<211> LENGTH: 24
<212> TYPE: DNA
<213> ORGANISM: Artificial
<220> FEATURE:
<223> OTHER INFORMATION: Target gene binding sequence

<400> SEQUENCE: 51
actaaaattg aagatttgag ccat                                            24

<210> SEQ ID NO 52
<211> LENGTH: 322
<212> TYPE: DNA
<213> ORGANISM: Artificial
<220> FEATURE:
<223> OTHER INFORMATION: fusion gene

<400> SEQUENCE: 52
catatgggat cctaacaccg tgcgtgttga ctatttacc tctggcggtg ataatggttg       60
ccaccataat aaatgcacgt ttcattttct gttgggccat tgcattgcca ctgattttcc    120
aacatataaa aagacaagcc cgaacagtcg tccgggcttt ttttctcgag ctcgagccag    180
gcatcaaata aaacgaaagg ctcagtcgaa agactgggcc tttcgtttta tctgttttg     240 tcggtgaacg ctctctacta gagtcacact ggctcacctt cgggtgggcc tttctgcgtt    300
tataactagt agatctaagc tt                                             322

<210> SEQ ID NO 53
<211> LENGTH: 29
<212> TYPE: DNA
<213> ORGANISM: Artificial
<220> FEATURE:
<223> OTHER INFORMATION: primer

<400> SEQUENCE: 53
cccaagcttc tgaaacctca ggcatttga                                       29

<210> SEQ ID NO 54
```

```
<211> LENGTH: 28
<212> TYPE: DNA
<213> ORGANISM: Artificial
<220> FEATURE:
<223> OTHER INFORMATION: primer

<400> SEQUENCE: 54
cgggatccgc gcaacgcaat taatgtaa                                      28

<210> SEQ ID NO 55
<211> LENGTH: 48
<212> TYPE: DNA
<213> ORGANISM: Artificial
<220> FEATURE:
<223> OTHER INFORMATION: primer

<400> SEQUENCE: 55
aacgttaaca tactgataag acattttctg ttgggccatt gcattgcc                48

<210> SEQ ID NO 56
<211> LENGTH: 49
<212> TYPE: DNA
<213> ORGANISM: Artificial
<220> FEATURE:
<223> OTHER INFORMATION: primer

<400> SEQUENCE: 56
atgtcttatc agtatgttaa cgttgcaacc attatcaccg ccagaggta               49

<210> SEQ ID NO 57
<211> LENGTH: 48
<212> TYPE: DNA
<213> ORGANISM: Artificial
<220> FEATURE:
<223> OTHER INFORMATION: primer

<400> SEQUENCE: 57
caaaacaacc ggaaattcat tcattttctg ttgggccatt gcattgcc                48

<210> SEQ ID NO 58
<211> LENGTH: 49
<212> TYPE: DNA
<213> ORGANISM: Artificial
<220> FEATURE:
<223> OTHER INFORMATION: primer

<400> SEQUENCE: 58
atgaatgaat ttccggttgt tttggcaacc attatcaccg ccagaggta               49

<210> SEQ ID NO 59
<211> LENGTH: 48
<212> TYPE: DNA
<213> ORGANISM: Artificial
<220> FEATURE:
<223> OTHER INFORMATION: primer

<400> SEQUENCE: 59
ttgccactcc tgcacgttag acattttctg ttgggccatt gcattgcc                48

<210> SEQ ID NO 60
<211> LENGTH: 49
<212> TYPE: DNA
<213> ORGANISM: Artificial
<220> FEATURE:
<223> OTHER INFORMATION: primer

<400> SEQUENCE: 60
```

```
atgtctaacg tgcaggagtg gcaagcaacc attatcaccg ccagaggta          49

<210> SEQ ID NO 61
<211> LENGTH: 48
<212> TYPE: DNA
<213> ORGANISM: Artificial
<220> FEATURE:
<223> OTHER INFORMATION: primer

<400> SEQUENCE: 61
cgtgtccagt tcagtgtgg tcatttctg ttgggccatt gcattgcc             48

<210> SEQ ID NO 62
<211> LENGTH: 49
<212> TYPE: DNA
<213> ORGANISM: Artificial
<220> FEATURE:
<223> OTHER INFORMATION: primer

<400> SEQUENCE: 62
atgaccacac tgaaactgga cacggcaacc attatcaccg ccagaggta          49

<210> SEQ ID NO 63
<211> LENGTH: 48
<212> TYPE: DNA
<213> ORGANISM: Artificial
<220> FEATURE:
<223> OTHER INFORMATION: primer

<400> SEQUENCE: 63
taacttttca ttaagctcgg acattttctg ttgggccatt gcattgcc           48

<210> SEQ ID NO 64
<211> LENGTH: 49
<212> TYPE: DNA
<213> ORGANISM: Artificial
<220> FEATURE:
<223> OTHER INFORMATION: primer

<400> SEQUENCE: 64
atgtccgagc ttaatgaaaa gttagcaacc attatcaccg ccagaggta          49

<210> SEQ ID NO 65
<211> LENGTH: 48
<212> TYPE: DNA
<213> ORGANISM: Artificial
<220> FEATURE:
<223> OTHER INFORMATION: primer

<400> SEQUENCE: 65
gctggtatca atatctacct tcattttctg ttgggccatt gcattgcc           48

<210> SEQ ID NO 66
<211> LENGTH: 49
<212> TYPE: DNA
<213> ORGANISM: Artificial
<220> FEATURE:
<223> OTHER INFORMATION: primer

<400> SEQUENCE: 66
atgaaggtag atattgatac cagcgcaacc attatcaccg ccagaggta          49

<210> SEQ ID NO 67
<211> LENGTH: 48
<212> TYPE: DNA
```

<213> ORGANISM: Artificial
<220> FEATURE:
<223> OTHER INFORMATION: primer

<400> SEQUENCE: 67
gaggcgagag atacgattcg tcattttctg ttgggccatt gcattgcc                48

<210> SEQ ID NO 68
<211> LENGTH: 49
<212> TYPE: DNA
<213> ORGANISM: Artificial
<220> FEATURE:
<223> OTHER INFORMATION: primer

<400> SEQUENCE: 68
atgacgaatc gtatctctcg cctcgcaacc attatcaccg ccagaggta               49

<210> SEQ ID NO 69
<211> LENGTH: 48
<212> TYPE: DNA
<213> ORGANISM: Artificial
<220> FEATURE:
<223> OTHER INFORMATION: primer

<400> SEQUENCE: 69
acggctgacg atcagttcgc tcattttctg ttgggccatt gcattgcc                48

<210> SEQ ID NO 70
<211> LENGTH: 49
<212> TYPE: DNA
<213> ORGANISM: Artificial
<220> FEATURE:
<223> OTHER INFORMATION: primer

<400> SEQUENCE: 70
atgagcgaac tgatcgtcag ccgtgcaacc attatcaccg ccagaggta               49

<210> SEQ ID NO 71
<211> LENGTH: 48
<212> TYPE: DNA
<213> ORGANISM: Artificial
<220> FEATURE:
<223> OTHER INFORMATION: primer

<400> SEQUENCE: 71
ggtaaacgct gatgtcattt ccattttctg ttgggccatt gcattgcc                48

<210> SEQ ID NO 72
<211> LENGTH: 49
<212> TYPE: DNA
<213> ORGANISM: Artificial
<220> FEATURE:
<223> OTHER INFORMATION: primer

<400> SEQUENCE: 72
atggaaatga catcagcgtt taccgcaacc attatcaccg ccagaggta               49

<210> SEQ ID NO 73
<211> LENGTH: 48
<212> TYPE: DNA
<213> ORGANISM: Artificial
<220> FEATURE:
<223> OTHER INFORMATION: primer

<400> SEQUENCE: 73
cagggtgtcg cctttgtaaa gcattttctg ttgggccatt gcattgcc                48

<210> SEQ ID NO 74
<211> LENGTH: 49
<212> TYPE: DNA
<213> ORGANISM: Artificial
<220> FEATURE:
<223> OTHER INFORMATION: primer

<400> SEQUENCE: 74
atgctttaca aaggcgacac cctggcaacc attatcaccg ccagaggta          49

<210> SEQ ID NO 75
<211> LENGTH: 48
<212> TYPE: DNA
<213> ORGANISM: Artificial
<220> FEATURE:
<223> OTHER INFORMATION: primer

<400> SEQUENCE: 75
aaccagtact aacttactcg acatttctg ttgggccatt gcattgcc             48

<210> SEQ ID NO 76
<211> LENGTH: 49
<212> TYPE: DNA
<213> ORGANISM: Artificial
<220> FEATURE:
<223> OTHER INFORMATION: primer

<400> SEQUENCE: 76
atgtcgagta agttagtact ggttgcaacc attatcaccg ccagaggta          49

<210> SEQ ID NO 77
<211> LENGTH: 48
<212> TYPE: DNA
<213> ORGANISM: Artificial
<220> FEATURE:
<223> OTHER INFORMATION: primer

<400> SEQUENCE: 77
gatcagcata ataatacggg acactttctg ttgggccatt gcattgcc           48

<210> SEQ ID NO 78
<211> LENGTH: 49
<212> TYPE: DNA
<213> ORGANISM: Artificial
<220> FEATURE:
<223> OTHER INFORMATION: primer

<400> SEQUENCE: 78
gtgtcccgta ttattatgct gatcgcaacc attatcaccg ccagaggta          49

<210> SEQ ID NO 79
<211> LENGTH: 48
<212> TYPE: DNA
<213> ORGANISM: Artificial
<220> FEATURE:
<223> OTHER INFORMATION: primer

<400> SEQUENCE: 79
gtgtttgata aatttctctg ccatttctg ttgggccatt gcattgcc             48

<210> SEQ ID NO 80
<211> LENGTH: 49
<212> TYPE: DNA
<213> ORGANISM: Artificial
<220> FEATURE:

<223> OTHER INFORMATION: primer

<400> SEQUENCE: 80
atggcagaga aatttatcaa acacgcaacc attatcaccg ccagaggta         49

<210> SEQ ID NO 81
<211> LENGTH: 48
<212> TYPE: DNA
<213> ORGANISM: Artificial
<220> FEATURE:
<223> OTHER INFORMATION: primer

<400> SEQUENCE: 81
tttttcgtat aacgtcttag ccattttctg ttgggccatt gcattgcc          48

<210> SEQ ID NO 82
<211> LENGTH: 49
<212> TYPE: DNA
<213> ORGANISM: Artificial
<220> FEATURE:
<223> OTHER INFORMATION: primer

<400> SEQUENCE: 82
atggctaaga cgttatacga aaaagcaacc attatcaccg ccagaggta         49

<210> SEQ ID NO 83
<211> LENGTH: 48
<212> TYPE: DNA
<213> ORGANISM: Artificial
<220> FEATURE:
<223> OTHER INFORMATION: primer

<400> SEQUENCE: 83
gggtagatcg gtgacaagtg acattttctg ttgggccatt gcattgcc          48

<210> SEQ ID NO 84
<211> LENGTH: 49
<212> TYPE: DNA
<213> ORGANISM: Artificial
<220> FEATURE:
<223> OTHER INFORMATION: primer

<400> SEQUENCE: 84
atgtcacttg tcaccgatct acccgcaacc attatcaccg ccagaggta         49

<210> SEQ ID NO 85
<211> LENGTH: 48
<212> TYPE: DNA
<213> ORGANISM: Artificial
<220> FEATURE:
<223> OTHER INFORMATION: primer

<400> SEQUENCE: 85
cagcgcagtg cctaataacg tcattttctg ttgggccatt gcattgcc          48

<210> SEQ ID NO 86
<211> LENGTH: 49
<212> TYPE: DNA
<213> ORGANISM: Artificial
<220> FEATURE:
<223> OTHER INFORMATION: primer

<400> SEQUENCE: 86
atgacgttat taggcactgc gctggcaacc attatcaccg ccagaggta         49

<210> SEQ ID NO 87
<211> LENGTH: 48
<212> TYPE: DNA
<213> ORGANISM: Artificial
<220> FEATURE:
<223> OTHER INFORMATION: primer

<400> SEQUENCE: 87
cacatcattg atcaattttt tcatttctg ttgggccatt gcattgcc        48

<210> SEQ ID NO 88
<211> LENGTH: 49
<212> TYPE: DNA
<213> ORGANISM: Artificial
<220> FEATURE:
<223> OTHER INFORMATION: primer

<400> SEQUENCE: 88
atgaaaaaat tgatcaatga tgtggcaacc attatcaccg ccagaggta       49

<210> SEQ ID NO 89
<211> LENGTH: 48
<212> TYPE: DNA
<213> ORGANISM: Artificial
<220> FEATURE:
<223> OTHER INFORMATION: primer

<400> SEQUENCE: 89
aatttgagtt ctgctcagtg acattttctg ttgggccatt gcattgcc        48

<210> SEQ ID NO 90
<211> LENGTH: 49
<212> TYPE: DNA
<213> ORGANISM: Artificial
<220> FEATURE:
<223> OTHER INFORMATION: primer

<400> SEQUENCE: 90
atgtcactga gcagaactca aattgcaacc attatcaccg ccagaggta       49

<210> SEQ ID NO 91
<211> LENGTH: 48
<212> TYPE: DNA
<213> ORGANISM: Artificial
<220> FEATURE:
<223> OTHER INFORMATION: primer

<400> SEQUENCE: 91
tgaaactatg accaggttta ccatttctg ttgggccatt gcattgcc         48

<210> SEQ ID NO 92
<211> LENGTH: 49
<212> TYPE: DNA
<213> ORGANISM: Artificial
<220> FEATURE:
<223> OTHER INFORMATION: primer

<400> SEQUENCE: 92
atggtaaacc tggtcatagt ttcagcaacc attatcaccg ccagaggta       49

<210> SEQ ID NO 93
<211> LENGTH: 48
<212> TYPE: DNA
<213> ORGANISM: Artificial
<220> FEATURE:
<223> OTHER INFORMATION: primer

<400> SEQUENCE: 93
aatggtaact tcttgctgga acattttctg ttgggccatt gcattgcc            48

<210> SEQ ID NO 94
<211> LENGTH: 49
<212> TYPE: DNA
<213> ORGANISM: Artificial
<220> FEATURE:
<223> OTHER INFORMATION: primer

<400> SEQUENCE: 94
atgttccagc aagaagttac cattgcaacc attatcaccg ccagaggta           49

<210> SEQ ID NO 95
<211> LENGTH: 48
<212> TYPE: DNA
<213> ORGANISM: Artificial
<220> FEATURE:
<223> OTHER INFORMATION: primer

<400> SEQUENCE: 95
ggatgctaaa atgcctgaaa tcattttctg ttgggccatt gcattgcc            48

<210> SEQ ID NO 96
<211> LENGTH: 49
<212> TYPE: DNA
<213> ORGANISM: Artificial
<220> FEATURE:
<223> OTHER INFORMATION: primer

<400> SEQUENCE: 96
atgatttcag gcattttagc atccgcaacc attatcaccg ccagaggta           49

<210> SEQ ID NO 97
<211> LENGTH: 48
<212> TYPE: DNA
<213> ORGANISM: Artificial
<220> FEATURE:
<223> OTHER INFORMATION: primer

<400> SEQUENCE: 97
tgaagtatcc agatacagtt ccattttctg ttgggccatt gcattgcc            48

<210> SEQ ID NO 98
<211> LENGTH: 49
<212> TYPE: DNA
<213> ORGANISM: Artificial
<220> FEATURE:
<223> OTHER INFORMATION: primer

<400> SEQUENCE: 98
atggaactgt atctggatac ttcagcaacc attatcaccg ccagaggta           49

<210> SEQ ID NO 99
<211> LENGTH: 48
<212> TYPE: DNA
<213> ORGANISM: Artificial
<220> FEATURE:
<223> OTHER INFORMATION: primer

<400> SEQUENCE: 99
gatgtatagc ttttcctgac ccattttctg ttgggccatt gcattgcc            48

<210> SEQ ID NO 100
<211> LENGTH: 49

<212> TYPE: DNA
<213> ORGANISM: Artificial
<220> FEATURE:
<223> OTHER INFORMATION: primer

<400> SEQUENCE: 100
atgggtcagg aaaagctata catcgcaacc attatcaccg ccagaggta            49

<210> SEQ ID NO 101
<211> LENGTH: 48
<212> TYPE: DNA
<213> ORGANISM: Artificial
<220> FEATURE:
<223> OTHER INFORMATION: primer

<400> SEQUENCE: 101
cggtactttg atttcgatag ccattttctg ttgggccatt gcattgcc             48

<210> SEQ ID NO 102
<211> LENGTH: 49
<212> TYPE: DNA
<213> ORGANISM: Artificial
<220> FEATURE:
<223> OTHER INFORMATION: primer

<400> SEQUENCE: 102
atggctatcg aaatcaaagt accggcaacc attatcaccg ccagaggta            49

<210> SEQ ID NO 103
<211> LENGTH: 48
<212> TYPE: DNA
<213> ORGANISM: Artificial
<220> FEATURE:
<223> OTHER INFORMATION: primer

<400> SEQUENCE: 103
tttattgtat ttcctgagtc tcattttctg ttgggccatt gcattgcc             48

<210> SEQ ID NO 104
<211> LENGTH: 49
<212> TYPE: DNA
<213> ORGANISM: Artificial
<220> FEATURE:
<223> OTHER INFORMATION: primer

<400> SEQUENCE: 104
atgagactca ggaaatacaa taaagcaacc attatcaccg ccagaggta            49

<210> SEQ ID NO 105
<211> LENGTH: 48
<212> TYPE: DNA
<213> ORGANISM: Artificial
<220> FEATURE:
<223> OTHER INFORMATION: primer

<400> SEQUENCE: 105
acgctttgga tttggattaa tcattttctg ttgggccatt gcattgcc             48

<210> SEQ ID NO 106
<211> LENGTH: 49
<212> TYPE: DNA
<213> ORGANISM: Artificial
<220> FEATURE:
<223> OTHER INFORMATION: primer

<400> SEQUENCE: 106

```
atgattaatc caaatccaaa gcgtgcaacc attatcaccg ccagaggta         49
```

<210> SEQ ID NO 107
<211> LENGTH: 48
<212> TYPE: DNA
<213> ORGANISM: Artificial
<220> FEATURE:
<223> OTHER INFORMATION: primer

<400> SEQUENCE: 107

```
aagatcggct tgaaaggttt gcactttctg ttgggccatt gcattgcc          48
```

<210> SEQ ID NO 108
<211> LENGTH: 49
<212> TYPE: DNA
<213> ORGANISM: Artificial
<220> FEATURE:
<223> OTHER INFORMATION: primer

<400> SEQUENCE: 108

```
gtgcaaacct ttcaagccga tcttgcaacc attatcaccg ccagaggta         49
```

<210> SEQ ID NO 109
<211> LENGTH: 48
<212> TYPE: DNA
<213> ORGANISM: Artificial
<220> FEATURE:
<223> OTHER INFORMATION: primer

<400> SEQUENCE: 109

```
ctgcgttgga ttgatgtttt tcattttctg ttgggccatt gcattgcc          48
```

<210> SEQ ID NO 110
<211> LENGTH: 49
<212> TYPE: DNA
<213> ORGANISM: Artificial
<220> FEATURE:
<223> OTHER INFORMATION: primer

<400> SEQUENCE: 110

```
atgaaaaaca tcaatccaac gcaggcaacc attatcaccg ccagaggta         49
```

<210> SEQ ID NO 111
<211> LENGTH: 48
<212> TYPE: DNA
<213> ORGANISM: Artificial
<220> FEATURE:
<223> OTHER INFORMATION: primer

<400> SEQUENCE: 111

```
aaattctctg actggcaatt tcattttctg ttgggccatt gcattgcc          48
```

<210> SEQ ID NO 112
<211> LENGTH: 49
<212> TYPE: DNA
<213> ORGANISM: Artificial
<220> FEATURE:
<223> OTHER INFORMATION: primer

<400> SEQUENCE: 112

```
atgaaattgc cagtcagaga atttgcaacc attatcaccg ccagaggta         49
```

<210> SEQ ID NO 113
<211> LENGTH: 48
<212> TYPE: DNA
<213> ORGANISM: Artificial

-continued

```
<220> FEATURE:
<223> OTHER INFORMATION: primer

<400> SEQUENCE: 113
ataaattgaa aactcgagtc tcattttctg ttgggccatt gcattgcc         48

<210> SEQ ID NO 114
<211> LENGTH: 49
<212> TYPE: DNA
<213> ORGANISM: Artificial
<220> FEATURE:
<223> OTHER INFORMATION: primer

<400> SEQUENCE: 114
atgagactcg agttttcaat ttatgcaacc attatcaccg ccagaggta        49

<210> SEQ ID NO 115
<211> LENGTH: 48
<212> TYPE: DNA
<213> ORGANISM: Artificial
<220> FEATURE:
<223> OTHER INFORMATION: primer

<400> SEQUENCE: 115 ttgtttttc acatttctta tcattttctg ttgggccatt gcattgcc          48

<210> SEQ ID NO 116
<211> LENGTH: 49
<212> TYPE: DNA
<213> ORGANISM: Artificial
<220> FEATURE:
<223> OTHER INFORMATION: primer

<400> SEQUENCE: 116
atgataagaa atgtgaaaaa acaagcaacc attatcaccg ccagaggta        49

<210> SEQ ID NO 117
<211> LENGTH: 48
<212> TYPE: DNA
<213> ORGANISM: Artificial
<220> FEATURE:
<223> OTHER INFORMATION: primer

<400> SEQUENCE: 117
taatgcggag gcgttgctta ccattttctg ttgggccatt gcattgcc         48

<210> SEQ ID NO 118
<211> LENGTH: 49
<212> TYPE: DNA
<213> ORGANISM: Artificial
<220> FEATURE:
<223> OTHER INFORMATION: primer

<400> SEQUENCE: 118
atggtaagca acgcctccgc attagcaacc attatcaccg ccagaggta        49

<210> SEQ ID NO 119
<211> LENGTH: 48
<212> TYPE: DNA
<213> ORGANISM: Artificial
<220> FEATURE:
<223> OTHER INFORMATION: primer

<400> SEQUENCE: 119
tgcctgatat tcatgtaagt tcattttctg ttgggccatt gcattgcc         48
```

<210> SEQ ID NO 120
<211> LENGTH: 49
<212> TYPE: DNA
<213> ORGANISM: Artificial
<220> FEATURE:
<223> OTHER INFORMATION: primer

<400> SEQUENCE: 120
atgaacttac atgaatatca ggcagcaacc attatcaccg ccagaggta          49

<210> SEQ ID NO 121
<211> LENGTH: 48
<212> TYPE: DNA
<213> ORGANISM: Artificial
<220> FEATURE:
<223> OTHER INFORMATION: primer

<400> SEQUENCE: 121
gtttttatcg attaaaatgg acattttctg ttgggccatt gcattgcc          48

<210> SEQ ID NO 122
<211> LENGTH: 49
<212> TYPE: DNA
<213> ORGANISM: Artificial
<220> FEATURE:
<223> OTHER INFORMATION: primer

<400> SEQUENCE: 122
atgtccattt taatcgataa aaacgcaacc attatcaccg ccagaggta          49

<210> SEQ ID NO 123
<211> LENGTH: 48
<212> TYPE: DNA
<213> ORGANISM: Artificial
<220> FEATURE:
<223> OTHER INFORMATION: primer

<400> SEQUENCE: 123
agggagatgt ttaaagtttt ccattttctg ttgggccatt gcattgcc          48

<210> SEQ ID NO 124
<211> LENGTH: 49
<212> TYPE: DNA
<213> ORGANISM: Artificial
<220> FEATURE:
<223> OTHER INFORMATION: primer

<400> SEQUENCE: 124
atggaaaact ttaaacatct ccctgcaacc attatcaccg ccagaggta          49

<210> SEQ ID NO 125
<211> LENGTH: 48
<212> TYPE: DNA
<213> ORGANISM: Artificial
<220> FEATURE:
<223> OTHER INFORMATION: primer

<400> SEQUENCE: 125
ctcttcagtt aattgggttt gcattttctg ttgggccatt gcattgcc          48

<210> SEQ ID NO 126
<211> LENGTH: 49
<212> TYPE: DNA
<213> ORGANISM: Artificial
<220> FEATURE:
<223> OTHER INFORMATION: primer

<400> SEQUENCE: 126
atgcaaaccc aattaactga agaggcaacc attatcaccg ccagaggta          49

<210> SEQ ID NO 127
<211> LENGTH: 48
<212> TYPE: DNA
<213> ORGANISM: Artificial
<220> FEATURE:
<223> OTHER INFORMATION: primer

<400> SEQUENCE: 127
gctgtaatca cactcgcgta gcattttctg ttgggccatt gcattgcc            48

<210> SEQ ID NO 128
<211> LENGTH: 49
<212> TYPE: DNA
<213> ORGANISM: Artificial
<220> FEATURE:
<223> OTHER INFORMATION: primer

<400> SEQUENCE: 128
atgctacgcg agtgtgatta cagcgcaacc attatcaccg ccagaggta          49

<210> SEQ ID NO 129
<211> LENGTH: 48
<212> TYPE: DNA
<213> ORGANISM: Artificial
<220> FEATURE:
<223> OTHER INFORMATION: primer

<400> SEQUENCE: 129
gtgaacctgt tttaaaccca gcattttctg ttgggccatt gcattgcc            48

<210> SEQ ID NO 130
<211> LENGTH: 49
<212> TYPE: DNA
<213> ORGANISM: Artificial
<220> FEATURE:
<223> OTHER INFORMATION: primer

<400> SEQUENCE: 130
atgctgggtt taaaacaggt tcacgcaacc attatcaccg ccagaggta          49

<210> SEQ ID NO 131
<211> LENGTH: 48
<212> TYPE: DNA
<213> ORGANISM: Artificial
<220> FEATURE:
<223> OTHER INFORMATION: primer

<400> SEQUENCE: 131
gttgttctga ataaacttca gcattttctg ttgggccatt gcattgcc            48

<210> SEQ ID NO 132
<211> LENGTH: 49
<212> TYPE: DNA
<213> ORGANISM: Artificial
<220> FEATURE:
<223> OTHER INFORMATION: primer

<400> SEQUENCE: 132
atgctgaagt ttattcagaa caacgcaacc attatcaccg ccagaggta          49

<210> SEQ ID NO 133

```
<211> LENGTH: 48
<212> TYPE: DNA
<213> ORGANISM: Artificial
<220> FEATURE:
<223> OTHER INFORMATION: primer

<400> SEQUENCE: 133
ccagtcgatt tgctgtacag acatttctg ttgggccatt gcattgcc            48

<210> SEQ ID NO 134
<211> LENGTH: 49
<212> TYPE: DNA
<213> ORGANISM: Artificial
<220> FEATURE:
<223> OTHER INFORMATION: primer

<400> SEQUENCE: 134
atgtctgtac agcaaatcga ctgggcaacc attatcaccg ccagaggta            49

<210> SEQ ID NO 135
<211> LENGTH: 48
<212> TYPE: DNA
<213> ORGANISM: Artificial
<220> FEATURE:
<223> OTHER INFORMATION: primer

<400> SEQUENCE: 135
tgcctgcaac aggctgattt ccattttctg ttgggccatt gcattgcc            48

<210> SEQ ID NO 136
<211> LENGTH: 49
<212> TYPE: DNA
<213> ORGANISM: Artificial
<220> FEATURE:
<223> OTHER INFORMATION: primer

<400> SEQUENCE: 136
atggaaatca gcctgttgca ggcagcaacc attatcaccg ccagaggta            49

<210> SEQ ID NO 137
<211> LENGTH: 44
<212> TYPE: DNA
<213> ORGANISM: Artificial
<220> FEATURE:
<223> OTHER INFORMATION: primer

<400> SEQUENCE: 137
ctccagagaa tatgtctgat ccattttctg ttgggccatt gcat            44

<210> SEQ ID NO 138
<211> LENGTH: 44
<212> TYPE: DNA
<213> ORGANISM: Artificial
<220> FEATURE:
<223> OTHER INFORMATION: primer

<400> SEQUENCE: 138
atggatcaga catattctct ggaggcaacc attatcaccg ccag            44

<210> SEQ ID NO 139
<211> LENGTH: 32
<212> TYPE: DNA
<213> ORGANISM: Artificial
<220> FEATURE:
<223> OTHER INFORMATION: primer

<400> SEQUENCE: 139
```

```
catgccatgg atatgcgcaa ggtgctcatc gc                                32
```

<210> SEQ ID NO 140
<211> LENGTH: 44
<212> TYPE: DNA
<213> ORGANISM: Artificial
<220> FEATURE:
<223> OTHER INFORMATION: primer

<400> SEQUENCE: 140

```
atcaagtgat aattttccga acattttctg ttgggccatt gcat                  44
```

<210> SEQ ID NO 141
<211> LENGTH: 44
<212> TYPE: DNA
<213> ORGANISM: Artificial
<220> FEATURE:
<223> OTHER INFORMATION: primer

<400> SEQUENCE: 141

```
atgttcggaa aattatcact tgatgcaacc attatcaccg ccag                  44
```

<210> SEQ ID NO 142
<211> LENGTH: 44
<212> TYPE: DNA
<213> ORGANISM: Artificial
<220> FEATURE:
<223> OTHER INFORMATION: primer

<400> SEQUENCE: 142

```
tttttttcaat tcatcctgcg tcattttctg ttgggccatt gcat                 44
```

<210> SEQ ID NO 143
<211> LENGTH: 44
<212> TYPE: DNA
<213> ORGANISM: Artificial
<220> FEATURE:
<223> OTHER INFORMATION: primer

<400> SEQUENCE: 143

```
atgacgcagg atgaattgaa aaaagcaacc attatcaccg ccag                  44
```

<210> SEQ ID NO 144
<211> LENGTH: 44
<212> TYPE: DNA
<213> ORGANISM: Artificial
<220> FEATURE:
<223> OTHER INFORMATION: primer

<400> SEQUENCE: 144

```
acagccaaat gcaatctttt tcattttctg ttgggccatt gcat                  44
```

<210> SEQ ID NO 145
<211> LENGTH: 44
<212> TYPE: DNA
<213> ORGANISM: Artificial
<220> FEATURE:
<223> OTHER INFORMATION: primer

<400> SEQUENCE: 145

```
atgaaaaaga ttgcatttgg ctgtgcaacc attatcaccg ccag                  44
```

<210> SEQ ID NO 146
<211> LENGTH: 44
<212> TYPE: DNA

```
<213> ORGANISM: Artificial
<220> FEATURE:
<223> OTHER INFORMATION: primer

<400> SEQUENCE: 146
ctgagttttg atttcagtac tcattttctg ttgggccatt gcat          44

<210> SEQ ID NO 147
<211> LENGTH: 44
<212> TYPE: DNA
<213> ORGANISM: Artificial
<220> FEATURE:
<223> OTHER INFORMATION: primer

<400> SEQUENCE: 147
atgagtactg aaatcaaaac tcaggcaacc attatcaccg ccag          44

<210> SEQ ID NO 148
<211> LENGTH: 44
<212> TYPE: DNA
<213> ORGANISM: Artificial
<220> FEATURE:
<223> OTHER INFORMATION: primer

<400> SEQUENCE: 148
actaaaattg aagatttgag ccattttctg ttgggccatt gcat          44

<210> SEQ ID NO 149
<211> LENGTH: 44
<212> TYPE: DNA
<213> ORGANISM: Artificial
<220> FEATURE:
<223> OTHER INFORMATION: primer

<400> SEQUENCE: 149
atggctcaaa tcttcaattt tagtgcaacc attatcaccg ccag          44

<210> SEQ ID NO 150
<211> LENGTH: 44
<212> TYPE: DNA
<213> ORGANISM: Artificial
<220> FEATURE:
<223> OTHER INFORMATION: primer

<400> SEQUENCE: 150
gtcgcaccag gtaatgttag gcattttctg ttgggccatt gcat          44

<210> SEQ ID NO 151
<211> LENGTH: 44
<212> TYPE: DNA
<213> ORGANISM: Artificial
<220> FEATURE:
<223> OTHER INFORMATION: primer

<400> SEQUENCE: 151
atgcctaaca ttacctggtg cgacgcaacc attatcaccg ccag          44

<210> SEQ ID NO 152
<211> LENGTH: 44
<212> TYPE: DNA
<213> ORGANISM: Artificial
<220> FEATURE:
<223> OTHER INFORMATION: primer

<400> SEQUENCE: 152
tttctccagc gatacctttg ccattttctg ttgggccatt gcat          44
```

<210> SEQ ID NO 153
<211> LENGTH: 44
<212> TYPE: DNA
<213> ORGANISM: Artificial
<220> FEATURE:
<223> OTHER INFORMATION: primer

<400> SEQUENCE: 153
atggcaaagg tatcgctgga gaaagcaacc attatcaccg ccag        44

<210> SEQ ID NO 154
<211> LENGTH: 30
<212> TYPE: DNA
<213> ORGANISM: Artificial
<220> FEATURE:
<223> OTHER INFORMATION: primer

<400> SEQUENCE: 154
ctagggatcc ttataaaagc tcttcgtacg        30

<210> SEQ ID NO 155
<211> LENGTH: 33
<212> TYPE: DNA
<213> ORGANISM: Artificial
<220> FEATURE:
<223> OTHER INFORMATION: primer

<400> SEQUENCE: 155
ggaattccat atgatgaaga tttacggaat tta        33

<210> SEQ ID NO 156
<211> LENGTH: 52
<212> TYPE: DNA
<213> ORGANISM: Artificial
<220> FEATURE:
<223> OTHER INFORMATION: primer

<400> SEQUENCE: 156
tggcgtaatg cagcagaaaa tggcccgcga aattaatacg actcactata gg        52

<210> SEQ ID NO 157
<211> LENGTH: 140
<212> TYPE: DNA
<213> ORGANISM: Artificial
<220> FEATURE:
<223> OTHER INFORMATION: primer

<400> SEQUENCE: 157
gataaaattc gctaaaagac atatgtatat ctccttctta aagttaaaca aaattatttc        60
tagaggggaa ttgttatccg ctcacaattc ccctatagtg agtcgtatta atttcgcggg      120
ttataaaagc tcttcgtacg      140

<210> SEQ ID NO 158
<211> LENGTH: 44
<212> TYPE: DNA
<213> ORGANISM: Artificial
<220> FEATURE:
<223> OTHER INFORMATION: primer

<400> SEQUENCE: 158
tggcgtaatg cagcagaaaa tggtcagaag aactcgtcaa gaag        44

<210> SEQ ID NO 159

-continued

```
<211> LENGTH: 43
<212> TYPE: DNA
<213> ORGANISM: Artificial
<220> FEATURE:
<223> OTHER INFORMATION: primer

<400> SEQUENCE: 159
gataaaattc gctaaaagac atcatcacat atacctgccg ttc            43

<210> SEQ ID NO 160
<211> LENGTH: 21
<212> TYPE: DNA
<213> ORGANISM: Artificial
<220> FEATURE:
<223> OTHER INFORMATION: primer

<400> SEQUENCE: 160
gaacgtcgtc cggctgatgc c                                    21

<210> SEQ ID NO 161
<211> LENGTH: 23
<212> TYPE: DNA
<213> ORGANISM: Artificial
<220> FEATURE:
<223> OTHER INFORMATION: primer

<400> SEQUENCE: 161
tggtatcggt ctgcgattcc gac                                  23

<210> SEQ ID NO 162
<211> LENGTH: 36
<212> TYPE: DNA
<213> ORGANISM: Artificial
<220> FEATURE:
<223> OTHER INFORMATION: primer

<400> SEQUENCE: 162
ggaattccat atggtgactg acagcgagaa ggtggc                    36

<210> SEQ ID NO 163
<211> LENGTH: 37
<212> TYPE: DNA
<213> ORGANISM: Artificial
<220> FEATURE:
<223> OTHER INFORMATION: primer

<400> SEQUENCE: 163
ctagagaatt cctagtctac aggtcctctc ccccgcc                   37

<210> SEQ ID NO 164
<211> LENGTH: 35
<212> TYPE: DNA
<213> ORGANISM: Artificial
<220> FEATURE:
<223> OTHER INFORMATION: primer

<400> SEQUENCE: 164
ggaattccat atgatgagcg gtgacaacgg catga                     35

<210> SEQ ID NO 165
<211> LENGTH: 31
<212> TYPE: DNA
<213> ORGANISM: Artificial
<220> FEATURE:
<223> OTHER INFORMATION: primer

<400> SEQUENCE: 165
```
gatgaattct catgaattcc ctccgcccag c                                   31

<210> SEQ ID NO 166
<211> LENGTH: 36
<212> TYPE: DNA
<213> ORGANISM: Artificial
<220> FEATURE:
<223> OTHER INFORMATION: primer

<400> SEQUENCE: 166
ggaattccat atggtggcgg acctgtcaaa gctctc                              36

<210> SEQ ID NO 167
<211> LENGTH: 30
<212> TYPE: DNA
<213> ORGANISM: Artificial
<220> FEATURE:
<223> OTHER INFORMATION: primer

<400> SEQUENCE: 167
gatgaattct caatcgccgt cgagctcccg                                     30

<210> SEQ ID NO 168
<211> LENGTH: 35
<212> TYPE: DNA
<213> ORGANISM: Artificial
<220> FEATURE:
<223> OTHER INFORMATION: primer

<400> SEQUENCE: 168
ggaattccat atgatgggca gcagccatca tcatc                               35

<210> SEQ ID NO 169
<211> LENGTH: 31
<212> TYPE: DNA
<213> ORGANISM: Artificial
<220> FEATURE:
<223> OTHER INFORMATION: primer

<400> SEQUENCE: 169
ctagactagt ttacaggggg atgttgccgt g                                   31

<210> SEQ ID NO 170
<211> LENGTH: 43
<212> TYPE: DNA
<213> ORGANISM: Artificial
<220> FEATURE:
<223> OTHER INFORMATION: primer

<400> SEQUENCE: 170
caccaataac tgccttaaaa aaagccaatc gactggcgag cgg                      43

<210> SEQ ID NO 171
<211> LENGTH: 50
<212> TYPE: DNA
<213> ORGANISM: Artificial
<220> FEATURE:
<223> OTHER INFORMATION: primer

<400> SEQUENCE: 171
tcgagatttt caggagctaa ggaagctaaa atgcaatacg aatggcgaaa               50

<210> SEQ ID NO 172
<211> LENGTH: 43
<212> TYPE: DNA

<213> ORGANISM: Artificial
<220> FEATURE:
<223> OTHER INFORMATION: primer

<400> SEQUENCE: 172
ccgctcgcca gtcgattggc ttttttaag gcagttattg gtg                43

<210> SEQ ID NO 173
<211> LENGTH: 50
<212> TYPE: DNA
<213> ORGANISM: Artificial
<220> FEATURE:
<223> OTHER INFORMATION: primer

<400> SEQUENCE: 173
tttcgccatt cgtattgcat tttagcttcc ttagctcctg aaaatctcga        50

<210> SEQ ID NO 174
<211> LENGTH: 24
<212> TYPE: DNA
<213> ORGANISM: Artificial
<220> FEATURE:
<223> OTHER INFORMATION: target gene binding sequence

<400> SEQUENCE: 174
ctgggctgtt tgcgttaccg ccat                                    24

<210> SEQ ID NO 175
<211> LENGTH: 24
<212> TYPE: DNA
<213> ORGANISM: Artificial
<220> FEATURE:
<223> OTHER INFORMATION: target gene binding sequence

<400> SEQUENCE: 175
ggcgatataa actgtttgct tcat                                    24

<210> SEQ ID NO 176
<211> LENGTH: 24
<212> TYPE: DNA
<213> ORGANISM: Artificial
<220> FEATURE:
<223> OTHER INFORMATION: target gene binding sequence

<400> SEQUENCE: 176
tacgccgatc tgttgcttgg acat                                    24

<210> SEQ ID NO 177
<211> LENGTH: 24
<212> TYPE: DNA
<213> ORGANISM: Artificial
<220> FEATURE:
<223> OTHER INFORMATION: target gene binding sequence

<400> SEQUENCE: 177
gggggcaatc aaatactgtt tcat                                    24

<210> SEQ ID NO 178
<211> LENGTH: 24
<212> TYPE: DNA
<213> ORGANISM: Artificial
<220> FEATURE:
<223> OTHER INFORMATION: target gene binding sequence

<400> SEQUENCE: 178
tttgatgccg tctaactcgt tcat                                    24

```
<210> SEQ ID NO 179
<211> LENGTH: 24
<212> TYPE: DNA
<213> ORGANISM: Artificial
<220> FEATURE:
<223> OTHER INFORMATION: target gene binding sequence

<400> SEQUENCE: 179
aagggaggtc aatttgtccg tcat                                          24

<210> SEQ ID NO 180
<211> LENGTH: 24
<212> TYPE: DNA
<213> ORGANISM: Artificial
<220> FEATURE:
<223> OTHER INFORMATION: target gene binding sequence

<400> SEQUENCE: 180
ggcaagctct ttacgtgagg acat                                          24

<210> SEQ ID NO 181
<211> LENGTH: 24
<212> TYPE: DNA
<213> ORGANISM: Artificial
<220> FEATURE:
<223> OTHER INFORMATION: target gene binding sequence

<400> SEQUENCE: 181
attggcaagg tcttttcggg acat                                          24

<210> SEQ ID NO 182
<211> LENGTH: 24
<212> TYPE: DNA
<213> ORGANISM: Artificial
<220> FEATURE:
<223> OTHER INFORMATION: target gene binding sequence

<400> SEQUENCE: 182
aagcgggatt tgtttggaca acat                                          24

<210> SEQ ID NO 183
<211> LENGTH: 24
<212> TYPE: DNA
<213> ORGANISM: Artificial
<220> FEATURE:
<223> OTHER INFORMATION: target gene binding sequence

<400> SEQUENCE: 183
atcttcggta atgattaatt tcat                                          24

<210> SEQ ID NO 184
<211> LENGTH: 24
<212> TYPE: DNA
<213> ORGANISM: Artificial
<220> FEATURE:
<223> OTHER INFORMATION: target gene binding sequencee

<400> SEQUENCE: 184
gcggactgga cgacgttgtt gcat                                          24

<210> SEQ ID NO 185
<211> LENGTH: 24
<212> TYPE: DNA
<213> ORGANISM: Artificial
<220> FEATURE:
```

```
<223> OTHER INFORMATION: target gene binding sequence

<400> SEQUENCE: 185
tttctgatat agcggattag ccat                                              24

<210> SEQ ID NO 186
<211> LENGTH: 24
<212> TYPE: DNA
<213> ORGANISM: Artificial
<220> FEATURE:
<223> OTHER INFORMATION: target gene binding sequence

<400> SEQUENCE: 186
ctgcaattta ttatcgtgtg tcat                                              24

<210> SEQ ID NO 187
<211> LENGTH: 24
<212> TYPE: DNA
<213> ORGANISM: Artificial
<220> FEATURE:
<223> OTHER INFORMATION: target gene binding sequence

<400> SEQUENCE: 187
aagctggcat acttgatcta acat                                              24

<210> SEQ ID NO 188
<211> LENGTH: 24
<212> TYPE: DNA
<213> ORGANISM: Artificial
<220> FEATURE:
<223> OTHER INFORMATION: target gene binding sequence

<400> SEQUENCE: 188
taatacctgg gatggtgcag tcat                                              24

<210> SEQ ID NO 189
<211> LENGTH: 24
<212> TYPE: DNA
<213> ORGANISM: Artificial
<220> FEATURE:
<223> OTHER INFORMATION: target gene binding sequence

<400> SEQUENCE: 189
aatataaagc gtgccttgag ccat                                              24

<210> SEQ ID NO 190
<211> LENGTH: 24
<212> TYPE: DNA
<213> ORGANISM: Artificial
<220> FEATURE:
<223> OTHER INFORMATION: target gene binding sequence

<400> SEQUENCE: 190
atgcttatga atgttttccg tcat                                              24

<210> SEQ ID NO 191
<211> LENGTH: 24
<212> TYPE: DNA
<213> ORGANISM: Artificial
<220> FEATURE:
<223> OTHER INFORMATION: target gene binding sequence

<400> SEQUENCE: 191
agcttcttta gcgatacgta gcat                                              24
```

```
<210> SEQ ID NO 192
<211> LENGTH: 24
<212> TYPE: DNA
<213> ORGANISM: Artificial
<220> FEATURE:
<223> OTHER INFORMATION: target gene binding sequence

<400> SEQUENCE: 192
ggaaaaagta cgttcaatag ccat                                           24

<210> SEQ ID NO 193
<211> LENGTH: 24
<212> TYPE: DNA
<213> ORGANISM: Artificial
<220> FEATURE:
<223> OTHER INFORMATION: target gene binding sequence

<400> SEQUENCE: 193
agaagatgaa gcagttaacg tcat                                           24

<210> SEQ ID NO 194
<211> LENGTH: 24
<212> TYPE: DNA
<213> ORGANISM: Artificial
<220> FEATURE:
<223> OTHER INFORMATION: target gene binding sequence

<400> SEQUENCE: 194
aaactggcgc tgatatggtt tcat                                           24

<210> SEQ ID NO 195
<211> LENGTH: 24
<212> TYPE: DNA
<213> ORGANISM: Artificial
<220> FEATURE:
<223> OTHER INFORMATION: target gene binding sequence

<400> SEQUENCE: 195
gacgggtttt gcattggtag ccat                                           24

<210> SEQ ID NO 196
<211> LENGTH: 24
<212> TYPE: DNA
<213> ORGANISM: Artificial
<220> FEATURE:
<223> OTHER INFORMATION: target gene binding sequence

<400> SEQUENCE: 196
cattacttct acagtatgtt tcat                                           24

<210> SEQ ID NO 197
<211> LENGTH: 44
<212> TYPE: DNA
<213> ORGANISM: Artificial
<220> FEATURE:
<223> OTHER INFORMATION: target gene binding sequence

<400> SEQUENCE: 197
ctgggctgtt tgcgttaccg ccattttctg ttgggccatt gcat                     44

<210> SEQ ID NO 198
<211> LENGTH: 44
<212> TYPE: DNA
<213> ORGANISM: Artificial
<220> FEATURE:
<223> OTHER INFORMATION: target gene binding sequence
```

<400> SEQUENCE: 198
atggcggtaa cgcaaacagc ccaggcaacc attatcaccg ccag    44

<210> SEQ ID NO 199
<211> LENGTH: 44
<212> TYPE: DNA
<213> ORGANISM: Artificial
<220> FEATURE:
<223> OTHER INFORMATION: target gene binding sequence

<400> SEQUENCE: 199
ggcgatataa actgtttgct tcattttctg ttgggccatt gcat    44

<210> SEQ ID NO 200
<211> LENGTH: 44
<212> TYPE: DNA
<213> ORGANISM: Artificial
<220> FEATURE:
<223> OTHER INFORMATION: target gene binding sequence

<400> SEQUENCE: 200
atgaagcaaa cagtttatat cgccgcaacc attatcaccg ccag    44

<210> SEQ ID NO 201
<211> LENGTH: 44
<212> TYPE: DNA
<213> ORGANISM: Artificial
<220> FEATURE:
<223> OTHER INFORMATION: target gene binding sequence

<400> SEQUENCE: 201
tacgccgatc tgttgcttgg acattttctg ttgggccatt gcat    44

<210> SEQ ID NO 202
<211> LENGTH: 44
<212> TYPE: DNA
<213> ORGANISM: Artificial
<220> FEATURE:
<223> OTHER INFORMATION: target gene binding sequence

<400> SEQUENCE: 202
atgtccaagc aacagatcgg cgtagcaacc attatcaccg ccag    44

<210> SEQ ID NO 203
<211> LENGTH: 48
<212> TYPE: DNA
<213> ORGANISM: Artificial
<220> FEATURE:
<223> OTHER INFORMATION: target gene binding sequence

<400> SEQUENCE: 203
gggggcaatc aaatactgtt tcattttctg ttgggccatt gcattgcc    48

<210> SEQ ID NO 204
<211> LENGTH: 49
<212> TYPE: DNA
<213> ORGANISM: Artificial
<220> FEATURE:
<223> OTHER INFORMATION: target gene binding sequence

<400> SEQUENCE: 204
atgaaacagt atttgattgc ccccgcaacc attatcaccg ccagaggta    49

<210> SEQ ID NO 205
<211> LENGTH: 48

```
<212> TYPE: DNA
<213> ORGANISM: Artificial
<220> FEATURE:
<223> OTHER INFORMATION: target gene binding sequence

<400> SEQUENCE: 205
tttgatgccg tctaactcgt tcattttctg ttgggccatt gcattgcc                48

<210> SEQ ID NO 206
<211> LENGTH: 49
<212> TYPE: DNA
<213> ORGANISM: Artificial
<220> FEATURE:
<223> OTHER INFORMATION: target gene binding sequence

<400> SEQUENCE: 206
atgaacgagt tagacggcat caaagcaacc attatcaccg ccagaggta               49

<210> SEQ ID NO 207
<211> LENGTH: 48
<212> TYPE: DNA
<213> ORGANISM: Artificial
<220> FEATURE:
<223> OTHER INFORMATION: target gene binding sequence

<400> SEQUENCE: 207
aagggaggtc aatttgtccg tcattttctg ttgggccatt gcattgcc                48

<210> SEQ ID NO 208
<211> LENGTH: 49
<212> TYPE: DNA
<213> ORGANISM: Artificial
<220> FEATURE:
<223> OTHER INFORMATION: target gene binding sequence

<400> SEQUENCE: 208
atgacggaca aattgacctc ccttgcaacc attatcaccg ccagaggta               49

<210> SEQ ID NO 209
<211> LENGTH: 48
<212> TYPE: DNA
<213> ORGANISM: Artificial
<220> FEATURE:
<223> OTHER INFORMATION: primer

<400> SEQUENCE: 209
ggcaagctct ttacgtgagg acattttctg ttgggccatt gcattgcc                48

<210> SEQ ID NO 210
<211> LENGTH: 49
<212> TYPE: DNA
<213> ORGANISM: Artificial
<220> FEATURE:
<223> OTHER INFORMATION: primer

<400> SEQUENCE: 210
atgtcctcac gtaaagagct tgccgcaacc attatcaccg ccagaggta               49

<210> SEQ ID NO 211
<211> LENGTH: 48
<212> TYPE: DNA
<213> ORGANISM: Artificial
<220> FEATURE:
<223> OTHER INFORMATION: primer

<400> SEQUENCE: 211
```
attggcaagg tctttcggg acattttctg ttgggccatt gcattgcc                48

<210> SEQ ID NO 212
<211> LENGTH: 49
<212> TYPE: DNA
<213> ORGANISM: Artificial
<220> FEATURE:
<223> OTHER INFORMATION: primer

<400> SEQUENCE: 212
atgtcccgaa aagaccttgc caatgcaacc attatcaccg ccagaggta                49

<210> SEQ ID NO 213
<211> LENGTH: 48
<212> TYPE: DNA
<213> ORGANISM: Artificial
<220> FEATURE:
<223> OTHER INFORMATION: primer

<400> SEQUENCE: 213
aagcgggatt tgtttggaca acattttctg ttgggccatt gcattgcc                48

<210> SEQ ID NO 214
<211> LENGTH: 49
<212> TYPE: DNA
<213> ORGANISM: Artificial
<220> FEATURE:
<223> OTHER INFORMATION: primer

<400> SEQUENCE: 214
atgttgtcca aacaaatccc gcttgcaacc attatcaccg ccagaggta                49

<210> SEQ ID NO 215
<211> LENGTH: 48
<212> TYPE: DNA
<213> ORGANISM: Artificial
<220> FEATURE:
<223> OTHER INFORMATION: primer

<400> SEQUENCE: 215
atcttcggta atgattaatt tcattttctg ttgggccatt gcattgcc                48

<210> SEQ ID NO 216
<211> LENGTH: 49
<212> TYPE: DNA
<213> ORGANISM: Artificial
<220> FEATURE:
<223> OTHER INFORMATION: primer

<400> SEQUENCE: 216
atgaaattaa tcattaccga agatgcaacc attatcaccg ccagaggta                49

<210> SEQ ID NO 217
<211> LENGTH: 48
<212> TYPE: DNA
<213> ORGANISM: Artificial
<220> FEATURE:
<223> OTHER INFORMATION: primer

<400> SEQUENCE: 217
gcggactgga cgacgttgtt gcattttctg ttgggccatt gcattgcc                48

<210> SEQ ID NO 218
<211> LENGTH: 49
<212> TYPE: DNA
<213> ORGANISM: Artificial

```
<220> FEATURE:
<223> OTHER INFORMATION: primer

<400> SEQUENCE: 218
atgcaacaac gtcgtccagt ccgcgcaacc attatcaccg ccagaggta          49

<210> SEQ ID NO 219
<211> LENGTH: 48
<212> TYPE: DNA
<213> ORGANISM: Artificial
<220> FEATURE:
<223> OTHER INFORMATION: primer

<400> SEQUENCE: 219
tttctgatat agcggattag ccatttctg ttgggccatt gcattgcc            48

<210> SEQ ID NO 220
<211> LENGTH: 49
<212> TYPE: DNA
<213> ORGANISM: Artificial
<220> FEATURE:
<223> OTHER INFORMATION: primer

<400> SEQUENCE: 220
atggctaatc cgctatatca gaaagcaacc attatcaccg ccagaggta          49

<210> SEQ ID NO 221
<211> LENGTH: 48
<212> TYPE: DNA
<213> ORGANISM: Artificial
<220> FEATURE:
<223> OTHER INFORMATION: primer

<400> SEQUENCE: 221
ctgcaattta ttatcgtgtg tcattttctg ttgggccatt gcattgcc           48

<210> SEQ ID NO 222
<211> LENGTH: 49
<212> TYPE: DNA
<213> ORGANISM: Artificial
<220> FEATURE:
<223> OTHER INFORMATION: primer

<400> SEQUENCE: 222
atgacacacg ataataaatt gcaggcaacc attatcaccg ccagaggta          49

<210> SEQ ID NO 223
<211> LENGTH: 48
<212> TYPE: DNA
<213> ORGANISM: Artificial
<220> FEATURE:
<223> OTHER INFORMATION: primer

<400> SEQUENCE: 223
aagctggcat acttgatcta acattttctg ttgggccatt gcattgcc           48

<210> SEQ ID NO 224
<211> LENGTH: 49
<212> TYPE: DNA
<213> ORGANISM: Artificial
<220> FEATURE:
<223> OTHER INFORMATION: primer

<400> SEQUENCE: 224
atgttagatc aagtatgcca gcttgcaacc attatcaccg ccagaggta          49
```

<210> SEQ ID NO 225
<211> LENGTH: 48
<212> TYPE: DNA
<213> ORGANISM: Artificial
<220> FEATURE:
<223> OTHER INFORMATION: primer

<400> SEQUENCE: 225
taatacctgg gatggtgcag tcattttctg ttgggccatt gcattgcc        48

<210> SEQ ID NO 226
<211> LENGTH: 49
<212> TYPE: DNA
<213> ORGANISM: Artificial
<220> FEATURE:
<223> OTHER INFORMATION: primer

<400> SEQUENCE: 226
atgactgcac catcccaggt attagcaacc attatcaccg ccagaggta       49

<210> SEQ ID NO 227
<211> LENGTH: 48
<212> TYPE: DNA
<213> ORGANISM: Artificial
<220> FEATURE:
<223> OTHER INFORMATION: primer

<400> SEQUENCE: 227
aatataaagc gtgccttgag ccattttctg ttgggccatt gcattgcc        48

<210> SEQ ID NO 228
<211> LENGTH: 49
<212> TYPE: DNA
<213> ORGANISM: Artificial
<220> FEATURE:
<223> OTHER INFORMATION: primer

<400> SEQUENCE: 228
atggctcaag gcacgcttta tattgcaacc attatcaccg ccagaggta       49

<210> SEQ ID NO 229
<211> LENGTH: 48
<212> TYPE: DNA
<213> ORGANISM: Artificial
<220> FEATURE:
<223> OTHER INFORMATION: primer

<400> SEQUENCE: 229
atgcttatga atgttttccg tcattttctg ttgggccatt gcattgcc        48

<210> SEQ ID NO 230
<211> LENGTH: 49
<212> TYPE: DNA
<213> ORGANISM: Artificial
<220> FEATURE:
<223> OTHER INFORMATION: primer

<400> SEQUENCE: 230
atgacggaaa acattcataa gcatgcaacc attatcaccg ccagaggta       49

<210> SEQ ID NO 231
<211> LENGTH: 48
<212> TYPE: DNA
<213> ORGANISM: Artificial
<220> FEATURE:
<223> OTHER INFORMATION: primer

```
<400> SEQUENCE: 231
agcttcttta gcgatacgta gcatttnctg ttgggccatt gcattgcc          48

<210> SEQ ID NO 232
<211> LENGTH: 49
<212> TYPE: DNA
<213> ORGANISM: Artificial
<220> FEATURE:
<223> OTHER INFORMATION: primer

<400> SEQUENCE: 232
atgctacgta tcgctaaaga agctgcaacc attatcaccg ccagaggta          49

<210> SEQ ID NO 233
<211> LENGTH: 48
<212> TYPE: DNA
<213> ORGANISM: Artificial
<220> FEATURE:
<223> OTHER INFORMATION: primer

<400> SEQUENCE: 233
ggaaaaagta cgttcaatag ccatttnctg ttgggccatt gcattgcc          48

<210> SEQ ID NO 234
<211> LENGTH: 49
<212> TYPE: DNA
<213> ORGANISM: Artificial
<220> FEATURE:
<223> OTHER INFORMATION: primer

<400> SEQUENCE: 234
atggctattg aacgtacttt ttccgcaacc attatcaccg ccagaggta          49

<210> SEQ ID NO 235
<211> LENGTH: 48
<212> TYPE: DNA
<213> ORGANISM: Artificial
<220> FEATURE:
<223> OTHER INFORMATION: primer

<400> SEQUENCE: 235
agaagatgaa gcagttaacg tcatttnctg ttgggccatt gcattgcc          48

<210> SEQ ID NO 236
<211> LENGTH: 49
<212> TYPE: DNA
<213> ORGANISM: Artificial
<220> FEATURE:
<223> OTHER INFORMATION: primer

<400> SEQUENCE: 236
atgacgttaa ctgcttcatc ttctgcaacc attatcaccg ccagaggta          49

<210> SEQ ID NO 237
<211> LENGTH: 48
<212> TYPE: DNA
<213> ORGANISM: Artificial
<220> FEATURE:
<223> OTHER INFORMATION: primer

<400> SEQUENCE: 237
aaactggcgc tgatatggtt tcatttnctg ttgggccatt gcattgcc          48

<210> SEQ ID NO 238
```

```
<211> LENGTH: 49
<212> TYPE: DNA
<213> ORGANISM: Artificial
<220> FEATURE:
<223> OTHER INFORMATION: primer

<400> SEQUENCE: 238
atgaaaccat atcagcgcca gtttgcaacc attatcaccg ccagaggta            49

<210> SEQ ID NO 239
<211> LENGTH: 48
<212> TYPE: DNA
<213> ORGANISM: Artificial
<220> FEATURE:
<223> OTHER INFORMATION: primer

<400> SEQUENCE: 239
gacgggtttt gcattggtag ccattttctg ttgggccatt gcattgcc             48

<210> SEQ ID NO 240
<211> LENGTH: 49
<212> TYPE: DNA
<213> ORGANISM: Artificial
<220> FEATURE:
<223> OTHER INFORMATION: primer

<400> SEQUENCE: 240
atggctacca atgcaaaacc cgtcgcaacc attatcaccg ccagaggta            49

<210> SEQ ID NO 241
<211> LENGTH: 48
<212> TYPE: DNA
<213> ORGANISM: Artificial
<220> FEATURE:
<223> OTHER INFORMATION: primer

<400> SEQUENCE: 241
cattacttct acagtatgtt tcattttctg ttgggccatt gcattgcc             48

<210> SEQ ID NO 242
<211> LENGTH: 49
<212> TYPE: DNA
<213> ORGANISM: Artificial
<220> FEATURE:
<223> OTHER INFORMATION: primer

<400> SEQUENCE: 242
atgaaacata ctgtagaagt aatggcaacc attatcaccg ccagaggta            49
```